(12) United States Patent
Wagner, Jr. et al.

(10) Patent No.: US 11,744,875 B2
(45) Date of Patent: *Sep. 5, 2023

(54) PEPTIDES AND METHODS FOR TREATING DISEASE

(71) Applicant: OP-T LLC, Denver, CO (US)

(72) Inventors: David Hal Wagner, Jr., Denver, CO (US); Martin Glenn Yussman, Denver, CO (US); Charles W. Henry, Denver, CO (US)

(73) Assignee: OP-T LLC, Aurora, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/926,782

(22) Filed: Jul. 13, 2020

(65) Prior Publication Data

US 2021/0008162 A1 Jan. 14, 2021

Related U.S. Application Data

(60) Provisional application No. 62/873,776, filed on Jul. 12, 2019.

(51) Int. Cl.
| | | |
|---|---|---|
| *A61K 38/08* | (2019.01) | |
| *A61K 38/17* | (2006.01) | |
| *A61P 3/10* | (2006.01) | |
| *A61K 38/10* | (2006.01) | |

(52) U.S. Cl.
CPC .......... *A61K 38/1793* (2013.01); *A61K 38/08* (2013.01); *A61K 38/10* (2013.01); *A61P 3/10* (2018.01)

(58) Field of Classification Search
CPC .................................. A61K 38/08; A61P 3/10
See application file for complete search history.

(56) References Cited

U.S. PATENT DOCUMENTS

| | | | |
|---|---|---|---|
| 4,642,295 A | 2/1987 | Baker | |
| 6,264,951 B1 | 7/2001 | Armitage | |
| 7,087,573 B1 | 8/2006 | Lazarus | |
| 7,741,280 B2 | 6/2010 | Guichard et al. | |
| 9,562,088 B2 * | 2/2017 | Wagner | C07K 14/70575 |
| 2003/0078269 A1 * | 4/2003 | Pearson | A61K 31/16 514/251 |
| 2005/0202531 A1 | 9/2005 | Toporik | |
| 2007/0041971 A1 | 2/2007 | Wagner | |
| 2011/0178000 A1 | 7/2011 | Freyberg et al. | |
| 2012/0282291 A1 | 11/2012 | Berghman et al. | |
| 2015/0366946 A1 * | 12/2015 | Vol | A61K 38/28 424/450 |
| 2016/0200823 A1 | 7/2016 | Burkly et al. | |
| 2017/0319671 A1 | 11/2017 | Faulkner et al. | |
| 2019/0194290 A1 | 6/2019 | Wagner, Jr. et al. | |
| 2021/0008162 A1 | 1/2021 | Wagner, Jr. et al. | |

FOREIGN PATENT DOCUMENTS

| | | |
|---|---|---|
| WO | WO-2008/036675 A2 | 3/2008 |
| WO | WO-2019/032945 A1 | 2/2019 |
| WO | WO-2019/136307 A1 | 7/2019 |
| WO | WO-2021/011437 A1 | 1/2021 |
| WO | WO-2021/231898 A2 | 11/2021 |

OTHER PUBLICATIONS

Wang et al. "Parenteral Formulations of Proteins and Peptides: Stability and Stabilizers", Journal of Parenteral Science and Technology, 1988, S3-S25 (Year: 1988).*
Huang et al., "Resolving the Conundrum of Islet Transplantation by Linking Metabolic Dysregulation, Inflammation, and Immune Regulation", Endocrine Reviews, 2008; pp. 603-630 (Year: 2008).*
Hancock, "Preventing and managing diabetes: an exemplar for NCDs", C3 Collaborating for Health, www.c3health.org, 2012, pp. 1-8 (Year: 2012).*
Wang et al. "Parenteral Formulations of Proteins and Peptides: Stability and Stabilizers", Journal of Parenteral Science and Technology, 1988, S3-S25 (Year: 1998).*
Patel et al. "Recent developments in protein and peptide parenteral delivery approaches", Ther. Deliv., 2014, 337-365 (Year: 2014).*
Bak et al. "Physicochemical and Formulation Developability Assessment for Therapeutic Peptide Delivery—A Primer", The AAPS Journal, 2015, 144-155 (Year: 2015).*
Shukshith et al. "Water for Pharmaceutical Use", Int. J. Pharm. Sci. Rev. Res., 2016, pp. 199-204 (Year: 2016).*
Vaitaitis et al. "A CD40 targeting peptide prevents severe symptoms in experimental autoimmune encephalomyelitis", Journal of Neuroimmunology, published online Mar. 21, 2019 (Year: 2019).*
Biosyn "Why acetylate and amidate a peptide", accessed on Mar. 22, 2021 at https://www.biosyn.com/faq/why-acetylate-and-amidate-apeptide.aspx., 2008 (Year: 2008).*
Wikipedia, "Phosphate-buffered saline", https://en.wikipedia.org/wiki/Phosphate-buffered_saline, Accessed on Mar. 25, 2022 (Year: 2022).*

(Continued)

*Primary Examiner* — Lianko G Garyu
(74) *Attorney, Agent, or Firm* — Foley Hoag LLP; Brendan T. Jones; David E. Shore

(57) ABSTRACT

Bioactive peptides and methods for their use for preventing, treating, and/or reducing the incidence and/or symptoms of an autoimmune disease or disorder that may result from chronic inflammation, damage to β-cells of the pancreas, and other conditions that are implicated by the CD40-CD154 dyad. In particular, small peptides that are capable of interacting with CD40, thereby interfering with the ability of CD40 to interact with CD154, which impacts inflammation, autoimmunity, and disease progression. The use of such peptides in reducing diabetes mellitus, and in particular, the autoimmune inflammatory response that may be a driving factor thereof. Methods and materials for preventing and modulating diabetes mellitus and autoimmune diseases especially in dogs, cats, and horses.

21 Claims, 27 Drawing Sheets
Specification includes a Sequence Listing.

(56) References Cited

OTHER PUBLICATIONS

Vaitaitis et al. "A CD40-targeted peptide controls and reverses type 1 diabetes in NOD mice." Diabetologia, 2366-2373, 2014 (Year: 2014).*
Nelson et al., "Classification and etiology of diabetes in dogs and cats", Thematic Review, T1-T9, 2014 (Year: 2014).*
Grant application entitled "Developing a small peptide to control autoimmune inflammation in type 1 diabetes" by PI: David H, Wagner and received on Sep. 2, 2016 and publicly available on Jan. 5, 2018, p. 1-46 (Year: 2018).*
International Search Report and Written Opinion for International Application No. PCT/US2020/041744 dated Nov. 13, 2020.
Leighton et al., "A Practical Review of C-Peptide Testing in Diabetes," Diabetes Ther, 8: 475-487 (2017).
Aart et al., Inhibition of CD40-TRAF6 interactions by the small molecule inhibitor 6877002 reduces neuroinflammation, Journal of Neuroinflammation, 14: 105-118 (2014).
Advisory Action for U.S. Appl. No. 13/880,387, dated May 27, 2016, 4 pages.
Allen et al., "Therapeutic peptidomimetic strategies for autoimmune diseases: costimulation blockade," The Journal of Peptide Research, 65(6): 591-604 (2005).
Amer. Diabetes Association Diagnosis and Classification of Diabetes Mellitus, Diabetes Care, 2014, 37, Suppl.I : S8 I-S90.
Armitage et al., "CD40L: a multi-functional ligand," Semin Immunol, 5(6): 404-412 (1993).
Aruffo et al., "The CD40 Ligand, gp39, Is Defective in Activated T Cells from Patients with X-Linked Hyper-IgM Syndrome," Cell, 72: 291-300 (1993).
Attwood, "The Babel of Bioinformatics," Science, 290(5491): 471-473 (2000).
Balasa et al., "CD40 ligand-CD40 interactions are necessary for the initiation of insulitis and diabetes in nonobese diabetic mice," J Immunol, 159(9): 4620-4627 (1997).
Becker et al., "CD40, an extracellular receptor for binding and uptake of Hsp70-peptide complexes," J Cell Biol, 158(7): 1277-1285 (2002).
Bee et al., "Exploring the Dynamic Range of the Kinetic Exclusion Assay in Characterizing Antigen-Antibody Interactions," Plos One, 7(4): e36261 (2012).
Bojadzic et al., "CD40-targeting KGYY15 peptides do not efficiently block the CD40-CD40L interaction," Diabetologia, 62: 2158-2160 (2019).
Bourgeois et al., "A Role for CD40 Expression on CD8+ T cells in the Generation of CD8+ T Cell Memory," Science, 297: 2060-2063 (2002).
Carter et al., "CD40 engagement of CD4+ CD40+ T cells in a neo-self antigen disease model ablates CTLA-4 expression and indirectly impacts tolerance," Eur J Immunol, 42: 424-435 (2012).
Catchpole et al., "Canine diabetes mellitus: can old dogs teach us new tricks?," Diabetologia, 48: 1948-1956 (2005).
Chatzigeorgiou et al., "Blocking CD40-TRAF6 signaling is a therapeutic target in obesity-associated insulin resistance," PNAS, 111(7): 2686-2691 (2014).
Cipollone et al., "Enhanced soluble CD40 ligand contributes to endothelial cell dysfunction in vitro and monocyte activation in patients with diabetes mellitus: effect of improved metabolic control," Diabetologia, 48: 1216-1224 (2005).
Cooper et al., "Cutting Edge: TCR Revision Occurs in Germinal Centers," J Immunol, 73: 6532-6536 (2004).
Davidson et al., "Co-Stimulatory Blockade in the Treatment of Murine Systemic Lupus Erthematosus (SLE)," NY Acad Sci. 987: 188-198 (2003).
de Ramon et al., "CD154-CD40 T-cell co-stimulation pathway is a key mechanism in kidney ischemia-reperfusion injury," Kidney International, 88(3): 538-549 (2015).
Deambrosis et al., "Inhibition of CD40-CD154 costimulatory pathway by a cyclic peptide targeting CD154," J. Mol. Med., 87: 181-197 (2009).
Devaraj et al., "Increased Monocytic Activity and Biomarkers of Inflammation in Patients With Type 1 Diabetes," Diabetes, 55: 774-779 (2006).
Durie, F.H., R.A. Fava, T.M. Foy, A. Aruffo, J.A. Ledbetter, and R.J. Noelle. 1993. Science 281:1328.
Ellmark et al., "Modulation of the CD40-CD40 ligand interaction using human anti-CD40 single-chain antibody fragments obtained from the n-CoDeR phage display library," Immunology, 106: 456-463 (2002).
Fanslow et al., "Recombinant CD40 ligand exerts potent biologic effects on T cells," J Immunol, 152(9): 4262-4269 (1994).
Final Action for U.S. Appl. No. 13/880,387, dated Feb. 18, 2016, 8 pages.
Goodnow et al., "Pathways for self-tolerance and the treatment of autoimmune diseases," Lancet, 357: 2115-2121 (2001).
Gottlieb et al., "Managing feline diabetes: current perspectives," Vet Med (Auckl), 9: 33-42 (2018).
Grabstein et al., "The regulation of T cell-dependent antibody formation in vitro by CD40 ligand and IL-2," J Immunol, 150(8): 3141-3147 (1993).
Grossman, M.E., E. Davila, and E. Celis. 2001. J Immunother 24:237-241.
Guo et al., "CD40L-Dependent Pathway Is Active at Various Stages of Rheumatoid Arthritis Disease Progression," J Immunol, 198(11): 4490-4501 (2017).
Guptill, L., et al., Vet. J., 2003, 165:240-47.
Heath et al., "Monoclonal antibodies to murine CD40 define two distinct functional epitopes," Eur. J. Immunol., 24: 1828-1834 (1994).
Hernandez et al., "CD40-CD40 Ligand Interaction between Dendritic Cells and CD8+ T Cells Is Needed to Stimulate Maximal T Cell Responses in the Absence of CD4+ T Cell Help," J Immunol, 178(5) 2844-2852 (2007).
Homann et al., "CD40L Blockade Prevents Autoimmune Diabetes by Induction of Bitypic NK/DC Regulatory Cells," Immunity, 16: 403-415 (2002).
Howard, L.M., and S.D. Miller. 2004. Autoimmunity 37:411-418.
International Preliminary Report on Patentability for International Application No. PCT/US11/56860 dated Apr. 23, 2013.
International Search Report and Written Opinion for International Application No. PCT/US11/56860 dated May 4, 2012.
Johnson et al., "Diabetes, Insulin Resistance, and Metabolic Syndrome in Horses," J Diabetes Sci Technol, 6(3): 534-540 (2012).
Karpusas et al., "2 å crystal structure of an extracellular fragment of human CD40 ligand," Structure, 3(10): 1031-1039 (1995).
Khan et al., "Differential peptide binding to CD40 evokes counter-active responses," Hum Immunol, 73(5): 465-469 (2012).
Kitagawa, M., et al.—2014—Modern Rheumatology. vol. 15-6, 423-426.
Kobata et al., "Role of costimulatory molecules in autoimmunity," Rev Immunogenet, 2(1): 74-80 (2000).
Laemmli ., "Cleavage of Structural Proteins during the Assembly of the Head of Bacteriophage T4," Nature, 227: 680-685 (1970).
Lederman et al., "Identification of a novel surface protein on activated CD4+ T cells that induces contact-dependent B cell differentiation (help)," J. Exp. Med., 75(4): 1091-1101 (1992).
Lederman et al., "Molecular interactions mediating T-B lymphocyte collaboration in human lymphoid follicles. Roles of T cell-B-cell-activating molecule (5c8 antigen) and CD40 in contact-dependent help," J Immunol, 149(12): 3817-3826 (1992).
Marsh, Steven G.E. 2012. Human Immunology. vol. 73, 593-596.
Matthews et al., "Utility of murine models for the study of spontaneous autoimmune type 1 diabetes," Pediatric Diabetes, 6: 165-177 (2005).
McWhirter, Sarah, et al.—1999—Biochemistry—vol. 96, 8408-8413.
Munroe et al., "Proinflammatory Adaptive Cytokine and Shed Tumor Necrosis Factor Receptor Levels Are Elevated Preceding Systemic Lupus Erythematosus Disease Flare," Arthritis Rheumatol, 66(7): 1888-1899 (2014).
Notice of Allowance for U.S. Appl. No. 13/880,387, dated Sep. 21, 2016.

(56) References Cited

OTHER PUBLICATIONS

Nourelden et al., "Safety and Efficacy of Teplizumab for Treatment of Type One Diabetes Mellitus: A Systematic Review and Meta-Analysis," Endocr. Metab. Immune Disord Drug Targets, 10: Abstract Only (2020).
O'Kell et al., "Comparative Pathogenesis of Autoimmune Diabetes in Humans, NOD Mice, and Canines: Has a Valuable Animal Model of Type 1 Diabetes Been Overlooked?," Diabetes, 66(7): 1443-1452 (2017).
Official Action for European Application No. 11835055.2, date Feb. 9, 2017, 4 pages.
Official Action for European Application No. 11835055.2, dated Jun. 14, 2016, 4 pages.
Official Action for European Application No. 11835055.2, dated Nov. 20, 2014, 5 pages.
Official Action for U.S. Appl. No. 13/880,387, dated Jun. 24, 2015, 14 pages.
Pullen et al., "CD40 Signaling through Tumor Necrosis Factor Receptor-associated Factors (TRAFs): Binding Site Specificity and Activation of Downstream Pathways By Distinct TRAFs," J Biol Chem, 274(20): 14246-14254 (1999).
Quezada et al., "Distinct Mechanisms of Action of Anti-CD154 in Early Versus Late Treatment of Murine Lupus Nephritis," Arthritis & Rheumatism, 48(9): 2541-2554 (2003).
Ramsdell et al., "CD40 ligand acts as a costimulatory signal for neonatal thymic gamma delta T cells," J Immunol, 152(5): 2190-2197 (1994).
Resetkova et al., "Antibody to gp39, the Ligand for CD40 Significantly Inhibits the Humoral Response from Graves' Thyroid Tissues Xenografted into Severe Combined Immunodeficient (SCID) Mice," Thyroid, 6(4): 267-273 (1996).
Richards et al., "A peptide containing a novel FPGN CD40-binding sequence enhances adenoviral infection of murine and human dendritic cells," Eur. J. Biochem., 270: 2287-2294 (2003).
Rolink et al., "The SCID but Not the RAG-2 Gene Product Is Required for S ?- S? Heavy Chain Class Switching," Immunity, 5(4): 319-330 (1996).
Rosetti et al., "The many faces of Mac-1 in autoimmune disease," Immunological Reviews, 269: 175-193 (2016).
Russo et al., "Platelet-Activating Factor Mediates CD40-Dependent Angiogenesis and Endothelial-Smooth Muscle Cell Interaction," J Immunol, 171: 5489-5497 (2003).
Sarawar et al., "Stimulation via CD40 can substitute for CD4 T cell function in preventing reactivation of a latent herpesvirus," PNAS, 98(11): 6325-6329 (2001).
Schönbeck et al., "CD154 (CD40 ligand)," The International Journal of Biochemistry and Cell Biology, 32(7): 687-693 (2000).
Schönbeck et al., "The CD40/CD154 receptor/ligand dyad," Cell Mol Life Sci, 58: 4-43 (2001).
Seko et al., "Expression of tumour necrosis factor (TNF) receptor/ligand superfamily co-stimulatory molecules CD40, CD30L, CD27L, and OX40L in murine hearts with chronic ongoing myocarditis caused by Coxsackie virus B3," J Pathol, 188: 423-430 (1999).
Skolnick et al., "From genes to protein structure and function: novel applications of computational approaches in the genomic era," Trends in Biotech, 18: 34-39 (2000).
Stumpf et al., "Enhanced levels of CD154 (CD40 ligand) on platelets in patients with; chronic heart failure," Eur J Heart Fail, 5: 629-637 (2003).
Sun, Yonglian et al., "Co-stimulation agonists as a new immunotherapy for autoimmune diseases," Trends Mol Med, 9(11): 483-489 (2003).
Takada et al., "Integrin Binding to the Trimeric Interface of CD40L Plays a Critical Role in CD40/CD40L Signaling," J. Immunol., 203: 1383-1391 (2019).
Toubi et al., "The Role of CD40-CD154 Interactions in Autoimmunity and the Benefit of Disrupting this Pathway," Autoimmunity, 37: 457-464 (2004).
Townsend et al., "CD40 signaling regulates innate and adaptive activation of microglia in response to amyloid ?-peptide," Eur J Immunol, 35: 901-910 (2005).

Vaitaitis et al., "A CD40-targeted peptide controls and reverses type 1 diabetes in NOD mice," Diabetologia, 57: 2366-2373 (2014).
Vaitaitis et al., "CD40-targeted peptide proposed for type 1 diabetes therapy lacks relevant binding affinity to its cognate receptor Reply to Pagni PP, Wolf A, Lo Conte M et al. [letter]," Diabetologia, 62: 1730-1731 (2019).
Vaitaitis et al., "Cutting Edge: CD40-Induced Expression of Recombination Activating Gene (RAG) 1 and RAG2: A Mechanism for the Generation of Autoaggressive T Cells in the Periphery," J Immunol 170: 3455-3459 (2003).
Vaitaitis et al., "High Distribution of CD40 and TRAF2 in Th40 T Cell Rafts Leads to Preferential Survival of this Auto-Aggressive Population in Autoimmunity," PlosOne, 3(4): e2076 (11 pages) (2008).
Vaitaitis et al., "Th40 cells (CD4+CD40+ Tcells) drive a more severe form of Experimental Autoimmune Encephalomyelitis than conventional CD4 T cells," Plos One 12(2): e0172037 (24 pages) (2017).
Vaitaitis et al., Molecular Immunology. vol. 47, 2307-2313 (2010).
Vaitaitis et al.,"An Alternative Role for Foxp3 As an Effector T Cell Regulator Controlled through CD40," J Immunol, 191(2): 717-725 (2013).
Vaitaitis, G.M et al.—2012—PlosOne—vol. 7, e38708, p. 1-13.
Varo et al., "Elevated Plasma Levels of the Atherogenic Mediator Soluble CD40 Ligand in Diabetic Patients," Circulation, 107: 2664-2669 (2003).
Verma et al., "Not Just an Adhesion Molecule: LFA-1 Contact Tunes the T Lymphocyte Program," The Journal of Immunology, 199: 1213-1221 (2017).
Wagner et al., "Expression of CD40 identifies a unique pathogenic T cell population in type 1 diabetes," PNAS, 99(6): 3782-3787 (2002).
Wagner et al., "Increased expression of CD40 on thymocytes and peripheral T cells in autoimmunity: a mechanism for acquiring changes in the peripheral T cell receptor repertoire," Int J Mol Med, 4(3): 231-273 (1999).
Waid et al., "A unique T cell subset described as CD4loCD40+ T cells (TCD40) in human type 1 diabetes," Clinical Immunology, 124: 138-148 (2007).
Waid et al., "Defining a new biomarker for the autoimmune component of Multiple Sclerosis: Th40 cells," J Neuroimmunol, 270(1-2): 75-85 (2014).
Waid et al., "Disruption of the homeostatic balance between autoaggressive (CD4+CD40+) and regulatory (CD4+CD25+FoxP3+) T cells promotes diabetes," J Leukocyte Biol, 84: 431-439 (2008).
Waid et al., "Peripheral CD4lo CD40+ auto-aggressive T cell expansion during insulin-dependent diabetes mellitus," Eur J Immunol, 34: 1488-1497 (2004).
Walling et al., "LFA-1 in T Cell Migration and Differentiation," Frontiers in Immunology, 9: Article 952 (2018).
Yu et al., "Targeting CD40 with a Selective Phage Display Derived Peptide," Universiteit Leiden The Netherlands: 61-74 (2007).
Zhang et al., "The regulation of integrin function by divalent cations," Cell Adhesion & Migration, 6(1): 20-29 (2012).
Bai et al., "Cerebrospinal Fluid and Blood Cytokines as Biomarkers for Multiple Sclerosis: A Systematic Review and Meta-Analysis of 226 Studies With 13,526 Multiple Sclerosis Patients," *Front. Neurosci.*, 2019, 13: 1026.
Buzzard et al., "Multiple Sclerosis: Basic and Clinical," Adv. Neurobiol., 2017, 15: 211-252.
Ceccarelli et al., "Microglia extracellular vesicles: focus on molecular composition and biological function," *Biochem. Soc. Trans.*, 2021, 49(4): 1779-1790.
Chen et al., "CD40/CD40L dyad in the inflammatory and immune responses in the central nervous system," *Cell Mol. Immunol.*, 2006, 3(3): 163-169.
DeGraba et al., "Efficacy of an Interdisciplinary Intensive Outpatient Program in Treating Combat-Related Traumatic Brain Injury and Psychological Health Conditions," *Front Neurol*, 2020, 11: 580182.
Druzd et al., "Lymphocyte Circadian Clocks Control Lymph Node Trafficking and Adaptive Immune Responses," Immunity, 2017; 46: 120-32 [PubMed: 28087238].

(56) References Cited

OTHER PUBLICATIONS

Edwards et al., "Interleukin-6 is associated with acute concussion in military combat personnel," *BMC Neurol.*, 2020, 20(1): 209.
Elliott et al., "Chronic white matter lesion activity predicts clinical progression in primary progressive multiple sclerosis," *Brain a Journal of Neurology*, 2019, 142(9): 2787-2799.
Eshaghi et al., "Progression of regional grey matter atrophy in multiple sclerosis," *Brain a Journal of Neurology*, 2018, 141(6): 1665-1677.
Fan et al., "The emerging role of exosome-derived non-coding RNAs in cancer biology," *Cancer Lett.*, 2018, 414: 107-115.
Goetzl et al., "Altered levels of plasma neuron-derived exosomes and their cargo proteins characterize acute and chronic mild traumatic brain injury," *FASEB Jour.*, 2019, 33(4): 5082-5088.
Goetzl et al., "Traumatic brain injury increases plasma astrocyte-derived exosome levels of neurotoxic complement proteins," *FASEB Jour.*, 2020, 34(2): 3359-3366.
Hamlett et al., "Neuronal exosomes reveal Alzheimer's disease biomarkers in Down syndrome," *Alzheimers Dement.*, 2017, 13(5): 541-549.
Hart et al., "Preclinical assessment of therapeutic antibodies against human CD40 and human interleukin-12/23p40 in a nonhuman primate model of multiple sclerosis," *Neurodegener. Dis.*, 2008, 5(1): 38-52.
Hartung et al., "Diagnosis of multiple sclerosis: revisions of the McDonald criteria 2017—continuity and change," *Curr. Opin. Neurol.*, 2019, 32(3): 327-337.
Kalatha et al., "Glial and neuroaxonal biomarkers in a multiple sclerosis (MS) cohort," *Hell. J. Nucl .Med.*, 2019, 22 Suppl 2: 113-121.
Kutzelnigg et al., "Cortical demyelination and diffuse white matter injury in multiple sclerosis," *Brain a Journal of Neurology*, 2005, 128(Pt 11): 2705-2712.
Ledreux et al., "Assessment of Long-Term Effects of Sports-Related Concussions: Biological Mechanisms and Exosomal Biomarkers," *Front. Neurosci.* 2020, 14: 761.
Ledreux et al., "Small Neuron-Derived Extracellular Vesicles from Individuals with Down Syndrome Propagate Tau Pathology in the Wildtype Mouse Brain," *J. Clin. Med.*, 2021, 10(17): 3931.
Liu et al., "NG2 glia are required for maintaining microglia homeostatic state," *Glia*, 2020, 68(2): 345-355.
Liu et al., "Targeted exosome-mediated delivery of opioid receptor Mu siRNA for the treatment of morphine relapse," *Sci. Rep.*, 2015, 5: 17543.
Macaron et al., "Diagnosis and Management of Progressive Multiple Sclerosis," *Biomedicines*, 2019, 7(56): 23 pages.
Maggi et al., "Chronic White Matter Inflammation and Serum Neurofilament Levels in Multiple Sclerosis," *Neurology* 2021, 97(6): e543-e553.
Najafian et al., "T cell costimulatory pathways: blockade for autoimmunity," *Expert Opin. Biol. Ther.*, 2003, 3(2): 227-236.
Ontaneda., "Progressive Multiple Sclerosis," *Continuum (Minneap Minn)*, 2019, 25(3): 736-752.
Peng et al., "Microglia-Derived Exosomes Improve Spinal Cord Functional Recovery after Injury via Inhibiting Oxidative Stress and Promoting the Survival and Function of Endothelia Cells," *Oxid. Med. Cell Longev.*, 2021, 2021: 1695087.
Pulliam et al., "Plasma neuronal exosomes serve as biomarkers of cognitive impairment in HIV infection and Alzheimer's disease," *J. Neurovirol.*, 2019, 25(5): 702-709.
Ruiz et al., "Resolution of inflammation during multiple sclerosis," *Semin. Immunopathol.*, 2019, 41(6): 711-726.
Santilli et al., "CD40/CD40L system and vascular disease," *Intern. Emerg. Med.*, 2007, 2(4): 256-268.
Schuh et al., "Features of Human CD3+CD20+ T Cells," *J. Immunol.*, 2016, 197(4): 1111-1117.
Sharma et al., "Glioma-derived exosomes drive the differentiation of neural stem cells to astrocytes," *PLOS One* 2020, 15(7): e0234614.
Siracusa et al., "Astrocytes: Role and Functions in Brain Pathologies," *Front. Pharmacol.* 2019, 10: 1114.
Stys et al., "Recent advances in understanding multiple sclerosis," *F1000Res*, 2019, 8: 8 pages.
Sun et al., "Characterization and Biomarker Analyses of Post-COVID-19 Complications and Neurological Manifestations," *Cells*, 2021, 10(386): 17 pages.
Takahashi et al., "The role of extracellular vesicle microRNAs in cancer biology," *Clin. Chem. Lab Med.*, 2017, 55(5): 648-656.
Takeda et al., "Neuronal Differentiation of Human Mesenchymal Stem Cells Using Exosomes Derived from Differentiating Neuronal Cells," *PLOS One*, 2015, 10(8): e0135111.
Thouvenot., "Update on clinically isolated syndrome," *Presse Med.*, 2015, 44(4 Pt 2): e121-136.
Vaitaitis et al., "A CD40 targeting peptide prevents severe symptoms in experimental autoimmune encephalomyelitis," *J. Neuroimmunol.*, 2019, 332: 8-15.
Vaitaitis et al., "Biomarker discovery in pre-Type 1 Diabetes; Th40 cells as a predictive risk factor," *J. Clin. Endocrinol. Metab.*, 2019, 104(9): 4127-4142.
van Kooten et al., "CD40-CD40 ligand," *J. Leukoc. Biol.*, 2000, 67(1): 2-17.
Vaz et al., "Phenotypic Effects of Wild-Type and Mutant SOD1 Expression in N9 Murine Microglia at Steady State, Inflammatory and Immunomodulatory Conditions," *Front. Cell. Neurosci.*, 2019, 13: 109.
Winston et al., "Assessing Neuronal and Astrocyte Derived Exosomes From Individuals With Mild Traumatic Brain Injury for Markers of Neurodegeneration and Cytotoxic Activity," *Front. Neurosci.*, 2019, 13: 1005.
Yu et al., "Reduced oligodendrocyte exosome secretion in multiple system atrophy involves SNARE dysfunction," *Brain a Journal of Neurology,*, 2020, 143(6): 1780-1797.
Extended European Search Report for Application No. EP 20840056.4, dated Jun. 14, 2023.
Partial Supplementary European Search Report for EP Application No. EP 20840056.4 dated Mar. 23, 2023.

* cited by examiner

Fructosamine Serum Values:
Pre-Treatment v. Post-Treatment

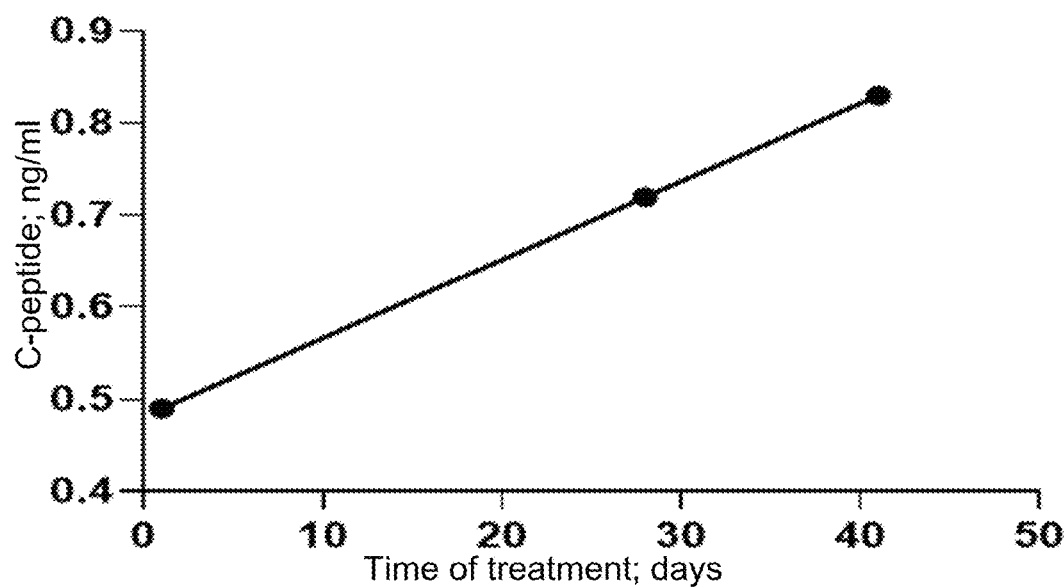
FIG. 14d  Dog #4
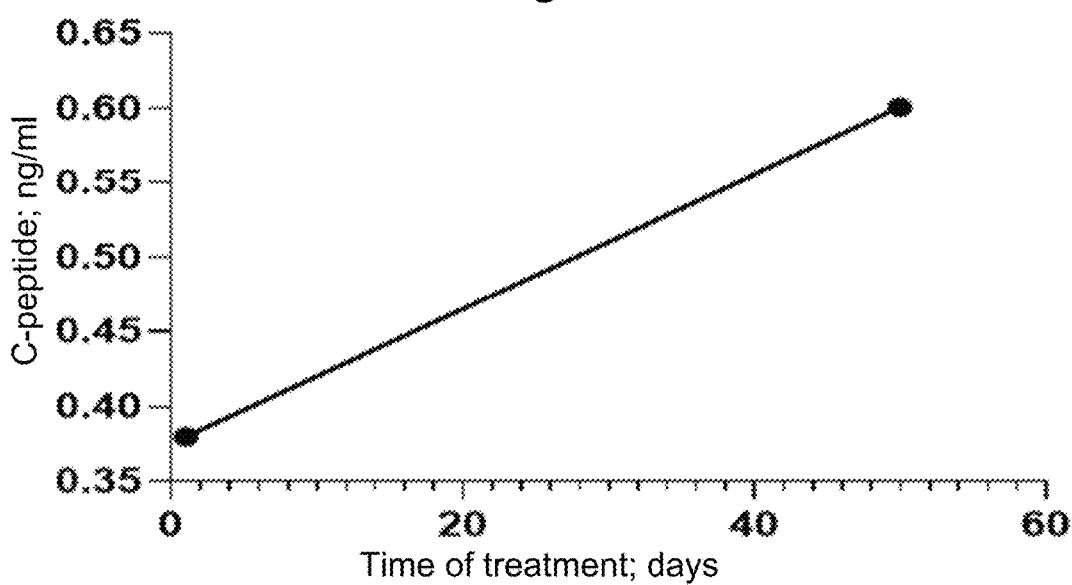
FIG. 14e  Dog #5

Comparison of peripheral Th40 cell Percentages

FIG. 19

Date: 11/12/2019

| Item | Reference |
|---|---|
| PLASMA PROTEIN | 6.0 - 7.5 G/dl |
| HGB 15.7 | 13.0 - 20.0 G/dl |
| HGB (cell) 15.0 | 13 - 20 G/dl |
| HCT 46 | 40 - 55 % |
| RBC 7.11 | 5.5 - 8.5 10^6/ul |
| MCV 64 | 62 - 74 fl |
| RDW 17.0 H | 12 - 15 % |
| MCHC 34 | 33 - 36 G/dl |
| CHCM 33 | 33 - 36 G/dl |
| PLATELETS 797 H | 200 - 500 10^3/ul |
| MPV 12.6 | 7.5 - 14.6 fl |
| NUCLEATED CELLS 9.9 | 4.5 - 15.0 10^3/ul |

CBC-Differential Count

| Item | N | Reference | Percentage |
|---|---|---|---|
| NEUTROPHIL | 7.2 | 2.6 - 11 | 73% |
| LYMPHOCYTE | 1.6 | 1 - 4.8 | 16% |
| MONOCYTE | 0.6 | 0.2 - 1.0 | 6% |
| EOSINOPHIL | 0.5 | 0.1 - 1.2 | 5% |
| NEUTROPHIL | 7.2 | 2.6 – 11.0 10^3/ul | |

Clumped Platelets Few
Hematology:

Date: 11/05/2019

| Item | Reference |
|---|---|
| PLASMA PROTEIN 8.7 H | 6.0 - 7.5 G/dl |
| HGB 16.5 | 13.0 - 20.0 G/dl |
| HGB (cell) 15.9 | 13 - 20 G/dl |
| HCT 49 | 40 - 55 % |
| RBC 7.55 | 5.5 - 8.5 10^6/ul |
| MCV 64 | 62 - 74 fl |
| RDW 17.6 H | 12 - 15 % |
| MCHC 34 | 33 - 36 G/dl |
| CHCM 33 | 33 - 36 G/dl |
| PLATELETS 733 H | 200 - 500 10^3/ul |
| MPV 13.4 | 7.5 - 14.6 fl |
| NUCLEATED CELLS 10.0 | 4.5 - 15.0 10^3/ul |

CBC-Differential Count

| Item | N | Reference | Percentage |
|---|---|---|---|
| NEUTROPHIL | 7.0 | 2.6 - 11 | 70% |
| LYMPHOCYTE | 2.4 | 1 - 4.8 | 24% |
| MONOCYTE | 0.4 | 0.2 - 1.0 | 4% |
| EOSINOPHIL | 0.2 | 0.1 - 1.2 | 2% |
| NEUTROPHIL | 6.8 | 2.6 – 11.0 10^3/ul | |

Clumped Platelets Few
Hematology:

FIG. 20

Date: 11/12/2019

| Item | Reference |
|---|---|
| PLASMA PROTEIN | 6.0 - 7.5 G/dl |
| HGB 17.3 | 13.0 - 20.0 G/dl |
| HGB (cell) 17.3 | 13 - 20 G/dl |
| HCT 49 | 40 - 55 % |
| RBC 7.26 | 5.5 - 8.5 10^6/ul |
| MCV 68 | 62 - 74 fl |
| RDW 14.8 | 12 - 15 % |
| MCHC 35 | 33 - 36 G/dl |
| CHCM 35 | 33 - 36 G/dl |
| PLATELETS 165 L | 200 - 500 10^3/ul |
| MPV 11.9 | 7.5 - 14.6 fl |
| NUCLEATED CELLS 6.6 | 4.5 - 15.0 10^3/ul |

CBC-Differential Count

| Item | N | Reference | Percentage |
|---|---|---|---|
| NEUTROPHIL | 4.4 | 2.6 - 11 | 66% |
| LYMPHOCYTE | 1.5 | 1 - 4.8 | 22% |
| MONOCYTE | 0.2 | 0.2 - 1.0 | 3% |
| EOSINOPHIL | 0.6 | 0.1 - 1.2 | 9% |
| NEUTROPHIL | 4.0 | 2.6 – 11.0 10^3/ul | |

Clumped Platelets Absent
Hematology:

Date: 01/24/2020

| Item | Reference |
|---|---|
| PLASMA PROTEIN - | 6.0 - 7.5 G/dl |
| HGB - | 13.0 - 20.0 G/dl |
| HGB (cell) 16.4 | 13 - 20 G/dl |
| HCT 45 | 40 - 55 % |
| RBC 6.80 | 5.5 - 8.5 10^6/ul |
| MCV 67 | 62 - 74 fl |
| RDW 15.0 | 12 - 15 % |
| MCHC 36 | 33 - 36 G/dl |
| CHCM 36 | 33 - 36 G/dl |
| PLATELETS 135 L | 200 - 500 10^3/ul |
| MPV 11.2 | 7.5 - 14.6 fl |
| NUCLEATED CELLS 4.9 | 4.5 - 15.0 10^3/ul |

CBC-Differential Count

| Item | N | Reference | Percentage |
|---|---|---|---|
| NEUTROPHIL | 3.4 | 2.6 - 11 | 69% |
| LYMPHOCYTE | 1.1 | 1 - 4.8 | 22% |
| MONOCYTE | 0.3 | 0.2 - 1.0 | 6% |
| EOSINOPHIL | 0.1 | 0.1 - 1.2 | 3% |
| NEUTROPHIL | 3.3 | 2.6 – 11.0 10^3/ul | |

Clumped Platelets Absent
Hematology:

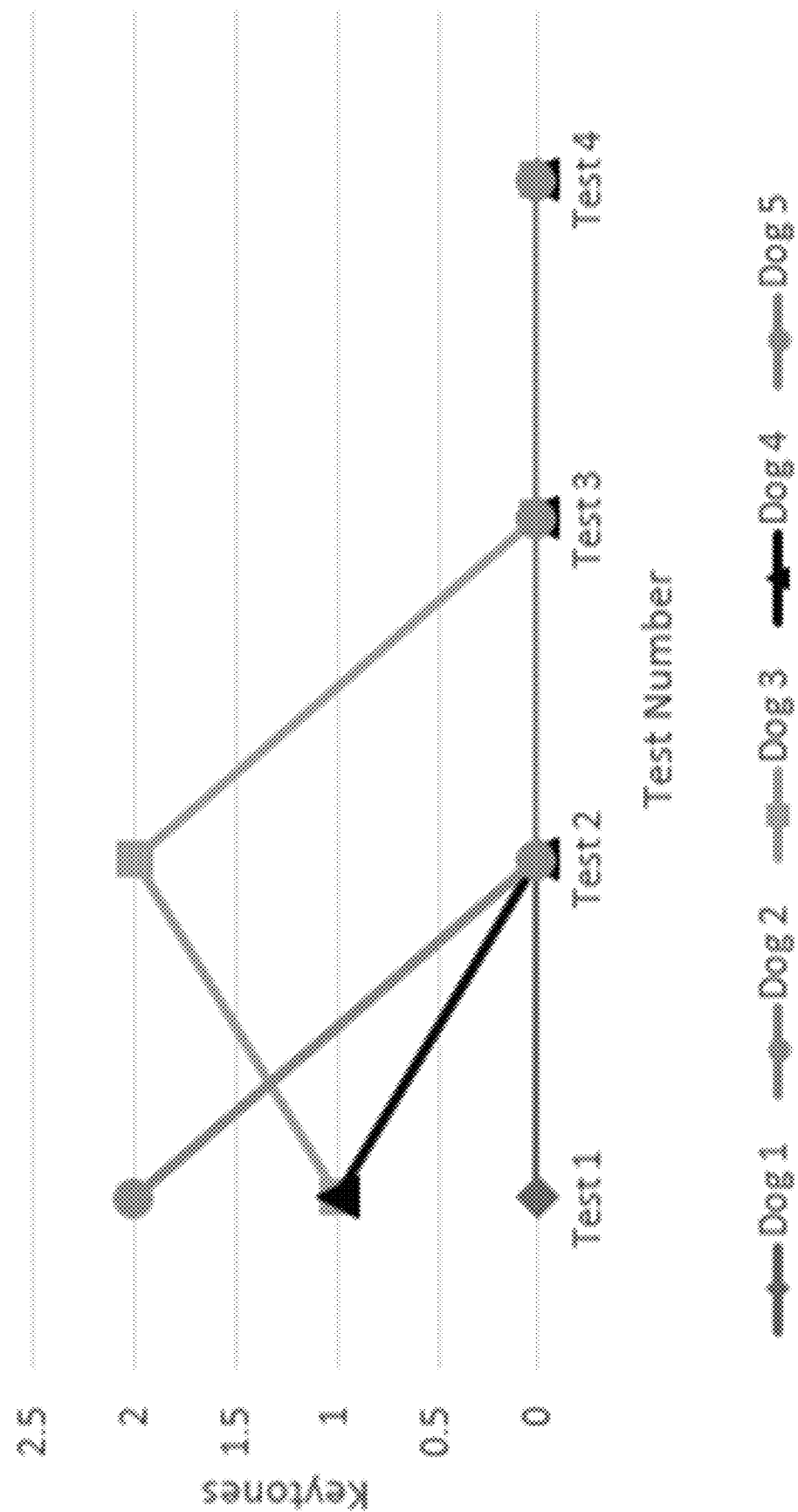

PEPTIDES AND METHODS FOR TREATING DISEASE

SEQUENCE LISTING

The instant application contains a Sequence Listing which has been submitted in ASCII format via EFS-Web and is hereby incorporated by reference in its entirety. Said ASCII copy created on Jul. 11, 2020 is named SOP0_00901WO_Sequence_Listing_ST25.txt and is 33 kilobytes in size.

The present developments relate to peptides and methods and/or uses thereof for prevention, modulation, and treatment of disease in subjects. Further, the present disclosure relates to peptides that affect, interact, and/or inhibit the interaction of the CD40 complex and CD154, and the use of such compounds in modulating T-cell activity and treating disease.

BACKGROUND

Inflammation may occur when inflammatory cells, such as neutrophils, eosinophils, basophils, mast cells, macrophages, platelets, and endothelial cells, respond to inflammatory events or harmful stimuli, such as, invading microorganisms, damages cells, or other irritants. The body's inflammatory response is beneficial because for example, in the case of invading microorganisms, the inflammatory response is an important step in localizing the infecting agent for removal by the immune system. However, in autoimmunity there is no infection, yet severe inflammation is present or persistent. The inflammation in this case, referred to as aseptic chronic inflammation (ACI), is detrimental since it destroys normal tissues. The results of this aseptic inflammation are life-altering and in some cases life-threatening. Moreover, as with acute inflammation, this process is mediated by immune cells, including T-cells.

A major concern for modern medicine is how to control ACI such as that which occurs during autoimmune diseases, as well as how to control acute inflammation resulting from trauma. Inflammation, both chronic and acute, leads to tissue degeneration and eventual loss of function of major organs. ACI is not limited to a single disease, but is instrumental in numerous autoimmune diseases, including, but not limited to: type 1 diabetes (T1D), multiple sclerosis (MS), systemic lupus erythematosus (SLE), rheumatoid arthritis (RA), Crohn's disease, inflammatory bowel disease (IBS), chronic obstructive pulmonary disease (COPD) including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome (ARDS), acute lung injury, and aseptic chronic inflammation (ACI) associated with organ transplantation.

Autoimmune disorders are classified into two types: organ-specific (directed mainly at one organ) and non-organ-specific (widely spread throughout the body). Examples of organ-specific autoimmune disorders are insulin-dependent Type 1 diabetes (T1D) which affects the pancreas; Hashimoto's thyroiditis and Graves' disease, which affect the thyroid gland; pernicious anemia, which affects the blood; Addison's disease, which affects the adrenal glands; chronic active hepatitis, which affects the liver; myasthenia gravis which affects the muscle; and multiple sclerosis (MS), which affects tissue of the nervous system. An example of a non-organ-specific autoimmune disorders is rheumatoid arthritis (RA). Autoimmune diseases are often chronic, debilitating, and life-threatening. The National Institutes of Health (NIH) estimates that up to 23.5 million Americans suffer from autoimmune disease and that the prevalence is rising. It has been estimated that autoimmune diseases are among the ten leading causes of death among women in all age groups up to 65 years.

Acute inflammation, as observed during trauma or sepsis, is also immune cell mediated. While a comprehensive, complete, and exhaustive list of the molecular mediators in this process have not yet been identified, a prominent role for T-cells, lymphocytes, neutrophils, macrophages, monocytes, neutrophils, eosinophils, basophils, mast cells, and other inflammatory cells is strongly implicated. Therefore, a process to modulate these cell types may control the inflammatory response.

It is known that canines, felines, and equine suffer from a variety of autoimmune diseases. Some of these diseases may have molecular drivers that are similar to those of humans, while others may have causes that are quite different, and many are not yet known. In any event, the market for disease therapeutics for companion animals is a growing field and researchers and pet owners, and veterinarians alike are in search of therapies for diseases that afflict these valued and treasured animals.

Diabetes mellitus is one of the most common endocrine diseases that a canine may develop (Catchpole, B., et al., *Diabetologia*, 2005, 48:1948-56). Further, the incidence of canine diabetes mellitus is increasing at substantial rates, with one study showing the incidence increasing from 19 cases per 10,000 dogs in 1970 to 64 cases per 10,000 dogs in 1999 (Gruptill, L., et al., Vet. J., 2003, 165:240-47). The standard of care usually requires that a dog suffering from the disease initially start an insulin therapy, irrespective of the underlying cause and/or the classification of the diabetes (O'Kell, A, et al., *Diabetes*, 2017, 66(6): 1443-52). Currently, cases of canine diabetes are classified into two different types: insulin deficiency diabetes and insulin resistance diabetes (Catchpole, B., et al., *Diabetologia*, 2005, 48:1948-56). It is currently postulated that canines are not susceptible to developing diabetes that is equivalent to human type 2 diabetes; however, it is noted that obesity is associated with insulin resistance diabetes in some cases (Id.).

Most diabetic dogs suffer from insulin deficiency diabetes, where the reason for the disease is loss or destruction of pancreatic β-cells results in the underproduction or complete lack of production of insulin (Id.). The role of autoimmunity is currently less clear in canine diabetes development than that of human T1D and the non-obese diabetic (NOD) mouse development; however, the inflammatory process and autoimmunity is still suspected in at least some cases of the disease (Id.; Matthews, C E., Pediatr. Diabetes, 2005, 6:165-77; Amer. Diabetes Association Diagnosis and Classification of Diabetes Mellitus, *Diabetes Care*, 2014, 37, Suppl.1: S81-S90). Canine diabetes is often diagnosed when hyperglycemia (usually >~250 mg/dL) and glucosuria are identified; however, no single diagnostic indicators, benchmarks, or criteria currently exist (O'Kell, A, et al., *Diabetes*, 2017, 66(6): 1443-52).

Diabetes mellitus is also a common endocrine disease in cats (Gottlieb, S., et al., *Vet. Med.* (*Auckl*), 9:33-42, 2018). The current classification of feline diabetes is based on human diabetes including the mechanisms and causes involved in pancreatic β-cell failure thereof. Thus, it is currently postulated that cats suffer from both type 1 and type 2 diabetes; however, type 1 diabetes is considered less common in felines, than in humans or dogs (Id.).

Horses also suffer from diabetes mellitus and again the model for this disease state is based off what is understood about human diabetes (Johnons, P. J., et al., *J. Diabetes Sci. Tecnol.* 6(3):534-40, 2012). Horses are susceptible to develop equine metabolic syndrome (EMS) which may in turn cause the development of debilitating conditions such as laminitis, which affects the equine hoof (Id.). Development of laminitis sometimes necessitates euthanasia. (Id.) Therefore, a therapy which may improve conditions related to disease and inflammation may be useful to prevent complications in equine subjects that are afflicted with EMS.

The present subject matter is also related to the discovery that a unique subset of T-cells, which express CD40 protein, and thus are referred to as Th40 cells, that may be instrumental in autoimmune inflammation. Moreover, involvement of Th40 cells in the autoimmune process may be dependent on the interaction between CD40 protein expressed on the surface of the T-cell, and CD154 protein. Interaction of CD40 and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction may modulate Th40 cell activity, and thereby affect inflammation.

Thus, there exists a need in the art for safer and more effective methods for treatment and prevention of autoimmune diseases in canines, felines, and equines, including for diabetes mellitus. The present disclosure provides novel bioactive peptides, variants, and derivatives thereof. Moreover, the present developments may address this need by describing peptides and methods for treatment of autoimmune diseases by administration of a therapeutically effective amount of a CD40 peptide. Further, the present developments may provide the added benefit of preventing autoantibody generation, and thus may allow the resumption of normal immune function.

This statement of background is for information purposes only and is not intended to be a complete or exhaustive explication of all potentially relevant background.

SUMMARY

The present developments relate to bioactive peptides and their use in methods for treating subjects before, during, and/or after the development of diabetes mellitus and/or an autoimmune condition. The present developments demonstrate that the peptides hereof may impact inflammatory conditions that are present or concurrent with a number of diseases. The peptides hereof may be used to provide therapeutic results to help control, manage, or impact conditions and diseases that are caused by inflammation, the inflammatory cascade, or autoimmune-autoinflammatory pathways. Thus, the present developments relate to the use of peptides hereof to control one or more of blood glucose, fructosaime serum levels/values, c-peptide levels, and other measured markers of disease, disorders, or inflammation and described and disclosed herein.

These developments may be related to the understanding that the CD40-CD154 inflammatory dyad may play and important role in the development and progression of diabetes mellitus and autoimmune diseases. The present developments also may relate to reducing Th40 cell levels and hyperglycemia. The present developments may also relate to the therapeutic effects of reducing frutcosamine serum values and increasing c-peptide levels.

Thus, this disclosure provides bioactive peptides and methods for their use for preventing, treating, and/or reducing the incidence and/or symptoms of an autoimmune disease or disorder that may result from chronic inflammation, damage to β-cells of the pancreas, and other conditions that are implicated by the CD40-CD154 dyad. The peptides disclosed herein provide variants, homologs, orthologs, and/or other derivatives that may be useful in the treatment of disease. The methods disclosed herein include administering to a subject in need of treatment an effective amount of a peptide that affects, modifies, inhibits, modulates, and/or interacts with CD40. This interaction may be in such a manner as to interfere with CD40 proteins and CD154 proteins binding and interactions. In these methods, the autoimmune disease may include: type 1 diabetes (T1D), multiple sclerosis (MS), systemic lupus erythematosus (SLE), rheumatoid arthritis (RA), Crohn's disease, inflammatory bowel disease (IBS), chronic obstructive pulmonary disease (COPD) including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome (ARDS), acute lung injury, and aseptic chronic inflammation (ACI) associated with organ transplantation.

The peptides hereof also may be used in methods of treating or preventing hyperglycemia in a subject by administering to the subject a composition comprising a peptide of this disclosure, and functional fragments and/or homologs and analogs thereof, in an amount and under conditions effective to decrease hyperglycemia.

The peptides useful in these methods may be a peptide that binds to, interacts with, and/or affects CD40. Further, the peptides hereof may affect or disrupt the interaction of CD40 with CD154. Moreover, in some embodiments, administration of the peptides hereof may reduce the number of Th40 cells in the subject. These short interfering peptides (SIPs) may include an amino acid sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15. The inhibitor peptides may include a modification selected from phosphorylation and glycosylation, and/or may be linked to polyethylene glycol (PEG) molecule, and/or may be linked to one or more domains of an Fc region of mouse, human, canine, feline, or equine, IgG immunoglobin, or the equivalent in each species, and/or may be linked to an epitope tag polypeptide comprising between 6 and 50 amino acid residues. Additionally, the inhibitor peptides hereof may also include modifications of termini such as acetylation and amidation. Additionally, peptides hereof may include several salt forms including hydrochloride salts, acetate salts, TFA salts, and sodium chloride salts.

This Summary is neither intended nor should it be construed as being representative of the full extent and scope of the present disclosure. Further, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the Drawings, Detailed Description, and no limitation as to the scope of the present disclosure is intended by either the inclusion or non-inclusion of elements. Moreover, the materials, method, and examples are illustrative only and are not intended to be limiting, nor should they be construed as limiting the embodiments.

Additional features and aspects of the developments hereof will be apparent from the following detailed description and claims.

BRIEF DESCRIPTION OF THE FIGURES

FIG. 14a, FIG. 14b, FIG. 14c, FIG. 14d, and FIG. 14e provide graphs of c-peptide levels in diabetic dog subjects before, during, and at the end of treatment.

FIG. 19 provides tables of blood counts for a diabetic dog subject, before and during treatment.

FIG. 20 provides tables of blood counts for a diabetic dog subject, before and during treatment.

FIG. 25 provides a graph showing the effect that treatment with SEQ ID NO: 13 had on ketones measured in the urine of the dog subjects.

DETAILED DESCRIPTION

Figure 1:
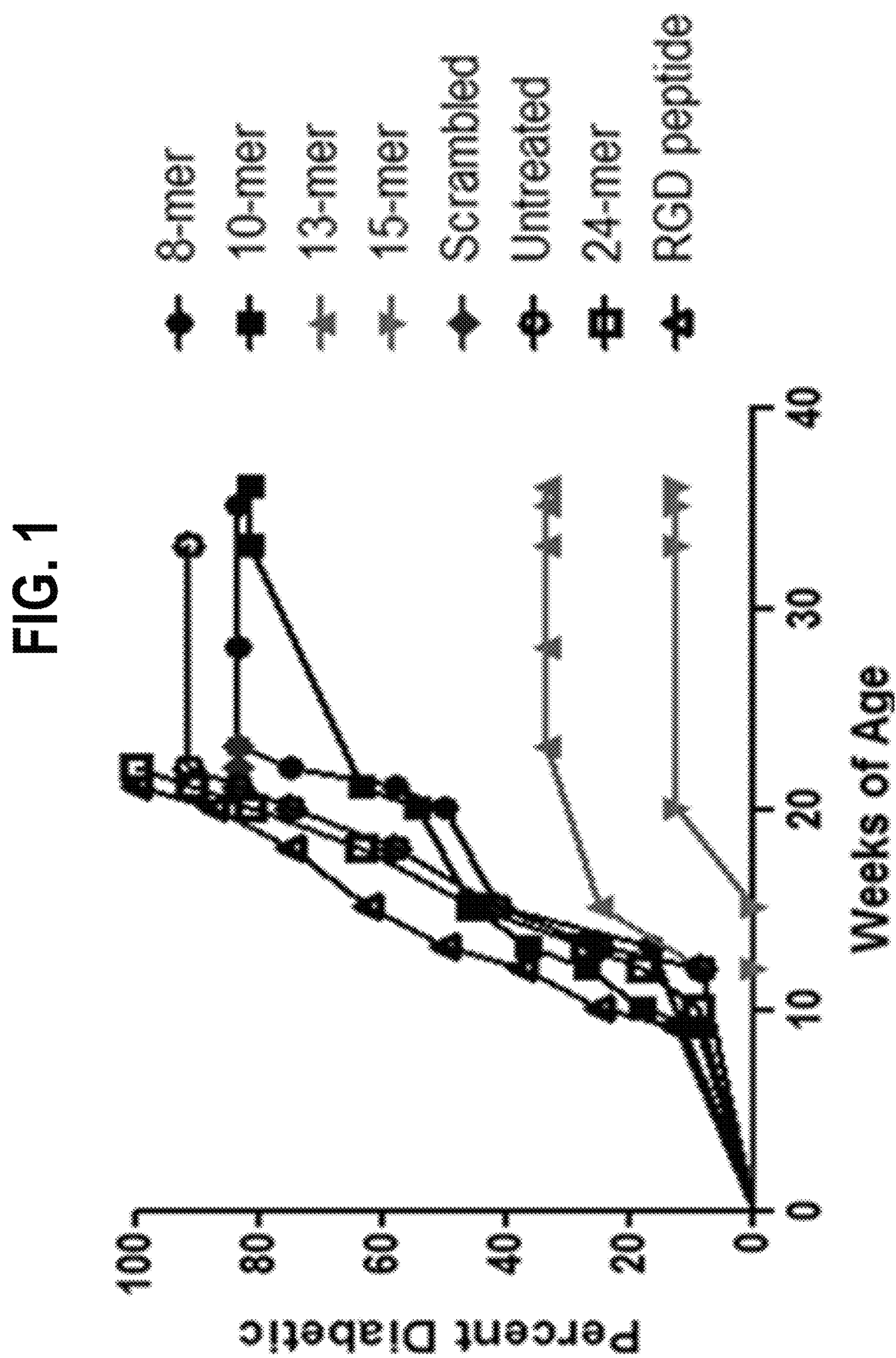
FIG. 1 is a chart of the effect of various peptides of CD154 on the development of diabetes in NOD mice. The 8-mer (SEQ ID NO: 22), 10-mer (SEQ NO: 41), 13-mer (SEQ ID NO:42), 15-mer (SEQ ID NO: 24), and 24-mer (SEQ ID NO:43) were tested.

This disclosure provides bioactive peptides. These peptides are useful for preventing, modulating, and/or treating a variety of indications and diseases, which are discussed in detail below. In some embodiments, the peptides hereof affect the interaction and/or binding of the CD40 complex with its ligand CD154.

The present developments provide novel compositions and methods for treating, modulating, and/or reducing the severity of diabetes in animal subjects. In some instances, diabetes may arise as a result of beta cells being infiltrated and destroyed which in turn results in the loss or reduction of ability to produce insulin. The developments hereof also relate to treatment of these conditions which is demonstrated in results of blood glucose measurements, fructosamine serum values, c-peptide levels, and peripheral Th40 levels. Thus the present developments also relate to methods of treating subjects before, during, and/or after the development of diabetes, with a specific peptide or pharmaceutical composition that may reduce signs and symptoms of diabetes, reduce Th40 levels in the blood, and reduce, modulate, and/or regulate hyperglycemia.

Thus, the developments and implementations disclosed herein and hereof may include compositions of matter and methods of treating and/or reducing the diabetes. These methods include administering to a subject in need of a treatment an effective amount of a peptide to inhibit, interfere, interact, and/or affect the binding or signaling between proteins associated with the CD40 complex, including but not limited to CD154. It should also be appreciated, that the diseases or disorders implicated may also include autoimmune conditions such as type 1 diabetes (T1D), multiple sclerosis (MS), systemic lupus erythematosus (SLE), rheumatoid arthritis (RA), Crohn's disease, inflammatory bowel disease (IBS), chronic obstructive pulmonary disease (COPD) including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome (ARDS), acute lung injury, and aseptic chronic inflammation (ACI) associated with organ transplantation.

The present subject matter is based on the discovery that a unique subset of T-cells, which express CD40 protein, and thus are referred to as Th40 cells, may be instrumental in autoimmune inflammation. Moreover, involvement of Th40 cells in the autoimmune process may be dependent on the interaction between CD40 protein expressed on the surface of the T-cell, and CD154 protein. Interaction of CD40 complex and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction can modulate Th40 cell activity, and thereby affect inflammation. Thus, the present subject matter relates to the peptides, and administration thereof, that may affect the interaction between a CD40 protein and a CD154 protein, thereby modulating inflammation. Moreover, the present subject matter relates to peptides that affect the interaction between CD40 protein expressed on the surface of a T-cell, and a CD154 protein, thereby affecting T-cell activity, controlling inflammation, and consequently preventing, modulating, and reducing diabetes mellitus and/or other autoimmune diseases. The present subject matter also encompasses the use of such peptides to detect Th40 cells.

A unique T cell subset has been shown to be instrumental in the development of autoimmune disease. These cells are phenotypically characterized as CD4loCD40+ (Waid, D. M., et al., *Eur. J. of Immunol.*, 34:1488, 2004; Vaitaitis, G. M., et al., *Cutting Edge, J. Immunol.*, 170:3455, 2003; Wagner, D. H., Jr., et al., *Proc. Nat'l. Acad. Sci. USA,* 99:3782, 2002; Wagner, D. H., Jr., et al., *Int'l J. of Mol. Med.* 4:231, 1999), and are referred to as Th40 cells. (Waid, D. M., et al. (2004) *Eur. J. of Immunol.* 34:1488; Vaitaitis, G. M., et al., *Cutting Edge, J. Immunol.* 170:3455, 2003; Wagner, D. H., Jr., et al., *Proc. Nat'l Acad. Sci. USA* 99:3782, 2002; Wagner, D. H., Jr., et al., *Int'l J. of Mol. Med.* 4:231, 1999). Th40 cells may be any CD4+ T cell that co-expresses CD40 and CD4hi or CD4lo. CD40 expression typically is associated with antigen presenting cells and the majority of prior art describes CD40 as being expressed on B cells, macrophages, monocytes, and other cells; however, CD40 proteins are also expressed on T cells (Waid, D. M., et al., 2004. *Eur. J. of Immunol.*, 34:1488, 2004; Vaitaitis, G. M., et al., *Cutting Edge, J. Immunol.*, 170:3455, 2003; Wagner, D. H., Jr., et al., *Proc. Nat'l Acad. Sci. USA*, 99:3782, 2002; Wagner, D. H., et al., *Int'l. J. of Mol. Med.,* 4:231, 1999; Bourgeois, C., et al., *Science,* 297:2060, 2002; Fanslow, W. C., et al., *J. of Immun.,* 152:4262, 1994; Ramsdell, F., et al., *J. of Immunol.* 152:2190, 1994; Grabstein, K. H., et al., *J. of Immunol.,* 150:3141, 1993; Armitage, R. J., et al., *Sem. in Immun.,* 5:401, 1993; Cooper, C. J., et al., *J of Immunol.,* 173:6532, 2004). While Th40 cells comprise a proportion of the peripheral CD4+ compartment in naive, non-autoimmune mice (Waid, D. M., et al., *Eur. J. of Immunol.,* 34:1488, 2004; Wagner, D. H., Jr., et al., *Int_3 l J. of Mol. Med.,* 4:231, 1999), and in humans (Waid. D. M., et al., *Clin. Immunol.* 124:138, 2007), this proportion is drastically expanded to as much as 50% of the CD4+ _9 compartment in autoimmune prone mice (Waid, D. M., et al., *Eur. J. of Immunol.* 34:1488, 2004; Wagner, D. H., Jr., et al., *Proc. Nat'l Acad. Sci. USA* 99:3782, 2002; Wagner, D. H., et al., *Int'l J. of Mol. Med.,* 4:231, 1999) and humans (Waid, D. M., et al., *Eur. J. of Immunol.* 34:1488, 2004; Waid. D. M., et al., *Clin. Immunol.* 124:138, 2007). These T cells do not express early activation markers and occur in the naive phenotype of non-challenged mice.

In NOD (non-obese diabetic) mice, Th40 cells occur at exaggerated levels in spleen, lymph nodes and the pancreas, even prior to diabetes onset (Waid, D. M., et al., *Eur. J. of Immunol.* 34:1488, 2004; Wagner, D. H., Jr., et al., *Proc. Nat'l Acad. Sci. USA* 99:3782, 2002). An elevated number and percentage of these T cells are seen in peripheral blood of type 1 diabetic (T1D) patients when compared to non-autoimmune controls and type 2 diabetic patients (Waid. D. M., et al., *Clin. Immunol.,* 124:138, 2007).

The observed increase in Th40 cells could mean that those T cells are antigen responsive or that CD40 expression is activation induced. Furthermore, several diabetogenic T cell clones are CD40+ (Wagner, D. H., Jr., et al., *Proc. Nat'l Acad. Sci. USA* 99:3782, 2002). Purified primary Th40 cells from NOD mice and from pre-diabetic NOD (12-weeks of age) mice successfully transfer type 1 diabetes to NOD/scid (Non-Obese Diabetic/Severe Combined Immunodeficiency) recipient mice, directly demonstrating pathogenicity of the Th40 T cell subset (Waid, D. M., et al., *Eur. J. of Immunol.* 34:1488, 2004; Wagner, D. H., Jr., et al., 2002. *Proc. Nat'l Acad. Sci. USA,* 99:3782, 2002). It has been shown that Th40 cells infiltrate islet beta cells destroying insulin production thus suggesting islet antigen specificity (Waid, D. M., et al., *Eur. J. of Immunol.* 34:1488, 2004; Wagner, D. H., Jr., et al., *Proc. Nat'l Acad. Sci. USA* 99:3782, 2002). It has also been shown that Th40 cells are required for diabetes transfer. Peripheral (spleen and regional lymph node) T cells that were CD40 depleted, then CD25, Treg, depleted were not capable of transferring diabetes to Scid (Severe Combined Immunodeficiency) recipients. Even though Treg cells were removed, if the auto-aggressive CD40+ T cells subset is absent, disease transfer does not occur.

While Th40 cells are important in the development of autoimmunity, another important factor is expression of the CD40-Ligand, CD154. CD154 is temporally induced on activated T-cells in response to CD3/TCR stimulation (Lederman, S. et al., *J. of Exp. Med.,* 175:1091, 1992). CD154 expression has also been demonstrated on platelets, monocytes, basophils, eosinophils, dendritic cells, fibroblasts, smooth muscle, and endothelial cells (Russo, S. et al., *J. Immunol.* 171:5489, 2003; Stumpf, C., et al., *Eur. J. Heart Fail.,* 5:629, 2003; Schonbeck, U., et al., *Cell Mol. Life Sci.* 58:4, 2001). CD154 is a member of the tumor necrosis factor (TNF) super-family and a soluble form of CD154 (sCD154) has been described (Russo, S., et al., *J. Immunol.* 171:5489 2003; Stumpf, C., et al., *Eur. J. Heart Fail* 5:629, 2003; Toubi, E., et al., *Autoimmunity* 37:457, 2004). Therefore, sCD154 may act like a cytokine (Stumpf, C., et al., *Eur. J. Heart Fail.* 5:629, 2003). Even though CD154 has not been genetically linked in T1D studies, sCD154 is significantly elevated in T1D and may play a role in the disease process (Varo, N. et al., *Circulation* 107:2664, 2003; Cipollone, F., et al., *Diabetologia* 48:1216, 2005; Devaraj, S., et al., *Diabetes* 55:774, 2006). The importance of CD40-CD154 interaction in autoimmunity has been established (Wagner, D. H., Jr., et al., *Proc. Nat'l Acad. Sci. USA* 99:3782, 2002; Kobata, T., et al., *Rev. Immunogenet.* 2:74, 2000; Homann, D., et al., *Immunity* 16:403, 2002; Goodnow, C. C., et al., *Lancet* 357:2115, 2001; Balasa, B., et al., *J. of Immunol.* 159:4620, 1997). Blocking CD40-CD154 interaction may prevent collagen induced arthritis, (Durie, F. H., et al., *Science* 281:1328, 1993) experimental autoimmune encephalitis (Howard, L. M., et al., *Autoimmunity* 37:411, 2004), prostatitis (Grossman, M. E., et al., *J. Immunother.* 24:237, 2001), and type-1 diabetes in the NOD mouse model (Durie, F. H. et al., *Science* 281:1328, 1993; Balasa, B. et al., *Journal of Immunology* 159:4620, 1997; Howard, L. M., et al., *Autoimmunity* 37:411, 2004; Grossman, M. E. et al., *J. Immunother.* 24:237, 2001). In the diabetes model, it was essential to administer a CD154 blocking antibody to NOD mice at 3-weeks of age because at 9-weeks, blocking antibodies had no effect on diabetes prevention (Balasa, B. et al., *J. of Immunol.* 159:4620, 1997).

Previous work has also demonstrated that the Th40 cell subset induces RAG1 and RAG2 (Recombination-Activating Genes) transcription, translation and nuclear translocation (Vaitaitis, G. M., et al., *Cutting Edge, J. Immunol.* 170:3455, 2003) when CD40 is engaged (Vaitaitis, G. M. et al., *Cutting Edge, J. Immunol.* 170:3455, 2003). CD3 engagement does not induce RAG1 or RAG2 in T-cells (Vaitaitis, G. M., et al., *Cutting Edge, J. Immunol.* 170:3455, 2003). Subsequent to RAG1/RAG2 induction, CD40-mediated T-cell receptor (TCR) revision occurs in peripheral T cells (Vaitaitis, G. M. et al., *Cutting Edge, J. Immunol.* 170:3455, 2003). CD40 induction of TCR revision is RAG dependent. T cells isolated from a TCR-Tg mouse undergo TCR revision when CD40 engaged, but T-cells from the TCR-Tg.RAG−/− mouse do not TCR revise when CD40 engaged (Wagner, D. H., Jr. et al., *Int'l J. of Mol. Med.* 4:231, 1999).

CD40 is a 50-kDa integral membrane protein of the tumor necrosis factor receptor (TNF-R) family. It is constitutively expressed as a homotrimer (Foy T M, et al., *Ann. Rev. of Immunol.*, 14:591, 1996). In general, stimulation of all CD40-expressing cell types induces operations which contribute to inflammation, such as enhancement of costimulatory and adhesion molecules, and up-regulation of proteolytic enzymes (Mach, F. et al., *Atherosclerosis*. 137 Suppl: S89-95, 1998).

CD40's ligand—CD154—is a 39-kDa protein that belongs to the tumor necrosis factor (TNF) family. CD40 forms a trimer that binds CD154 at the interface of the three monomers. CD154 is expressed commonly on cells beyond the surface-expressed CD154, as CD154 may also exist in a soluble biologically active form (sCD154) that is shed from the cell surface after activation. The main source of sCD154 is platelets. (Foy T M, et al., *Ann. Rev. of Immunol.*, 14:591, 1996).

Genetically manipulated mouse models, including models such as the NOD mouse, are utilized for research and development concerning autoimmune diseases including diabetes because the NOD mouse spontaneously develops T1D. Prior studies in humans and mice have attempted to block the CD40/CD154 interaction by using monoclonal antibodies and this approach has proven efficacious in several mouse model studies and in several human studies; however, the use of monoclonal antibodies to target the CD40/CD154 dyad was abandoned due to thromboembolic events which may have been related to the functioning of CD154 in thrombus stabilization. It is postulated that CD154 stabilize thrombi by interaction with the integrin $\alpha_{IIb}\beta_3$, and by inhibiting CD154, thrombi may be less stable, and as a consequence shed emboli causing thrombotic events.

Multiple treatment options have been put forward to address and control both chronic and acute inflammation. Many approaches use non-steroidal anti-inflammatory drugs (NSAIDs) that attack the production of leukotrienes and prostaglandins, cellular products that cause localized inflammation. Other approaches use more powerful immunosuppressant drugs such as cyclophosphamide, methotrexate and azathioprine that suppress the immune response and stop the progression of the disease. Still other treatments involve the use of monoclonal antibodies (mAb) designed to alter the immune responses to self-tissues, as occurs during autoimmune diseases. However, all of these treatments often may have severe, long-term side effects.

Current immune-modulatory therapies may rely upon monoclonal antibody treatments that may give rise to complications. For example, antibodies administered to a subject may cross-react with unintended targets and cause severe nephritic complications and those that specifically act against CD154 may cause embolic complications. Further, the CD40-CD154 interaction may play an important role in antibody generation which may indicate that administration of a monoclonal antibody could induce auto-antibody generation and further complications, which may inhibit the restoration of normal immune function (see generally Banchereau, J. et al., *Annu. Rev. of Immunol.* 12:881, 1994).

Before the present development is further described, it is to be understood that developments hereof are not strictly limited to particular embodiments described, as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the developments, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Furthermore, as used herein the term animal refers to a vertebrate, preferably a mammal. Suitable mammals on which to use the methods of the present invention include but are not limited farm animals, sports animals, pets, primates, mice, rats, horses, dogs, cats, and humans. The term animal can be used interchangeably with the terms subject or patient.

One embodiment of the present subject matter is a peptide that interacts with a CD40 protein in such a manner as to prevent diabetes mellitus and/or autoimmune disease. As used herein, the terms interact, interaction, and the like, mean that two molecules come into sufficient physical proximity such that they cause a modulation of inflammation. One such type of interaction is a binding interaction. In such an interaction the peptide associates with CD40 to form a complex. An example of complex formation is the association of an antigen with an antibody. According to the present subject matter, binding of a peptide hereof to a CD40 protein can be reversible (e.g., non-covalent binding interactions) or non-reversible (e.g., covalent binding interactions). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). Preferred peptides of the present invention are those that bind to a CD40 protein with a Kd of no more than about $1\times10^{-6}$ M, about $1\times10^{-7}$ M, or about $1\times10^{-8}$ M. Particularly preferred peptides are those having a Kd of less than about $1\times10^{-9}$ M. In one embodiment, a peptide hereof binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art.

As used herein, to modulate inflammation means to modify or affect the interaction between CD40 and/or CD40 complex and/or modify or affect inflammation more generally. As used herein, the terms level, number, count and concentration can be used interchangeably. Modulation of inflammation may result in an increase or decrease in the number of Th40 cells present in the inflammatory environment. Consequently, modulation can be referred to as positive or negative. Positive modulation (also referred to as up-regulation) of inflammation may refer to an increase in the number of Th40 cells in the inflammatory environment. Negative modulation (also referred to as down-regulation) of inflammation may refer to a reduction in the number of Th40 cells present in the inflammatory environment. A preferred peptide is one that down-regulates inflammation, and thereby may reduce the number of Th40 cells present in the inflammatory environment. Positive and negative modulation of inflammation may or may not result in a change in the type and amount of immunoregulatory molecules present in the inflammatory environment.

It will be appreciated by those skilled in the art that both a cell culture system and the immune system of an animal comprise basal levels of immune cells and immunoregulatory molecules. The phrases basal level and normal level can be used interchangeably. With regard to the immune system of an animal, as used herein, the basal level of a type of immune cell (e.g., Th40 cell), or a immunoregulatory molecule, refers to the average number of that cell type, or immunoregulatory molecule, present in a population of individuals considered healthy (i.e., free of metabolic, autoimmune, or infectious disease). With regard to a cell culture system, as used herein, the basal level of a type of immune cell, or an immunoregulatory molecule, refers to the average level of that cell type, or immunoregulatory molecule, present in a population of cells that is non-activated. Those skilled in the art are capable of determining if a T-cell, or a population of such cells, is activated. For example, in some instances the expression of CD69, CD25 and/or CD154 proteins by a cell indicates that the cell has been activated.

The basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Variability in this measurement can result from differences in the method used to determine the cell count. Furthermore, normal levels of cells can also be reported as a percentage of a total cell population. For example, in a healthy individual, Th40 cells may make up less than 25% of the total T cell population. Thus, as used herein, the term inflammation may refer to an inflammatory environment in which Th40 cells make up greater than about 25%, greater than about 30%, greater than about 35%, greater than about 40%, greater than about 45%, greater than about 50%, greater than about 55%, greater than about 60%, greater than about 65%, greater than about 70%, greater than about 75%, or greater than about 80% of the total T-cell population. Moreover, a preferred peptide herein is one that may reduce the level of Th40 cells to less than about 50%, less than about 45%, less than about 40%, less than about 35%, less than about 30%, less than about 27%, or equal to about 25% of the total T-cell population. Methods of measuring different types of T-cells in the T-cell population are known to those skilled in the art. Furthermore, a novel method for detecting Th40 cells using peptides hereof is disclosed herein.

As used herein, the phrase inflammatory environment refers to the overall population of immune cells, and related immunoregulatory molecules, that are present in a culture of cells, or in the body of an animal. As such, the phrase inflammatory environment encompasses the types, and/or the relative amounts of immune cells and immunoregulatory molecules (e.g., cytokines) present in a culture of cells, or in an animal, which are involved in affecting an inflammatory reaction. Examples of cells encompassed by the term inflammatory environment include, but are not limited to, T cells, neutrophils, macrophages, granulocytes, and the like. The inflammatory environment relates to cells and molecules that mediate both acute and chronic inflammation. It will be appreciated by those skilled in the art that the inflammatory environment refers to the system to which peptides hereof are administered. In one embodiment, the system is a cell culture system. In one embodiment, the system is a whole animal.

A preferred peptide hereof is one that selectively interacts with a CD40 protein in solution, as determined using an assay such as an immunosorbent assay, or on the surface of a T-cell. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one embodiment, an assay can be performed using cells in culture, or it can be performed in a whole animal. Assays can be designed to give qualitative, quantitative or semi-quantitative results, depending on how they are used and the type of result that is desired.

One embodiment hereof is a peptide that interacts with a CD40 protein in such a manner as to affect the interaction of the CD40 protein with a CD154 protein. The effect of the peptide on the CD40/CD154 interaction can be positive or it can be negative. For example, the peptide may interact with the CD40 protein in such a manner that the strength of the interaction between the CD40 protein and a CD154 protein is increased. Alternatively, the peptide may interact with the CD40 protein such that the strength of the interaction between the CD40 protein and a CD154 protein is decreased. Methods of measuring the strength of binding between the peptide and a CD40 protein are known to those skilled in the art. A preferred peptide hereof is one that reduces the strength of the interaction between a CD40 protein and a CD154 protein. Preferred peptides hereof may reduce the strength of binding between a CD40 protein and a CD154 protein by at least 10%, at least 20%, at least 30%, at least 40%, at least 50%, at least 60%, at least 70%, at least 80%, at least 90%, or at least 95%. A particularly preferred peptide is one that completely inhibits binding of CD40 to CD154. Complete inhibition of binding between CD40 and CD154 means that when a peptide hereof is brought into proximity with a CD40 protein and a CD154 protein under conditions that would normally allow the interaction of CD40 and CD154, no such interaction occurs and activation signals are not stimulated in the CD40-expressing cell. Consequently CD40/CD154 mediated modulation of inflammation does not occur. In one embodiment, the peptide interacts with the CD40 protein in such a manner as to reduce the level of inflammation in the system. In one embodiment, the peptide interacts with the CD40 protein in such a manner as to inhibit the development of inflammation in the system.

While peptides hereof may interact with any site on the CD40 protein, preferred peptides interact with the CD40 protein at a location that overlaps with the CD154 binding site. In one embodiment, a peptide hereof interacts with the CD40 protein at the CD154 binding site. An example of such a peptide is a CD40 ligand competitive antagonist. As used herein, peptides that interfere with, or inhibit, the binding of a CD154 protein to a CD40 protein are referred to as small interfering peptides (SIPs). As used herein a small interfering peptide is a peptide that, through physio-chemical properties, interferes with the interaction of a CD40 protein with a CD154 protein, thereby preventing activation signals from being delivered to the CD40-bearing cell, thus limiting the activation of the CD40-bearing cell, and consequently, inflammation. As demonstrated herein, the consequences of such interference are prevention of T-cell activation and propagation, and a prevention or reduction of inflammation. As demonstrated herein, in some instances the results of such inhibition or prevention of interaction between CD40 and CD154 may include observable data that demonstrates that diabetes mellitus, and characteristics of diseases associated therewith, are prevented, modulated, and/or reduced.

Additionally, a small interfering peptide, may, through its physio-chemical properties, interfere with the interaction of a CD40 protein with a CD154 protein, thereby preventing activation signals from being delivered to the CD40-bearing cell, thus limiting the activation of the CD40-bearing cell, and consequently, modulating, inhibiting, and preventing diabetes mellitus and/or autoimmune disease. As demonstrated herein, the consequences of such interference are prevention of T cell activation and propagation, and a prevention, reduction, or modulation of diabetes mellitus related developments.

The peptides hereof may also be modified to contain, conjugated to, and/or administered with phosphorus, sulfur, manganese, magnesium, calcium, halogens, metals, etc. Amino acid mimics may be used to produce polypeptides, and therefore, the polypeptides of this disclosure may include amino acids mimics that have enhanced properties, such as resistance to degradation.

In the methods disclosed herein, the bioactive peptide may be administered via intramuscular (IM) delivery, intravenous (IV) delivery, subcutaneous (SC) delivery, oral delivery, gavage delivery, emollient/skin delivery, transdermal patch, and/or intranasally.

The peptides and methods hereof may also comprise administering pro-drugs that metabolize to an active form of these peptides. As used herein, a "pro-drug" is a compound that a biological system metabolizes to an active compound as a result of spontaneous chemical reaction(s), enzyme catalyzed reaction(s), and/or metabolic chemical reaction(s), or a combination of each. Standard prodrugs are formed using groups attached to functionality, e.g. HO—, HS—, HOOC—, R2N—, associated with the drug, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines, where the group attached is an acyl group, an alkoxycarbonyl, aminocarbonyl, phosphate or sulfate. The groups illustrated are exemplary and not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved bioavailability, pharmacodynamic half-life, etc.

The methods hereof may include the treatment of a subject developing diabetes mellitus, suspected of developing diabetes mellitus, or likely to develop diabetes mellitus, in order to decrease or prevent complications and problems associated with developing diabetes mellitus and/or autoimmune diseases. In these methods, the blood glucose levels of the subject may be reduced to less than 160 mg/dl, less than 150 mg/dl, less than 140 mg/dl, less than 130 mg/dl, less than 120 mg/dl, or less than 110 mg/dl.

The methods are not limited to use to only type 1 diabetes mellitus, as these methods may be used to treat hyperglycemia resulting from any condition.

When administered or co-administered, the compounds of the present developments are given in a therapeutically effective amount to the subject. As used herein, the phrase "therapeutically effective amount" means an amount that has any beneficial effect in treating the condition, disease, or symptoms, or preventing or reducing the development of disease, condition, syndromes, or disorders. Determining the therapeutically effective amount of the bioactive peptide to administer of the current developments is a matter of optimization and titration in the art and may vary depending on such factors as, but not limited to, the degree of progression or extent of the disease, condition, syndrome, or disorder to be treated, the age and condition of the subject, the weight and surface area of the subject, and other such ascertainable traits that may be pertinent and relevant to the treatment of the subject.

The present developments provide novel bioactive peptides, variants, homologs, orthologs, and/or derivates thereof related to peptides as disclosed herein. The sequences of some of such peptides are shown below in Table 1.

TABLE 1

| SEQ ID NO | SEQUENCE | Description | Length |
|---|---|---|---|
| 1 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ TAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GFSSFGLLKL | SwissPro 27548.2 *Mus musculus* (Mouse) CD40 Ligand (CD154 Protein) | 260 |
| 2 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEETKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 *Homo sapien* (Human) CD40 Ligand (CD154 Protein) | 261 |
| 3 | MIETYSQTAP RSVATGPPVS MKIFMYLLTV FLITQMIGSA LFAVYLHRRL DKIEDERNLY EDFVFMKTLQ KCNKGEGSLS LLNCEEIKSQ FEAFLKEIML NNEMKKEENI AMQKGDQDPR IAAHVISEAS SNPASVLRWA PKGYYTISSN LVSLENGKQL AVKRQGLYYV YAQVTFCSNR AASSQAPFVA SLCLHSPSGT ERVLLRAASS RGSSKPCGQQ SIHLGGVFEL HPGASVFVNV TDPSQVSHGT GFTSFGLLKL | SwissPro O97626 *Canis lupus familiaris* (Dog) CD40 Ligand (CD154 Protein) | 260 |
| 4 | MIETYSQTAP RSVAPGPPVS MKIFMYLLTV FLITQMIGSA LFAVYLHRRL DKIEDERNLY EDFVFMKTLQ KCNKGEGALS LLNCEEIKSR FEAFLKEIML NKETKKEKNV AMQKGDQDPR VAAHVISEAS SSTASVLQWA PKGYYTISSN LVTLENGKQL AVKRQGLYYI YAQVTFCSNR EASSQAPFIA SLCLHSPSGS ERVLLRAANA RSSSKPCGQQ SIHLGGVFEL HPGASVFVNV TDPSQVSHGT GFTSFGLLKL | SwissPro O97605 *Felis catus* (Cat) CD40 Ligand (CD154 Protein) | 260 |
| 5 | MIETYSQPSP RSVATGPPVS MKIFMYLLTV FLITQMIVSA LFAVYLHRRL DKIEDERNLH EDFVFMKTIQ RCNKGEGPLS LLNCEEIRSQ FEGFVKDIML NEEVKKKGEN FEMQKGDQEP QIAAHVISEA SSKTASVLQW AQKGYYTISN NLVTLENGKQ LAVKRQGLYY IYAQVTFCSN REASGQAPFI ASLCLRSVSG SERILLRAAN THSSSKPCGQ QSIHLGGVFE LQPGASVFVN VTDPSQVSHG TGFTSFGLLK L | SwissPro F7AR26-1 *Equus caballus* (Horse) CD40 Ligand (CD154 Protein) | 261 |
| 6 | KGYY | Core-sequence | 4 |
| 7 | KKGYYT | 6-mer-Form 1 | 6 |
| 8 | EKGYYT | 6-mer-Form 2 | 6 |
| 9 | PKGYYT | 6-mer-Form 3 | 6 |
| 10 | QKGYYT | 6-mer-Form 4 | 6 |
| 11 | VLQWA KKGYY TMKSN | 15-mer-Form 1 | 15 |
| 12 | VLQWA EKGYY TMSNN | 15-mer-Form 2 | 15 |
| 13 | VLRWA PKGYY TISSN | 15-mer-Form 3 | 15 |
| 14 | VLQWA PKGYY TISSN | 15-mer-Form 4 | 15 |
| 15 | VLQWA QKGYY TISNN | 15-mer-Form 5 | 15 |
| 16 | NAASV LQWAK KGYYT MKSNL VMLE | 24-mer | 24 |
| 17 | YKNVKQMAYWLTGKS | Scrambled peptide | 15 |

In one aspect, the developments feature peptides of 6 amino acids in length, wherein the peptide comprises the amino acid sequence of Formula I:

$$X^1—X^2—X^3—X^4—X^5—X^6$$

Wherein, $X^1$ is K, E, P, or Q or a small naturally or non-naturally occurring amino acid;

$X^2$ is K or a small naturally or non-naturally occurring amino acid;

$X^3$ is G or a small naturally or non-naturally occurring amino acid;

$X^4$ is Y;

$X^5$ is Y;

$X^6$ is T.

In some embodiments, the amino acid sequence of said peptides differs by at least one, or at least two, or at least three amino acids as compared to the amino acid sequences set forth in SEQ ID NOs: 7-10.

In another aspect, the developments feature peptides of 15 amino acids in length, wherein the peptide comprises the amino acid sequence of Formula II:

$$X^1—X^2—X^3—X^4—X^5—X^6—X^7—X^8—X^9—X^{10}—X^{11}—X^{12}—X^{13}—X^{14}—X^{15} \text{ (SEQ ID NO: 53)}$$

Wherein, $X^1$ is V;

$X^2$ is L;

$X^3$ is Q or R;

$X^4$ is W;

$X^5$ is A;

$X^6$ is K, E, P, or Q;

X7 is K;

$X^8$ is G;

$X^9$ is Y;

$X^{10}$ is Y;

X11 is T;

$X^{12}$ is M or I;

$X^{13}$ is K or S;

$X^{14}$ is S or N;

$X^{15}$ is N.

In some embodiments, the amino acid sequence of said peptides differs by at least one, or at least two, or at least three amino acids as compared to the amino acid sequence set forth in SEQ ID Nos: 11-15.

The present developments provide additional novel bioactive peptides, variants, homologs, orthologs, and/or derivates thereof related to peptides as disclosed herein. The sequences of such peptides are shown below in Table 2.

TABLE 2

| SEQ ID NO | SEQUENCE | Description | Length |
|---|---|---|---|
| 18 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ IAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GFSSFGLLKL | SwissPro 27548.2 Mouse CD40 Ligand (CD154 Protein) | 260 |
| 19 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEETKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CD40 Ligand (CD154 Protein) | 261 |
| 20 | KGYY | Core-sequence | 4 |
| 21 | KKGYYT | 6-mer | 6 |
| 22 | AKKGYYTM | 8-mer-Form 1 | 8 |
| 23 | AEKGYYTM | 8-mer-Form 2 | 8 |
| 24 | VLQWAKKGYYTMKSN | 15-mer-Form 1 | 15 |
| 25 | VLQWAEKGYYTMSNN | 15-mer-Form 2 | 15 |
| 26 | NAASVLQWAKKGYYTMKSNLVMLE | 24-mer | 24 |
| 27 | ISQAVHAAHAEINEAGR | 15-mer from ovalbumin; control peptide | 15 |
| 28 | G-L-Q-W-A-K-K-G-Y-Y-T-M-K-S-N | Gly-1 | 15 |
| 29 | V-G-Q-W-A-K-K-G-Y-Y-T-M-K-S-N | Gly-2 | 15 |

TABLE 2-continued

| SEQ ID NO | SEQUENCE | Description | Length |
|---|---|---|---|
| 30 | V-L-G-W-A-K-K-G-Y-Y-T-M-K-S-N | Gly-3 | 15 |
| 31 | V-L-Q-G-A-K-K-G-Y-Y-T-M-K-S-N | Gly-4 | 15 |
| 32 | V-L-Q-W-G-K-K-G-Y-Y-T-M-K-S-N | Gly-5 | 15 |
| 33 | V-L-Q-W-A-G-K-G-Y-Y-T-M-K-S-N | Gly-6 | 15 |
| 34 | V-L-Q-W-A-K-G-G-Y-Y-T-M-K-S-N | Gly-7 | 15 |
| 35 | V-L-Q-W-A-K-K-G-G-Y-T-M-K-S-N | Gly-8 | 15 |
| 36 | V-L-Q-W-A-K-K-G-Y-G-T-M-K-S-N | Gly-9 | 15 |
| 37 | V-L-Q-W-A-K-K-G-Y-Y-G-M-K-S-N | Gly-10 | 15 |
| 38 | V-L-Q-W-A-K-K-G-Y-Y-T-G-K-S-N | Gly-11 | 15 |
| 39 | ISQAVHAAHAEINEAGR | 15-mer from ovalbumin; control peptide | 15 |
| 40 | YVQGKANLKSKLMYT | Scrambled peptide | 15 |
| 41 | WAKKGYYTMK | 10-mer Form 1 | 10 |
| 42 | VLQWAKKGYYTMK | 13-mer Form 1 | 13 |
| 43 | AASVLQWAKKGYYTMKSNLVMLEN | 24-mer Form 1 | 24 |
| 44 | KGYYTM | 6-mer (Form 2) | 6 |
| 45 | AEKGYY | 6-mer (Form 3) | 6 |
| 46 | AKKGYY | 6-mer (Form 4) | 6 |
| 47 | AKGYYT | 6-mer (Form 5) | 6 |
| 48 | AASVLQWAKKGYYTMKSNLVMLEN | 24-mer-mouse (Form 2) | 24 |
| 49 | YKNVKQMAYWLTGKS | Scrambled peptide | 15 |
| 50 | APKGYY | 6-mer (Form 6) | 6 |
| 51 | AQKGYY | 6-mer (Form 7) | 6 |
| 52 | KGYYTI | 6-mer (Form 8) | 6 |

In some embodiments, the peptides disclosed herein may be peptides that bind to CD40 and/or the CD40 complex. Further, the peptides hereof may be short interfering peptides and may disrupt, affect, or alter the interaction of CD40 with CD154.

In some embodiments, the peptide is isolated from a protein recombinantly produced in a cell. The cell used for recombinant production may be a prokaryotic cell or a eukaryotic cell. In some embodiments the peptide is chemically synthesized. A preferred implementation is the peptide that is chemically synthesized.

In some embodiments, the peptide is phosphorylated at a serine, threonine, or tyrosine residue.

In some embodiments, the peptide is modified at its amino terminus. Examples of amino terminal modifications include an N-glycated, N-alkylated, N-acetylated, or N-acylated amino acid. In some embodiments, the peptides include a C-terminal amidated amino acid. In other embodiments, the peptide does not include an amidated amino acid at its carboxy terminus. In some implementations of the peptide the C-terminus may include a protecting group.

In some embodiments, the peptide is pegylated.

The developments in another implementation includes a pharmaceutical composition comprising any one of the peptides of SEQ ID Nos: 7-15 and a pharmaceutically acceptable carrier.

The developments in another embodiment includes a pharmaceutical composition comprising any one of the peptides of SEQ ID Nos: 21-25; SEQ ID Nos:41-48; and SEQ ID NOs:50-52 in a pharmaceutically acceptable carrier.

In some embodiments, the peptide is less than 225, 200, 175, 150, 125, 100, 75, 50, 30, 25, 20, 15, 10, 9, 8, 7, 6, or 5 amino acids in length.

The peptides hereof may be modified to include one or more modifications. Thus, in some embodiments, the c-terminus is amidated. In other embodiments, the n-terminus is acetylated. In other embodiments, both modifications are present. In yet other implementations, neither modification is present.

The present developments may also relate to treating subjects, of human, canine, feline, and equine varieties for a variety of autoimmune diseases, including but not limited to diabetes mellitus whether insulin deficiency diabetes and insulin resistance diabetes, multiple sclerosis, rheumatoid arthritis, systemic lupus erythematosa, chronic obstructive pulmonary disease, and/or acute respiratory distress syndrome.

The present developments are based on the knowledge that interaction of CD40-ligand (CD154 protein) with CD40 protein expressed on T-cells (Th40 cells), may be important in the development of autoimmune disease and type 1 diabetes mellitus. The present developments may be based on the elucidation of the critical residues in CD40 and CD154 that may be important for this interaction. The present developments relate to affecting, modulating, and/or modifying the interaction between a CD40 protein and a CD154 protein through the use of small peptides that interact with the CD40 protein at a site where the CD154 protein would normally bind. In some aspects, the present developments may also relate to using such peptides to reduce the level of Th40 cells, thereby reducing the severity of disease.

One implementation of the present developments is a method for preventing diabetes mellitus in a subject, comprising contacting the CD40 protein with a peptide that interacts with the CD40 protein. Preferred peptides are those that are less than 25 amino acids in length, and that bind to a CD40 protein, thereby inhibiting its interaction with a CD154 protein.

One implementation of the present developments is a method for preventing autoimmune disease in a subject, comprising contacting the CD40 protein with a peptide that interacts with the CD40 protein. Preferred peptides are those that are less than 25 amino acids in length, and that bind to a CD40 protein, thereby inhibiting its interaction with a CD154 protein.

One implementation of the present developments is a method for preventing, reducing, ameliorating, and/or modulating diabetes mellitus in a subject, comprising administering to a subject in need thereof, a therapeutically effective amount of a peptide that reduces, modulates, and/or affects the blood glucose level of the subject.

One implementation of the present developments is a method for preventing, reducing, ameliorating, and/or modulating diabetes mellitus in a subject, comprising administering to a subject in need thereof, a therapeutically effective amount of a peptide that reduces, modulates, and/or affects the serum fructosamine levels of the subject.

One implementation of the present developments is a method for preventing, reducing, ameliorating, and/or modulating diabetes mellitus in a subject, comprising administering to a subject in need thereof, a therapeutically effective amount of a peptide that reduces, modulates, and/or affects the c-peptide levels of the subject.

Yet another implementation of the present developments is a method for preventing, modulating, and/or reducing diabetes mellitus, the method comprising inhibiting interaction between a CD40 protein and a CD154 protein with a peptide that interacts with the CD40 protein. Preferred peptides interact with the CD40 protein at the CD154-binding site. Preferably such peptides are less than 25 amino acids in length. Even more preferred peptides are those amino acid sequences selected from SEQ ID NOs: 7-15, 21-25, 41-48, and 50-52.

One implementation of the present developments is a method for preventing, modulating, and/or reducing autoimmune disease, the method comprising inhibiting interaction between a CD40 protein and a CD154 protein with a peptide that interacts with the CD40 protein. Preferred peptides interact with the CD40 protein at the CD154-binding site. Preferably such peptides are less than 25 amino acids in length. Even more preferred peptides are those amino acid sequences selected from SEQ ID NOs: 7-15, 21-25, and 41-48.

One embodiment of the present developments is a method for preventing, modulating, and/or reducing diabetes mellitus, the method comprising administering to a subject in need thereof, a therapeutically effective amount of a peptide that affects the interaction of CD40 with CD154/CD40-ligand. An aspect of this development may be that the peptide binds to CD40. In this embodiment, the peptide may bind to a CD40 protein with a Kd of less than $10^{-6}$. Further, in this embodiment, the peptide may affect the interaction between CD40 and CD154. Additionally, a preferred embodiment may inhibit the binding of CD40 to CD154. Moreover, in this embodiment, the peptide binds to CD40 at the site where CD40 interacts with CD154. In this embodiment, the peptide may affect the interaction of CD40 with CD154 in such a manner as to prevent the expansion of Th40 cells. In this embodiment, the peptide may affect the interaction of CD40 with CD154 in such a manner as to reduce the number of Th40 cells. In this embodiment, the peptide may affect the interaction of CD40 with CD154 in such a manner as to alter the cytokine expression profile of a cell population, treated with said peptide.

One embodiment of the present developments is a method for preventing, modulating, and/or reducing autoimmune disease, the method comprising administering to a subject in need thereof, a therapeutically effective amount of a peptide that affects the interaction of CD40 with CD154/CD40-ligand. An aspect of this development may be that the peptide binds to CD40. In this embodiment, the peptide may bind to a CD40 protein with a Kd of less than $10^{-6}$. Further, in this embodiment, the peptide may affect the interaction between CD40 and CD154. Additionally, a preferred embodiment may inhibit the binding of CD40 to CD154. Moreover, in this embodiment, the peptide binds to CD40 at the site where CD40 interacts with CD154. In this embodiment, the peptide may affect the interaction of CD40 with CD154 in such a manner as to prevent the expansion of Th40 cells. In this embodiment, the peptide affects the interaction of CD40 with CD154 in such a manner as to reduce the number of Th40 cells. In this embodiment, the peptide may affect the interaction of CD40 with CD154 in such a manner as to alter the cytokine expression profile of a cell population, treated with said peptide.

One embodiment of the present developments is a method to modulate and/or reduce diabetes mellitus in an animal, the method comprising administering to the animal, a peptide that interacts with a CD40 protein in such a manner as to modulate IFNγ (interferon gamma). Preferred peptides are those that interact with the CD40 protein at the CD154-binding site, thereby modulating IFNγ. Preferred peptides may modulate inflammation by reducing the level of Th40 cells to no more than 25% of the total T-cell population. Such methods can be used to prevent and/or reduce diabetes mellitus and symptoms that may accompany diabetes mellitus, more generally. In this implementation a peptide may be selected from SEQ ID NOs: 7-15, 21-25, 41-48, and 50-52.

One embodiment of the present developments is a method to identify a subject at risk for developing diabetes and/or autoimmune disease, the method comprising obtaining a sample containing T-cells from a subject to be tested, contacting the sample with a peptide that binds the CD40 protein, detecting the CD40 bound peptide, and determining the level of Th40 cells from the amount of CD40 bound, wherein a level of Th40 cells greater than 25% of the total T-cell population indicates the subject is at risk for developing diabetes mellitus and/or autoimmune disease.

Another aspect of the present developments, is a method to administer a bioactive peptide hereof to prevent, modulate, and/or reduce diabetes mellitus and/or autoimmune disease, comprising selecting one or more of the peptides of SEQ ID NO: 7-15, 21-25, 41-48, and 50-52; selecting a delivery method selected from the group comprising intramuscular (IM) delivery, intravenous (IV) delivery, subcutaneous (SC) delivery, oral delivery, gavage delivery, emollient/skin delivery, or transdermal patch; and using one the said delivery methods to deliver a therapeutically effective dose of the peptide.

Another aspect of the present developments, is a method to administer a bioactive peptide hereof to prevent, modulate, and/or reduce diabetes mellitus and/or autoimmune disease, comprising selecting one or more of the peptides of SEQ ID NO: 7-15; selecting a delivery method selected from the group comprising intramuscular (IM) delivery, intravenous (IV) delivery, subcutaneous (SC) delivery, oral delivery, gavage delivery, emollient/skin delivery, or transdermal patch; and using one the said delivery methods to deliver a therapeutically effective dose of the peptide.

Another embodiment of the present developments, is a method to administer a CD40 peptide to prevent, modulate, and/or reduce diabetes mellitus and/or autoimmune disease, in an animal, comprising selecting a peptide that interacts with a CD40 protein and CD154 binding site, using an extended delivery method selected from the group comprising an implantable device, a hydrophilic polymer formulation, a permeable polymeric membrane, injectable gel implants, solvent extraction system, phase inversion system, thermosensitive gels, pH dependent in situ gels, microparticles, microspheres, nanoparticles, nanospheres, bio-degradable implants, or photoactivated depot.

A peptide useful for practicing methods of the present developments should be of a size sufficient to interact with CD40 protein/CD40 complex in such a manner as to modulate diabetes mellitus. It is understood by those skilled in the art that preferred peptides are relatively short since they are easier and may be less expensive to produce. Preferred peptides may be those that are less than 20 amino acids in length. A preferred peptide may be one that is 4, 6, 8, 10, 13, and 15 amino acids in length.

Interaction of a CD40 protein and a CD154 protein has been shown to occur at particular regions within each protein. The inventors have now shown that, surprisingly, a peptide comprising only a short portion of the CD154 region that interacts with CD40 is capable of binding, affecting, and interacting with a CD40 protein, thereby modulating diabetes mellitus. Thus, one embodiment hereof is a peptide that comprises at least a portion of the amino acid sequence of a CD154 protein such that the peptide interacts with CD40 protein in such a manner as to modulate diabetes mellitus. In one embodiment, interaction of the peptide with CD40 protein results in negative modulation of diabetes mellitus. In one aspect, the peptide comprises at least a portion or a fragment of SEQ ID NO:1, SEQ ID NO:2, SEQ ID NO:3, SEQ ID NO:4, or SEQ ID NO:5.

In one aspect, the peptide is as short as possible yet comprises enough of the CD154 protein to allow interaction with a CD40 protein in such a manner as to diabetes mellitus. In one embodiment, a peptide hereof comprises 6, 13 or 15 contiguous amino acids from SEQ ID NO:1, SEQ ID NO:2, SEQ ID NO:3, SEQ ID NO:4, or SEQ ID NO:5, and interacts with CD40 in such a manner as to modulate diabetes. In one embodiment, a peptide hereof comprises 6, 13 or 15 contiguous amino acids from SEQ ID NO:1, SEQ ID NO:2, SEQ ID NO:3, SEQ ID NO:4, or SEQ ID NO:5, and interacts with CD40 in such a manner as to modulate autoimmune disease. A preferred peptide comprises a core sequence of lysine-glycine-tyrosine-tyrosine (KGYY; SEQ ID NO:6 and SEQ ID NO:20), which corresponds to amino acids 142-145 of SEQ ID NO:1, amino acids 143-146 of SEQ ID NO:2, amino acids 142-145 of SEQ ID NO:3, amino acids 142-145 of SEQ ID NO:4, and amino acids 143-146 of SEQ ID NO:5. Useful peptides can comprise additional regions of sequence from SEQ ID NO:1, SEQ ID NO:2, SEQ ID NO:3, SEQ ID NO:4, and SEQ ID NO:5 that are adjacent to the core sequence, so long as the peptide is capable of modulating diabetes mellitus and/or autoimmune disease. In one embodiment hereof, a peptide comprises at least one sequence selected from SEQ ID NOs:7-15, 21-25, 41-48 and 50-52, so long as the peptide interacts with CD40 protein in such a manner as to modulate diabetes.

While peptides of the present subject matter may be selected entirely of or from sequences that are responsible for the interaction of the peptide with a CD40 protein, they may additionally contain amino acid sequences that do not interact with a CD40 protein, but which have other useful functions. Any useful, additional amino acid sequence can be added to the CD40-interacting sequence, so long as the additional sequences do not have an unwanted effect on the ability of the CD40 interacting sequence to interact with a CD40 protein. For example, in addition to the amino acid sequence responsible for interacting with a CD40 protein, a peptide hereof can contain amino acid sequences that are useful for visualizing or purifying the peptide. Such sequences act as labels (e.g., enzymes) or tags (antibody binding sites). Examples of such labels and tags include, but are not limited to, B-galactosidase, luciferase, glutathione-s-transferase, thioredoxin, HIS-tags, biotin tags, and fluorescent tags. Other useful sequences for labeling and tagging proteins are known to those of skill in the art.

Likewise, peptides hereof may be conjugated or fused to another peptide, polypeptide, or nanoparticle, so long as such modification does not affect the ability of the peptide to modulate diabetes or autoimmune disease.

Likewise, peptides hereof can be modified, so long as such modification does not significantly affect or impact the ability of the peptide to modulate diabetes, autoimmune disease, or significantly affect the peptide's functionality in controlling and affecting blood glucose control, blood serum fructosamine levels, and/or c-peptide levels. Such modifications can be made, for example, to increase the stability, solubility or absorbability of the protein. Examples of such modifications include, but are not limited to pegylation, glycosylation, acetylation, amidation, n-terminus protection, c-terminus protection, and chemical modification of the peptide.

N-terminal modifications may include modifications provided herein, so long as such a modification does not significantly affect the peptide's functionality in performing its desired role and providing its intended therapeutic effects. Such N-terminal modifications may include, but are not limited to: 5-FAM, 5-FAM-ahx, Abz, Acetylation, Acryl, Alloc, Benzoyl, Biotin, Biotin-Ahx, BOC, Br—Ac—, BSA, CBZ, Dansyl, Dansyl-Ahx, Decanoic acid, DPTA, Fatty Acid, FITC, FITC-Ahx, Fmoc, Formylation, Hexanoic acid, HYNIC, KLH (—NH2 of N-terminal), Lauric acid, Lipoic acid, Maleimide, MCA, Myristoyl, Octanoic acid, OVA (—NH2 of N-terminal), Palmitoyl, PEN, Stearic acid, Succinylation, and/or TMR.

C-terminal modifications may include modification provided herein, so long as such a modification does not significantly affect the peptide's functionality in performing its desired role and providing its intended therapeutic effects. Such C-terminal modifications may include, but are not limited to: AFC, AMC, Amidation, BSA (—COOH of C-terminal), Bzl, Cysteamide, Ester (Oet), Ester (OMe), Ester (OtBu), Ester (OTBz1), KLH (—COOH of C-terminal), MAPS asymmetric 2, 4, or 8 branches, Me, NHEt, NHisopen, NHMe, OSU, OVA (—COOH of C terminal), p-Nitroanilide, and/or tBu.

Peptides hereof may be derivatives or fragments from those that are found in nature (e.g., obtained from plants, animals or microorganisms) or they may be produced in a laboratory (e.g., recombinantly or synthetically). Preferred peptides are those that are synthesized. Also encompassed are peptides that are combinations of natural and synthetic molecules. General methods for producing and isolating recombinant or synthetic peptides are known to those skilled in the art. It should be noted that, as used herein, an isolated, or biologically pure, molecule, is one that has been removed from its natural milieu. As such the terms isolated, biologically pure, and the like, do not necessarily reflect the extent to which the protein has been purified.

As has been described herein, interaction of the CD40 protein and the CD154 protein may be necessary for involvement of Th40 cells in diabetes mellitus and autoimmune diseases. Consequently, inhibition of the interaction between a CD40 and CD154 protein and/or CD40 complex using peptides hereof is a useful method of affecting diabetes mellitus and autoimmune diseases. Thus, one embodiment is a method to reduce the interaction between a CD40 protein and a CD154 protein comprising introducing into an environment containing a CD40 protein and a CD154 protein, a peptide, that interacts with the CD40 protein in such a manner as to reduce the interaction between the CD40 protein and the CD154 protein. In one aspect hereof, the peptide reduces the interaction between the CD40 protein and the CD154 protein by at least 5%, at least 10%, at least 20%, at least 30%, at least 40%, at least 50%, at least 60%, at least 70%, at least 80%, at least 90%, or at least 95%. In one embodiment, the peptide reduces the interaction between the CD40 protein and the CD154 protein by a factor of at least 10, at least 100, at least 1,000, at least 10,000. Methods of measuring the strength of the interaction between the CD40 protein and the CD154 protein have been discussed previously, and are also know to those of skill in the art.

One embodiment hereof is a method to modulate diabetes comprising contacting a CD40 protein with a peptide that interacts with the CD40 protein in such a manner as to modulate inflammation. In one aspect, interaction of the peptide with the CD40 protein may increase or decrease the number of Th40 cells by at least 5%, at least 10%, at least 20%, at least 30%, at least 40%, at least 50%, at least 60%, at least 70%, at least 80%, at least 90%, or at least 95%. In one embodiment, interaction of the peptide with the CD40 protein may increase or decrease the number of Th40 cells by a factor of at least 10, at least 100, at least 1,000, at least 10,000.

One aspect is a method to prevent, reduce, or modulate diabetes mellitus in a subject, the method comprising administering a peptide hereof to the patient. In one embodiment, the peptide comprises an amino acid sequence selected from SEQ ID NOs:7-15, 21-25, 41-48, and 50-52. In one embodiment, the peptide is an amino acid sequence selected from SEQ ID NOs:7-15. In a preferred embodiment, interaction of the peptide with the CD40 protein may decrease the number of Th40 cells by at least 5%, at least 10%, at least 20%, at least 30%, at least 40%, at least 50%, at least 60%, at least 70%, at least 80%, at least 90%, or at least 95%. In another embodiment, interaction of the peptide with the CD40 protein may decrease the number of Th40 cells by a factor of at least 10, at least 100, at least 1,000, at least 10,000. In a preferred embodiment, the level of Th40 cells is may be reduced so that Th40 cells comprise no more than about 20%, about 25%, about 30%, about 35%, or about 40% of the total T-cell population.

Peptides and methods hereof are suitable for use in cell culture as well as for treating a patient. As used herein the term patient refers to any animal in need of such treatment. The animal can be a human or a non-human animal. A preferred animal to treat is a mammal. A peptide can be administered or applied per se, or as pharmaceutical compositions. A peptide hereof, or a pharmaceutical composition thereof, can be administered to a patient by a variety of routes, including, but limited to, by injection (e.g., intravenous, intramuscular, subcutaneous, intrathecal, intraperitoneal), by inhalation, by oral (e.g., in a pill, tablet, capsule, powder, syrup, solution, suspension, thin film, dispersion or emulsion.), transdermal, transmucosal, pulmonary, buccal, intranasal, sublingual, intracerebral, intravaginal rectal or topical administration or by any other convenient method known to those of skill in the art.

The amount of a peptide hereof and/or a pharmaceutical composition thereof that will be effective can be determined by standard clinical techniques known in the art. Such an amount is dependent on, among other factors, the patient being treated, including, but not limited to the weight, age, and condition of the patient, the intended effect of the compound, the manner of administration and the judgment of the prescribing physician or veterinarian. Also, in this context, it should be noted that in treating a patient exhibiting a disorder of interest, a therapeutically effective amount of an agent or agents such as these is administered. A therapeutically effective dose refers to that amount of the compound that results in amelioration of one or more symptoms or a prolongation of survival in a patient.

A peptide hereof, or a pharmaceutical composition thereof, can be administered alone or in combination with one or more other pharmaceutical agents, including other compounds of the present disclosure. The peptides used and utilized in the methods may be administered to the subject in a pharmaceutically acceptable carrier, adjuvant, or vehicle. Select examples of pharmaceutically acceptable carriers, adjuvants, and vehicles, which are well-known in the art disclosed in Remington: The Science and Practice of Pharmacy, $21^{st}$ Ed., Hendrickson, R., et al., Eds., Lippincott Williams & Wilkins, Baltimore, Md. (2006). The selection of a pharmaceutically acceptable carrier, adjuvant, or vehicle will depend on a variety of factors including but not limited to, the route of administration, dosage levels, the age, weight and/or condition of the subject, etc. The specific pharmaceutical composition depends on the desired mode of administration, as is well known to the skilled artisan.

Because the inventors have discovered that Th40 cells are intimately involved in the development of autoimmune diseases and diabetes mellitus, the peptides and methods disclosed herein can be used to affect inflammation and other symptoms resulting from such diseases. Thus, one embodiment hereof is a method to treat diabetes mellitus in a patient in need of such treatment, the method comprising administering to a patient a peptide that interacts with the CD40 protein, thereby reducing diabetes mellitus. In one embodiment the peptide interacts with the CD40 protein in such a manner as to affect the interaction of CD40 and CD154, thereby reducing diabetes mellitus. In a preferred embodiment, interaction of the peptide with the CD40 protein reduces the number of Th40 cells in a patient to a level equal to that observed in subjects that do not have diabetes mellitus. The present developments may be suitable for treating any patient having an autoimmune disease and/or diabetes mellitus, the development of which is dependent on Th40 cells. More specifically, peptides hereof may be suitable for reducing the level of Th40 cells in such patients. In a preferred embodiment, a peptide hereof reduces the level of Th40 cells in a patient suffering from a diabetes mellitus to no more than about 25% of the total T-cell population.

The inventors have also shown that, surprisingly, peptides hereof can be used to reverse the disease process in individuals already showing signs of diabetes mellitus. Thus, one aspect of the present subject matter is a method to reverse diabetes mellitus comprising administering to a patient diagnosed as having diabetes mellitus, a peptide hereof. In one embodiment, the peptide comprises an amino acid sequence selected from SEQ ID NOs:7-15, 21-25, 41-48, and 50-52, so long as the peptide can down-regulate inflammation. As used herein the phrase to reverse diabetes mellitus means to reduce diabetic symptoms to a level comparable to the observably lower level of symptoms and measurements may be more common in a non-diabetic subject. The subject may be required to continue the therapy indefinitely to continue to achieve the desired results from the therapy. In other instances, it may be possible for the subject to be titrated off of the therapy, yet have the positive effects and changes induced by the therapy carry-forward. This may be dependent on a number of factors, including but not limited to the disease state when initially presented, the progression of the disease state, and other factors as may be determined by a physician or veterinarian as the case may be.

As has been described, peptides of the present invention selectively interact with and/or affect CD40 expressing cells. Consequently, peptides of the present subject matter may be used to identify Th40 cells. Thus, one embodiment hereof is a method to detect Th40-dependent diabetes mellitus, said method comprising contacting a T-cell population with a peptide hereof. In a preferred embodiment, the peptide is labeled with a detectable marker, such as, for example, luciferase or alkaline phosphatase. Such detection can be performed using assay techniques known to those skilled in the art. In general, an assay for detecting Th40 cells using a peptide hereof comprises (a) obtaining a sample of cells; (b) contacting a peptide hereof with said cells under condition suitable to allow binding of the peptide to Th40 cells, if present; (c) washing said cells using conditions that disrupt non-specific interactions, and that remove unbound peptide; and (d) detecting peptide bound to cells. Detection of bound peptide can be achieved directly or indirectly. For example, direct detection can be achieved using a peptide labeled using a detectable marker, as disclosed herein. Following the wash step listed above, the cells are then simply screened for the presence of detectable marker. The presence of detectable marker in the cell sample indicates the presence of Th40 cells, and thus Th40-dependent diabetes. Alternatively, indirect detection involves the use of a second molecule, such as an antibody, that binds to the peptide. In an indirect detection assay, following the wash step listed above, a detection molecule that binds the peptide is added to the cell sample. The detection molecule is labeled with a detectable marker. After washing away unbound detection molecule, the cells are screened for the presence of detectable marker. The presence of detectable marker in the cell sample indicates the presence of Th40 cells. It should be understood that the assays described herein are meant as examples of useful assays, and other assay techniques can be employed. Suitable assay techniques are known to those skilled in the art, and are also disclosed in, for example, Molecular Cloning: A Laboratory Manual, Sambrook, J., Fritsch, E. F., and Maniatis, T, Cold Spring Harbor Laboratory Press; 2nd Edition (December 1989). All references cited herein are incorporated herein in their entirety.

The peptide utilized and described in the above-mentioned detection method may also include modifications to the peptide such as stable isotope labeled peptides or fluorescent peptide modifications/FRET pairs that may allow the peptide to be utilized in several detection methods and applications. For example, stable isotope labeled peptides, such as: Arg(13C6, 15N4), Ile (13C6, 15N), Leu (13C6, 15N), Lys (13C6, 15N2), and/or Val(13C5, 15N) may be utilized. Moreover, fluorescent peptide modifications/FRET pairs, such as: 1-Pyrenemethylamine HCL, 5-FAM (N-Terminal), 5-FAM-Ahx (N-terminal), Abz (N-Terminal), Abz/

DNP, Abz/Tyr (3-NO2), DABCYL, DABCYL/Glu (EDANS)-NH2, Dansyl (N-Terminal), Dansyl-Ahx (N-Terminal), EDANS/DABCYL, FITC (N-Terminal), FITC-Ahx (N-Terminal), Glu(EDANS)-NH2, MCA (N-Terminal), MCA/DNP, Quenched fluorescent peptide, Tyr (3-NO2), TMR, and/or AMC may be utilized. Thus, the peptides hereof may be modified in such a way whether with stable isotope peptides or fluorescent peptide modifications/FRET pairs that may allow the peptides of SEQ ID NOs: 7-15, 21-25, 41-48, and 50-52, or others disclosed herein, to be used for assays or other useful procedures.

The assay technology described above can also be used to identify other molecules that affect the interaction of a CD40 protein with a CD154 protein. Examples of such molecules include, but are not limited to, proteins, peptides and small molecules. For example, assays can be designed that test the ability of molecules to compete with a peptide of the present developments for binding to a Th40 cell. For instance, a peptide labeled with a detectable marker, can be mixed with a test molecule and a population of cells known to contain Th40 cells, under conditions that allow binding of the peptide to the Th40 cells. Following an appropriate incubation period, the cells are washed to remove unbound peptide, and the cells screened for the presence of detectable marker. Alternatively, the labeled peptide could be bound to Th40 cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the Th40 cells, while presence of the detectable marker would indicate the test molecule does not inhibit binding of the peptide to Th40 cells. Inhibition of binding need not be 100%, as such assay would also be useful for identifying molecules that partially inhibit binding of the peptide to Th40 cells. It is understood by those skilled in the art that such assays would involve the use of positive controls (e.g., unlabeled peptide) and negative controls (e.g., a protein/molecule that is known not to bind to Th40 cells).

Because increased levels of Th40 cells may be associated with the development of autoimmune disease, the present developments can be used to identify patients at risk for developing autoimmune disease and autoimmune related diabetes mellitus. Thus, one embodiment of the present developments is a method to identify a patient at risk for developing autoimmune related diabetes mellitus. In one embodiment, patients at risk for developing diabetes mellitus are identified by obtaining a sample from a patient to be tested, contacting the T-cell portion of said sample with a peptide hereof, and determining the level of Th40 cells present in the sample, wherein a level of Th40 cells greater than about 25% of the total T-cell population indicates the patient is at risk for developing autoimmune disease or diabetes mellitus. In one embodiment, the peptide comprises an amino acid sequence selected from SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15, so long as the peptide binds to the CD40 protein. In one embodiment, the peptide is an amino acid sequence selected from SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In another implementation, the amino acid sequence is selected from one of SEQ ID NOs:7-15, 21-25, 41-48, and 50-52. In one implementation, the peptide is labeled with a suitable detectable marker such as, for example, luciferase or alkaline phosphatase.

The present developments also comprise kits useful for practicing the methods disclosed herein, the kit comprising a peptide that interacts with a CD40 protein in such a manner as to modulate diabetes mellitus. In one embodiment, the peptide comprises an amino acid sequence selected from SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15, so long as the peptide can down-regulate diabetes mellitus. In one embodiment, the peptide is an amino acid sequence selected from SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In one embodiment, the peptides is an amino acid sequence selected from SEQ ID NOs:7-15, 21-25, 41-48, and 50-52. Another embodiment is a kit for determining the level of Th40 cells, the kit comprising a peptide that interacts with a CD40 protein, and methods for detecting CD40-bound peptide. Kits can also contain associated reagents and components, such as, but not limited to, buffers, labels, containers, inserts, tubing, vials, syringes, and the like. Kits may also contain peptides that have stable isotope labeled amino acids or fluorescent peptide modifications/FRET pairs, as described elsewhere herein.

Another embodiment of the present developments includes a method to modulate and/or reduce interleukin 17 (IL-17) in a cell or a subject comprising administering a peptide selected from SEQ ID NOs 7-15, 21-26, 41-48, and 50-52 in an amount sufficient to reduce or inhibit interleukin 17 (IL-17) signaling, wherein, the IL-17 signaling is associated with a condition selected from the group comprising type I diabetes, multiple sclerosis, systemic lupus erythematosa, rheumatoid arthritis, Crohn's disease, inflammatory bowel disease, chronic obstructive pulmonary disease, asthma, atherosclerosis, vasculitis, hypertension, thyroiditis, primary biliary cirrhosis, Paget's disease, Addison's disease, acute respiratory distress syndrome, acute lung injury, and/or aseptic chronic inflammation, more generally.

Another embodiment of the present developments includes a method to modulate and/or reduce interleukin 17 (IL-17) in a cell or a subject comprising administering a peptide selected from SEQ ID NOs 7-15, 21-26, 41-48, and 50-52 in an amount sufficient to reduce or inhibit interleukin 17 (IL-17) signaling, wherein, the IL-17 is associated with diabetes mellitus.

One aspect of the developments hereof includes an implementation wherein the peptides of SEQ ID NOs 7-15, 21-26, 41-48, and 50-52 may be provided as a sterile solution in phosphate buffered saline (PBS). In this implementation, the pH is approximately 5.5.

The following examples are provided for the purpose of illustration and are not intended to limit the scope of the present invention.

EXAMPLES

Example 1

This Example demonstrates the effect of various peptide fragments of CD154 on CD4/CD8 ratios and the development of diabetes in NOD mice.

Figure 2A:
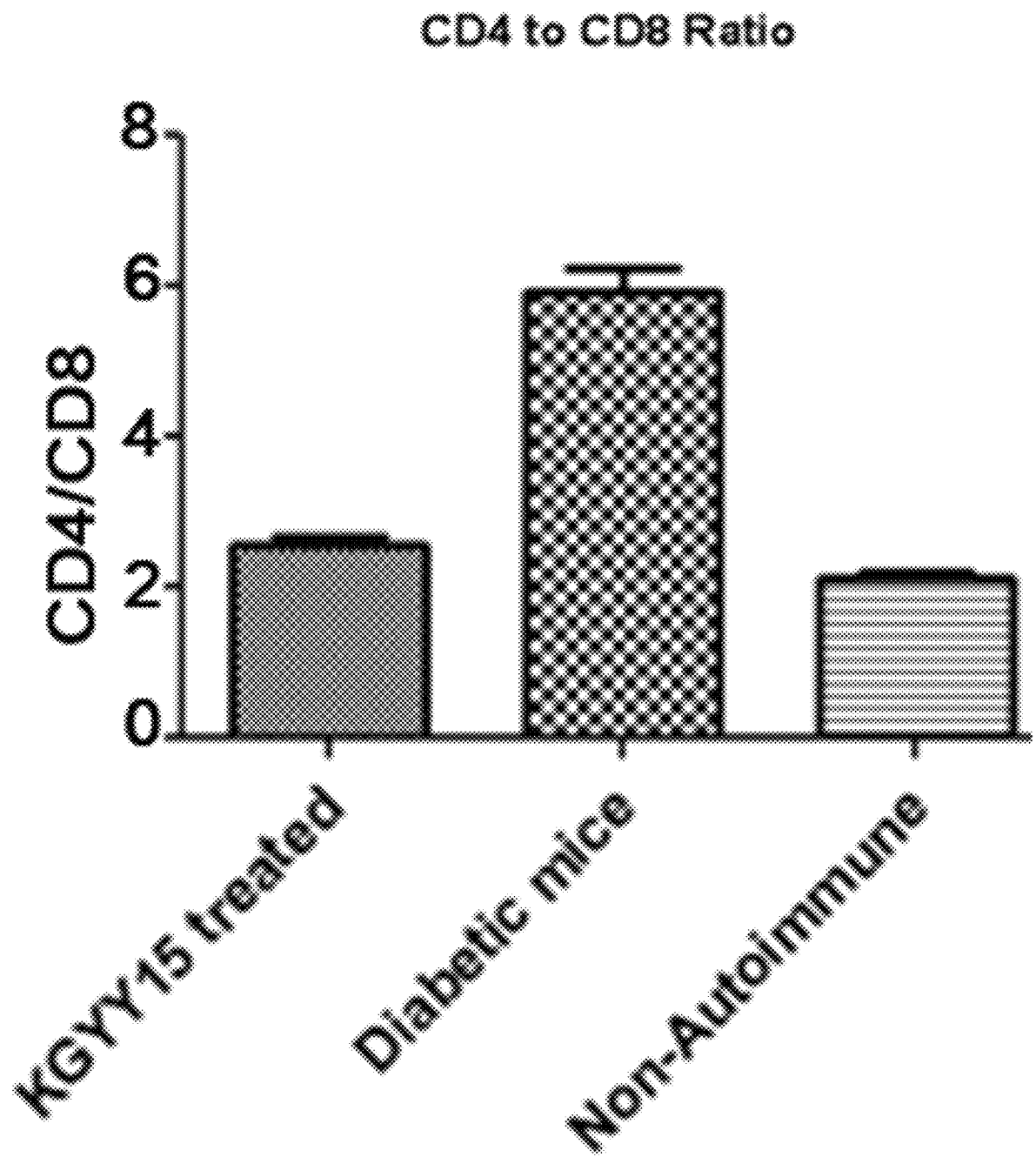
FIG. 2A is a chart of the effect of a 15-mer peptide from CD154 on the CD4/CD8 ratio in NOD mice.

Peptides were designed based on the amino acid sequence of mouse CD154 protein (SEQ ID NO:1) in the SwissPro database. The peptides (8-mer (SEQ ID NO: 22; SEQ ID NO: 23), 10-mer (SEQ ID NO:41), 13-mer (SEQ ID NO:42), 15-mer (SEQ ID NO: 24), 24-mer (SEQ ID NO:26), scrambled (SEQ ID NO: 40), and RGD (arginylglycylaspartic acid) were then ordered from New England Peptide. The RGD peptide is a 15-amino acid sequence from the CD154 sequence that does not include the CD40 binding motif. The lyophilized peptides were suspended in sterile PBS at 1 mg/ml. 25 ug (1mg/kg) of a particular peptide was then injected into the tail vein of 6-week old NOD mice. Control mice received 100 ul of sterile PBS. This is well before the onset of diabetes (and atherosclerosis), but after damage to pancreatic islets has begun. Weekly after the initial injection, another 25 ug of peptide (or 100 ul of PBS in the case of the Control mice) was injected into the tail vein. At 10 weeks of age, mice were monitored for diabetes, as indicated by a blood glucose level greater than 250 mg/dL for three consecutive days. The results of this study are shown in FIG. 1. During this time, blood was also taken from the tail vein, or by sub-mandibular venal puncture, and the level of CD4+ and CD8+ cells determined by flow cytometry using antibodies for CD4 protein and CD8 protein. The results of this analysis are shown in FIG. 2A.

Figure 2B:
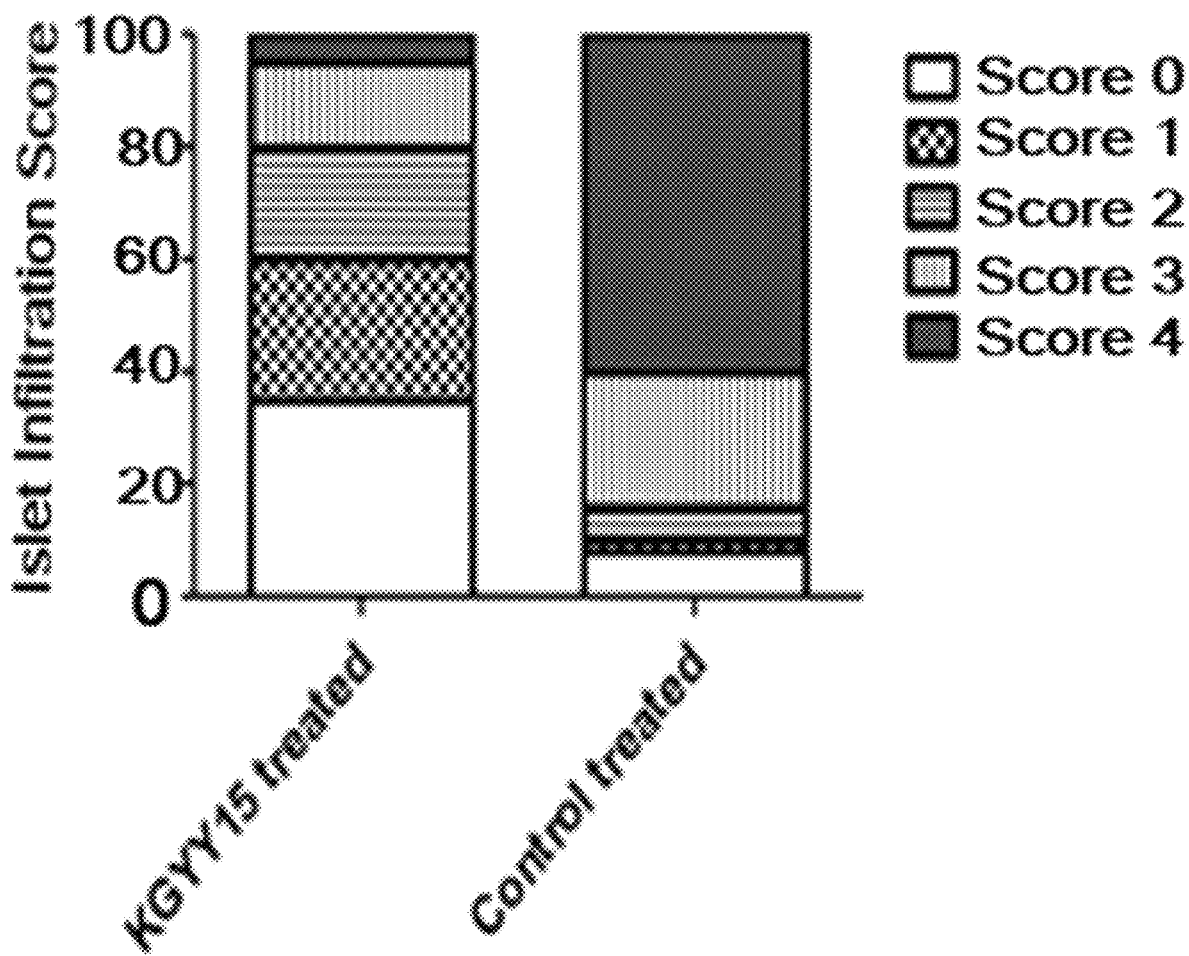
FIG. 2B is a chart of the effect of 15-mer peptide in treated versus control pancreata excised, examined, and scored.

Pancreata were excised and examined by histology for cellular infiltrates and assigned scores based on observable, measurable, and quantifiable data: 0=no infiltrate; 1=one pole infiltrate; 2=peri-insulitis, bi-polar-infiltrates; 3=75% infiltrate and 4=full infiltration. The results of this analysis are shown in FIG. 2B.

The results demonstrate that treatment with a peptide unrelated to the CD154 protein did not reduce the development of diabetes in NOD mice. In contrast, treatment of mice with a 15-mer peptide derived from the CD154 protein prevented the onset of diabetes. Further, the 13-mer peptides derived from the CD154 protein had significant effects on the development of diabetes. In addition, the data demonstrates that the 15-mer peptide did not result in compromise of the immune system, as determined by the CD4/CD8 ratio.

Example 2

This Example demonstrates the effect of the 15-mer peptide on hyperglycemia in newly diabetic NOD mice.

Figure 3:
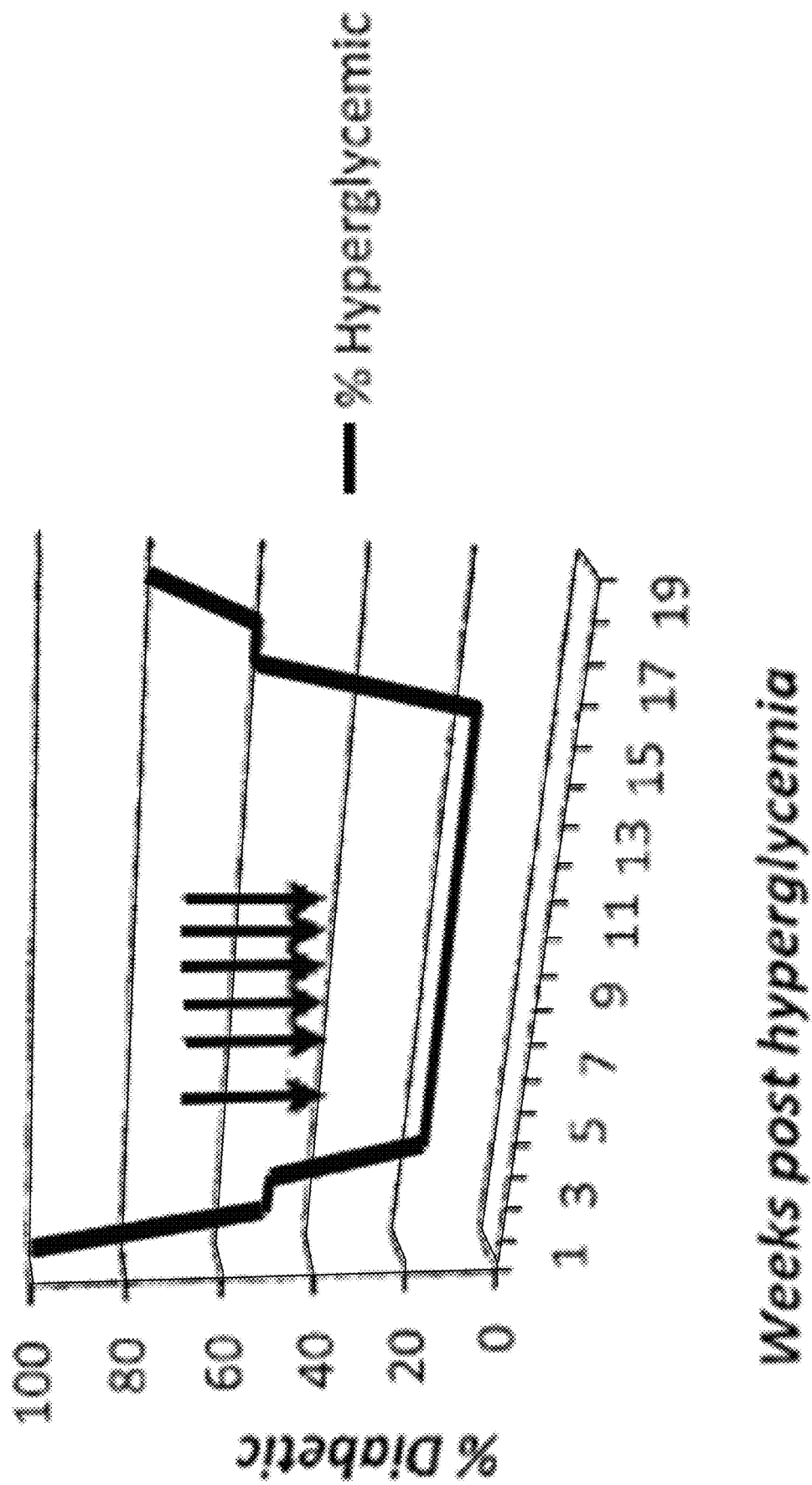
FIG. 3 is a graph of reversal of diabetes in NOD mice using a 15-mer peptide from CD154.

Six mice that had received the 6-mer peptide in Example 1, and that had subsequently developed diabetes, were injected intravenously with 100 ug of the 15-mer peptide. These mice were then given weekly injections of the 15-mer peptide into their tail veins, and their blood glucose levels monitored twice-weekly. The 15-mer peptide was administered for a total of ten weeks, after which the treatment was stopped. The results of this study are shown in FIG. 3.

This study demonstrates that injection of the 15-mer peptide into already diabetic mice can reverse hyperglycemia. It also demonstrates that cessation of the treatment results in return of hyperglycemia within 7 weeks.

Example 3

This study demonstrates the ability of the 15-mer peptide to bind to Th40 cell and B cells.

Figure 4:
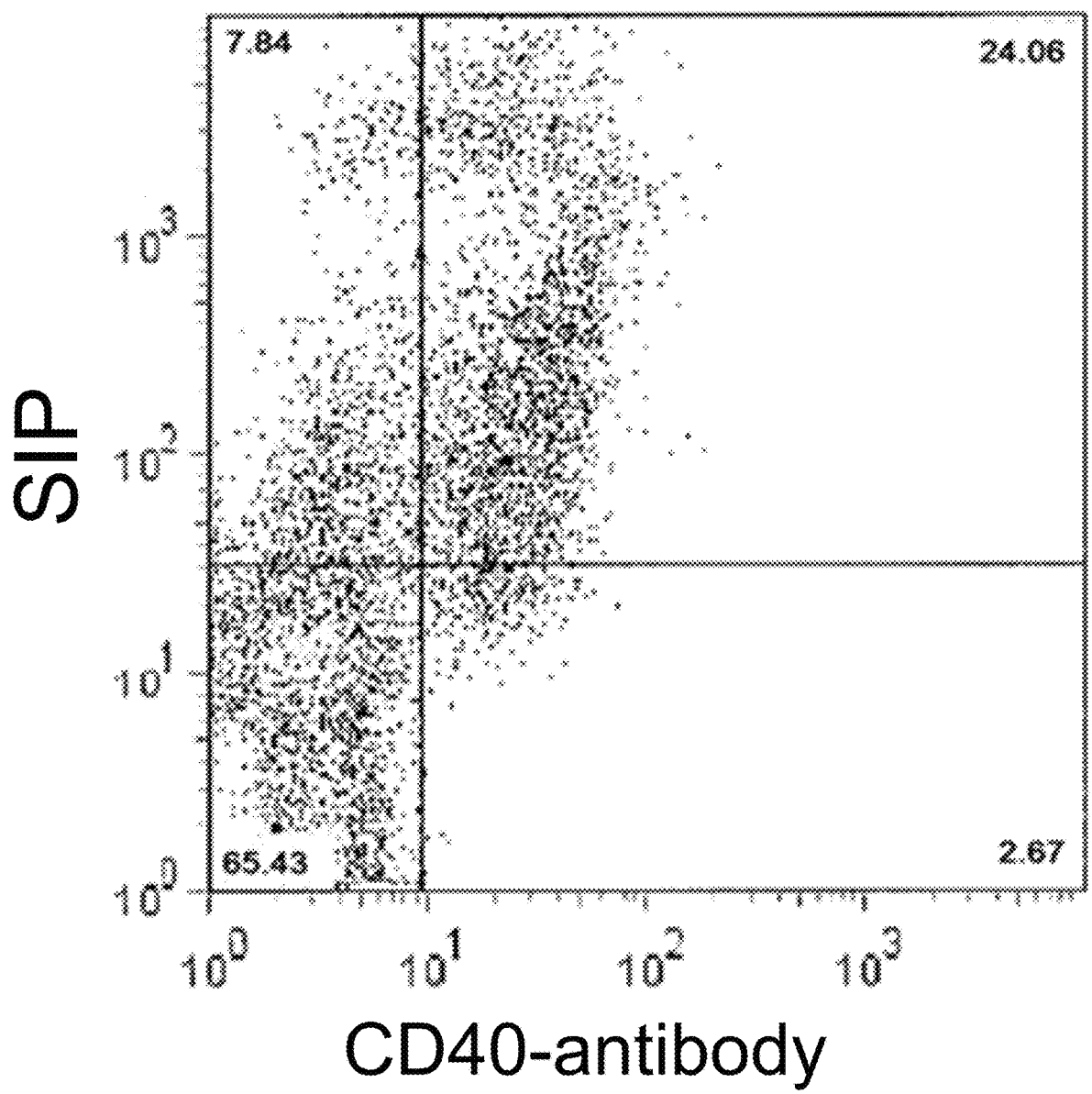
FIG. 4 is a dot-plot of the detection of Th40 cells using a 15-mer peptide from CD154.

Total lymphocytes were isolated from 9 week old NOD mice. The lymphocytes were incubated with anti-CD4, anti-CD8, and an FITC-labeled 15-mer peptide, and then analyzed by flow cytometry. Cells were gated for CD4 (both CD4hi and CD4lo populations were included) and CD40 versus the 15-mer peptide. The results of this analysis are shown in FIG. 4.

Figure 5:
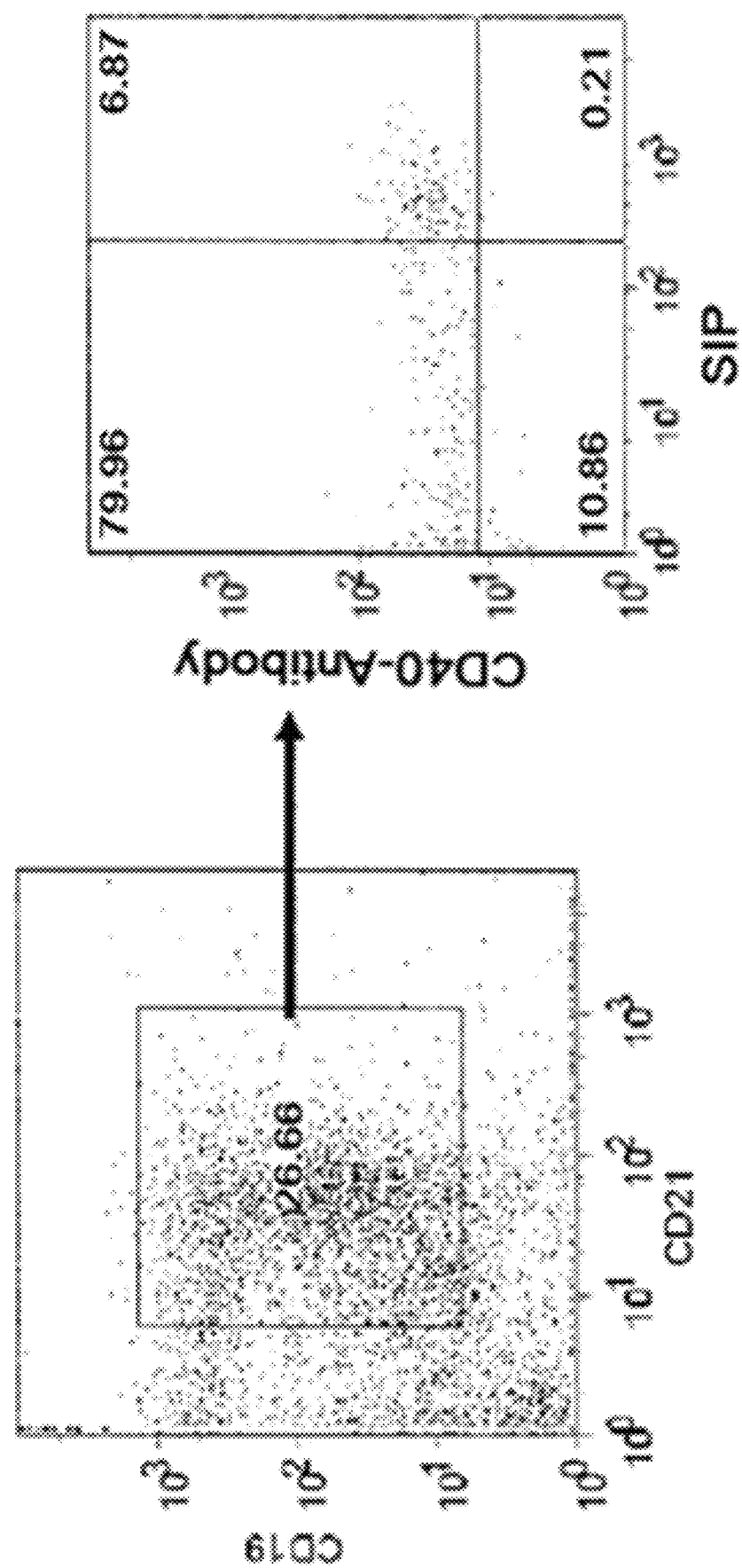
FIG. 5 is a dot-plot of a screening of B cells using a 15-mer peptide from CD154.

B cells were isolated from the spleens of NOD mice. Sorted MHC-II+ cells were purified from total lymphocytes. Cells were stained with FITC-labeled 15 mer peptide, anti-CD40, and B cell markers CD19 and CD21. MHC-II+ cells were gated for CD19+ and CD21+ and then 15-mer peptide versus CD40 antibody was measured. The results of this study are shown in FIG. 5.

This study shows that a substantial majority, 90% of CD40+ T-cells, also bind the 15-mer peptide, thereby demonstrating that the 15-mer peptide is highly specific for CD40+ cells. It also shows that while 90% of B cells were CD40 positive, only 8% of B cells bound the 15-mer peptide.

Example 4

This example demonstrates the level of CD40 positive cells in the blood of type-I diabetic subjects and non-diabetic (control) subjects.

Figure 6:
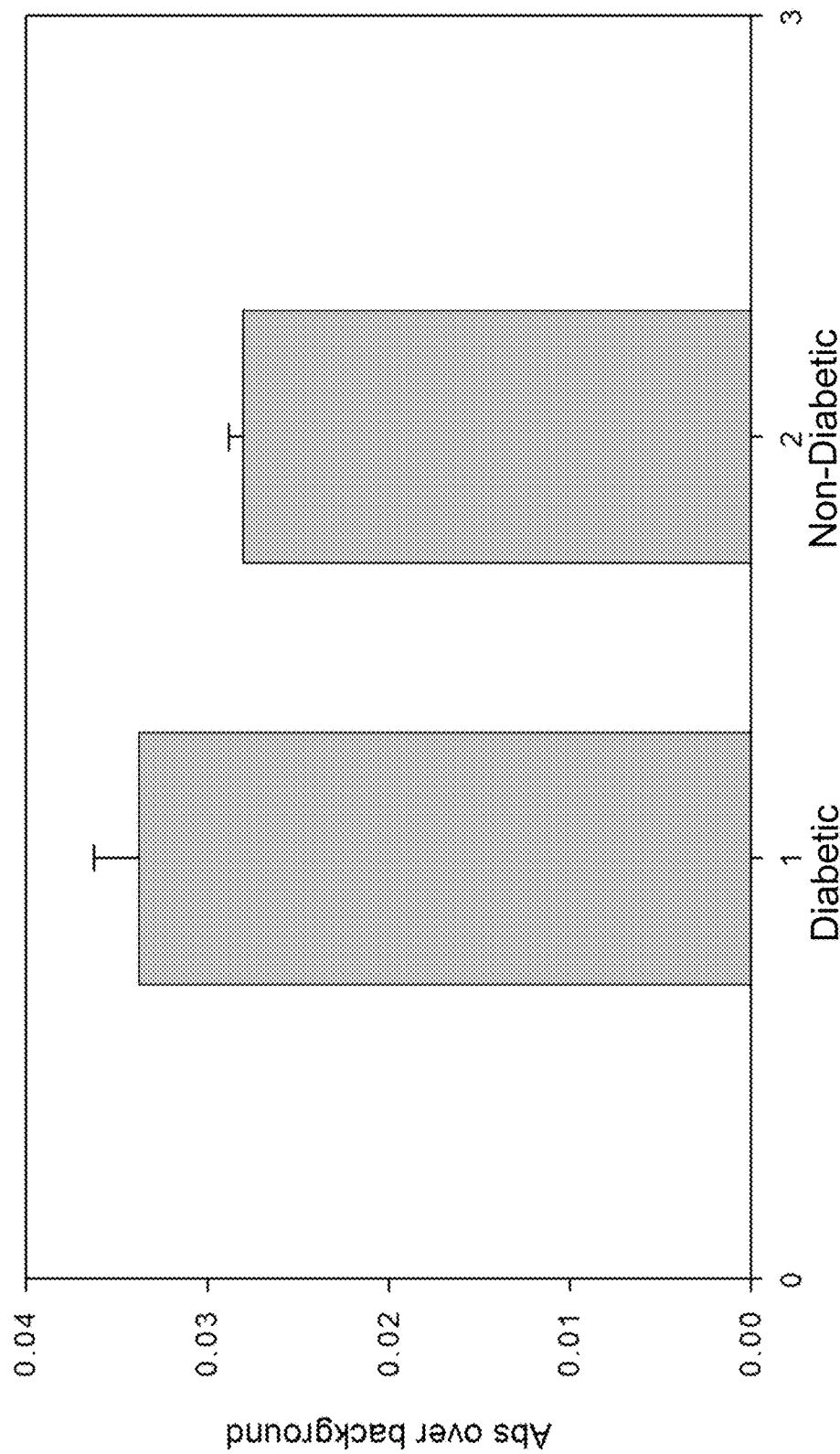
FIG. 6 is a chart demonstrating a comparison of Th40 cell levels in diabetic and non-diabetic mice.

1 ml of whole blood was obtained from each individual and incubated with biotin-conjugated, 15-mer peptide. The cells were then exposed to horseradish peroxidase (HRP)-avidin, washed and the absorbance at 405 nm determined using a spectrophotometer. The results of this study are shown in FIG. 6.

This study demonstrates that blood cells from patients having type-I diabetes had higher 15-mer peptide binding activity than cells from non-diabetic controls.

Example 5

This example demonstrates the level of insulin granulation observed in the pancreas of NOD mice treated with either the 15-mer peptide or a peptide from ovalbumin.

Figure 7:
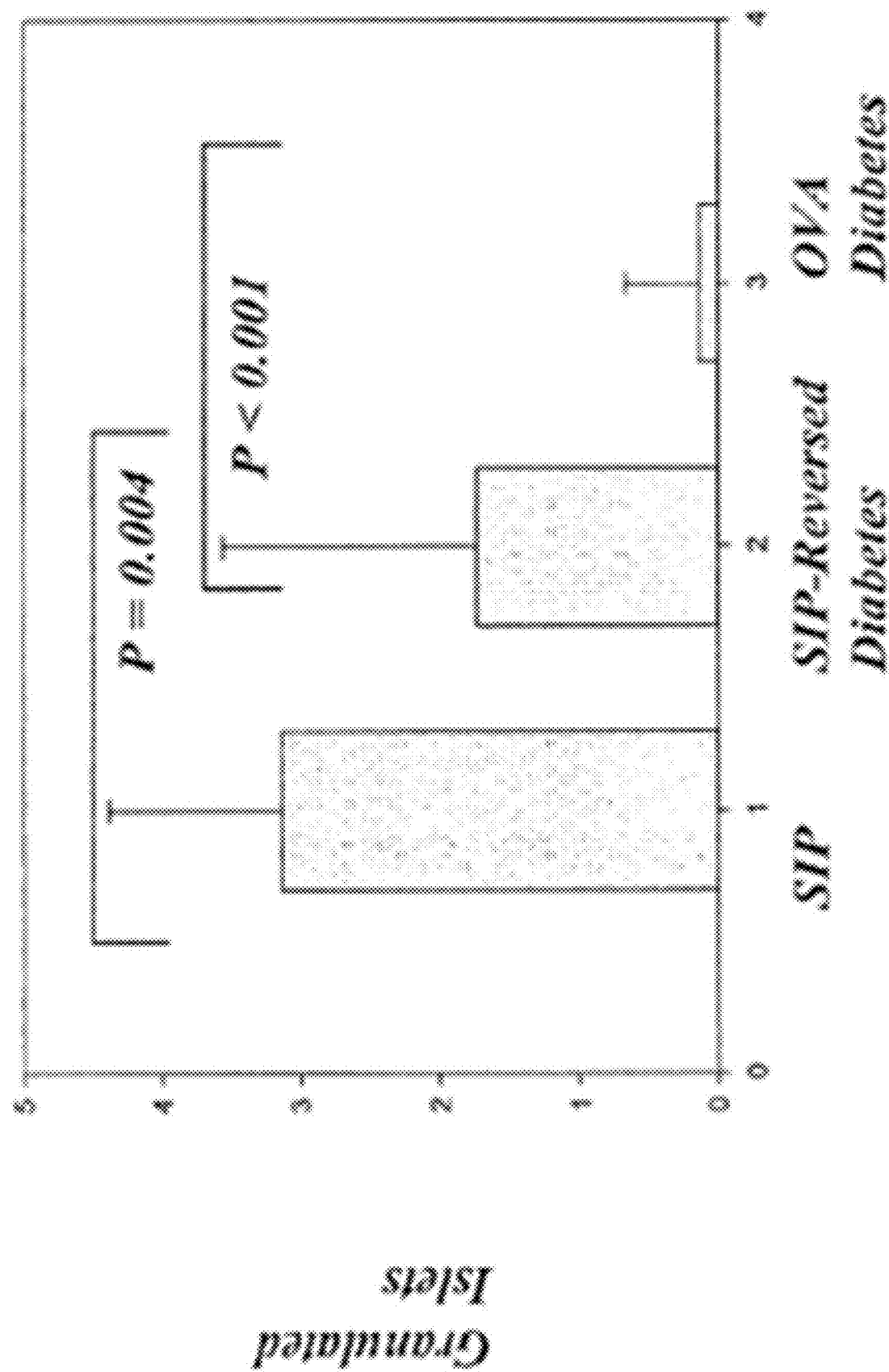
FIG. 7 is a chart demonstrating the effect of treatment with the 15-mer peptide on insulin granulation of the pancreas.

At the onset of diabetes, six NOD mice were injected with 100 ug/ml of the 15-mer peptide (SEQ ID NO:24), resulting in the reversal of hyperglycemia in 80% of the recipients. Six weeks after reversal of hyperglycemia, mice were sacrificed and the pancreas removed for analysis. The pancreas was fixed, sectioned and then stained using an aldehyde/fuschsin stain that allows detection of insulin granules. Granulation of the tissue was scored as follows: 4=completely granulated; 3=75% of islet granulated; 2=50% of islet granulated, and peri-insulitis; 1=25% of islet granulated; 0=no insulin granules detected. The results of this analysis are shown in FIG. 7.

This analysis demonstrates that the 15-mer peptide preserved insulin granules in the majority of the mice, and was significantly improved in peptide-reversed diabetic mice compared to diabetic mice that received an irrelevant peptide.

Example 6

Figure 8:
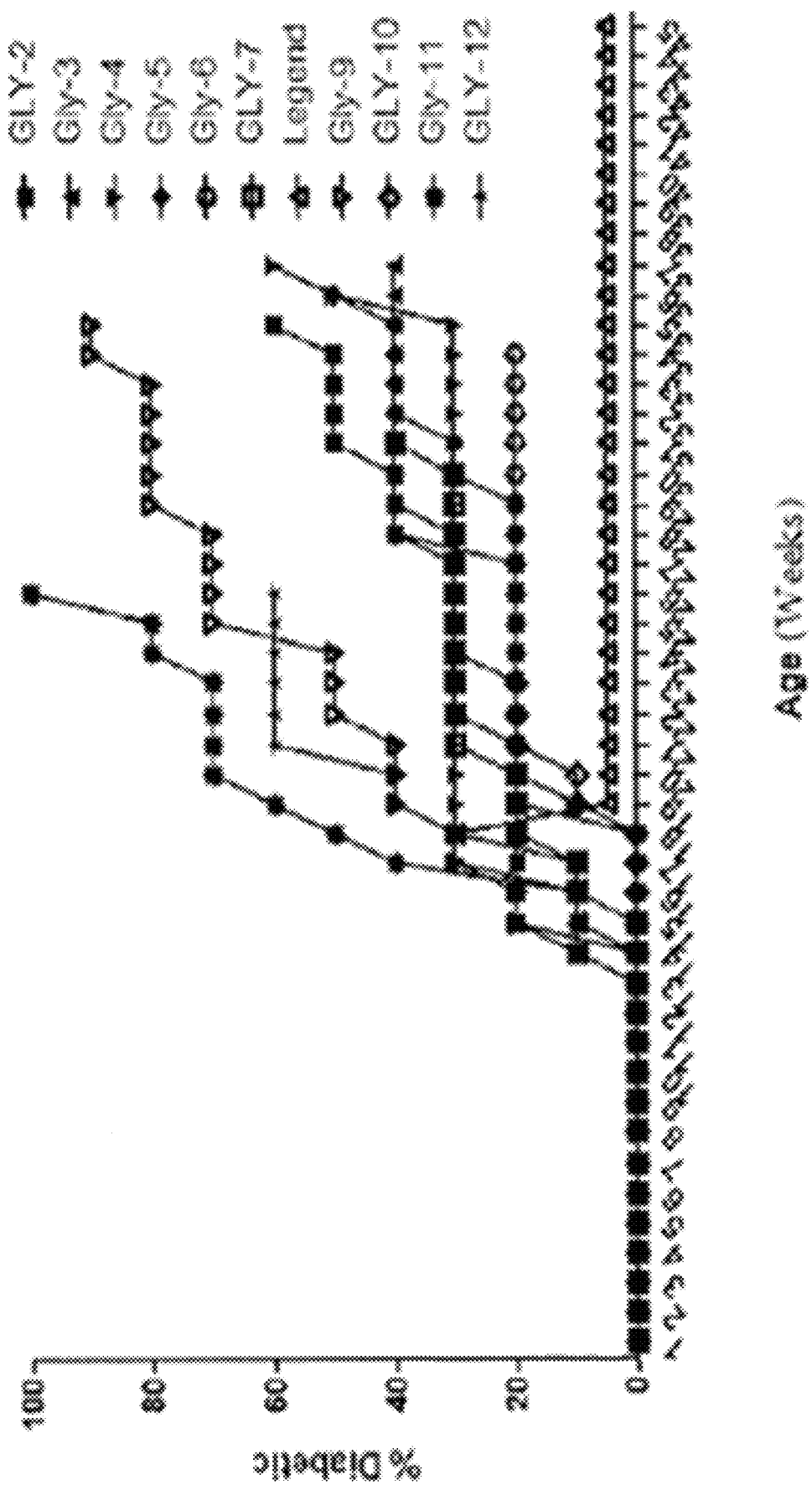
FIG. 8 is a graph that shows the effect of mutations in the 15-mer peptide on the ability of the 15-mer peptide to inhibit development of diabetes in NOD mice.

This example demonstrates the effect of mutations in the 15-mer peptide on its ability to prevent the onset of diabetes. FIG. 8 provides results related to this Example 6.

Peptide were designed and produced as described in Example 1. Variant peptides were produced so that in each variant, a glycine was substituted for an amino acid corresponding to an amino acid in positions 1-9 of SEQ ID NO: 24, as follows:

```
Gly-1
                               (SEQ ID NO: 28)
G-L-Q-W-A-K-K-G-Y-Y-T-M-K-S-N

Gly-2
                               (SEQ ID NO: 29)
V-G-Q-W-A-K-K-G-Y-Y-T-M-K-S-N
```

-continued

Gly-3
(SEQ ID NO: 30)
V-L-G-W-A-K-K-G-Y-Y-T-M-K-S-N

Gly-4
(SEQ ID NO: 31)
V-L-Q-G-A-K-K-G-Y-Y-T-M-K-S-N

Gly-5
(SEQ ID NO: 32)
V-L-Q-W-G-K-K-G-Y-Y-T-M-K-S-N

Gly-6
(SEQ ID NO: 33)
V-L-Q-W-A-G-K-G-Y-Y-T-M-K-S-N

Gly-7
(SEQ ID NO: 34)
V-L-Q-W-A-K-G-G-Y-Y-T-M-K-S-N

Gly-9
(SEQ ID NO: 35)
V-L-Q-W-A-K-K-G-G-Y-T-M-K-S-N

Gly-10
(SEQ ID NO: 36)
V-L-Q-W-A-K-K-G-Y-G-T-M-K-S-N

Gly-11
(SEQ ID NO: 37)
V-L-Q-W-A-K-K-G-Y-Y-G-M-K-S-N

Gly-12
(SEQ ID NO: 38)
V-L-Q-W-A-K-K-G-Y-Y-T-G-K-S-N

NOD mice were placed in groups of 10, and the mice in each group injected IV weekly with 25 ug of either wild-type (WT; Legend) peptide or a variant peptide (in PBS, ph 7.2) listed above. The development of diabetes was monitored by measuring blood glucose levels on a weekly basis. Mice were considered "diabetic" when blood glucose was 250 mg/dl or greater for 2 consecutive readings. Injections began at 6 weeks of age=pre-diabetes.

This example demonstrates that substitution of a glycine at any of positions 1-7, or 9-12, reduces the ability of the 15-mer peptide to inhibit the development of diabetes. It also shows that such mutations do not completely abolish the ability of the mutated 15-mer peptide to inhibit the development of diabetes.

Example 7

This example demonstrates that the same elevation of Th40 cell levels in the ApoE deficient mouse model of atherosclerosis is also notably elevated in human Type 1 Diabetes (T1D).

Figure 9:
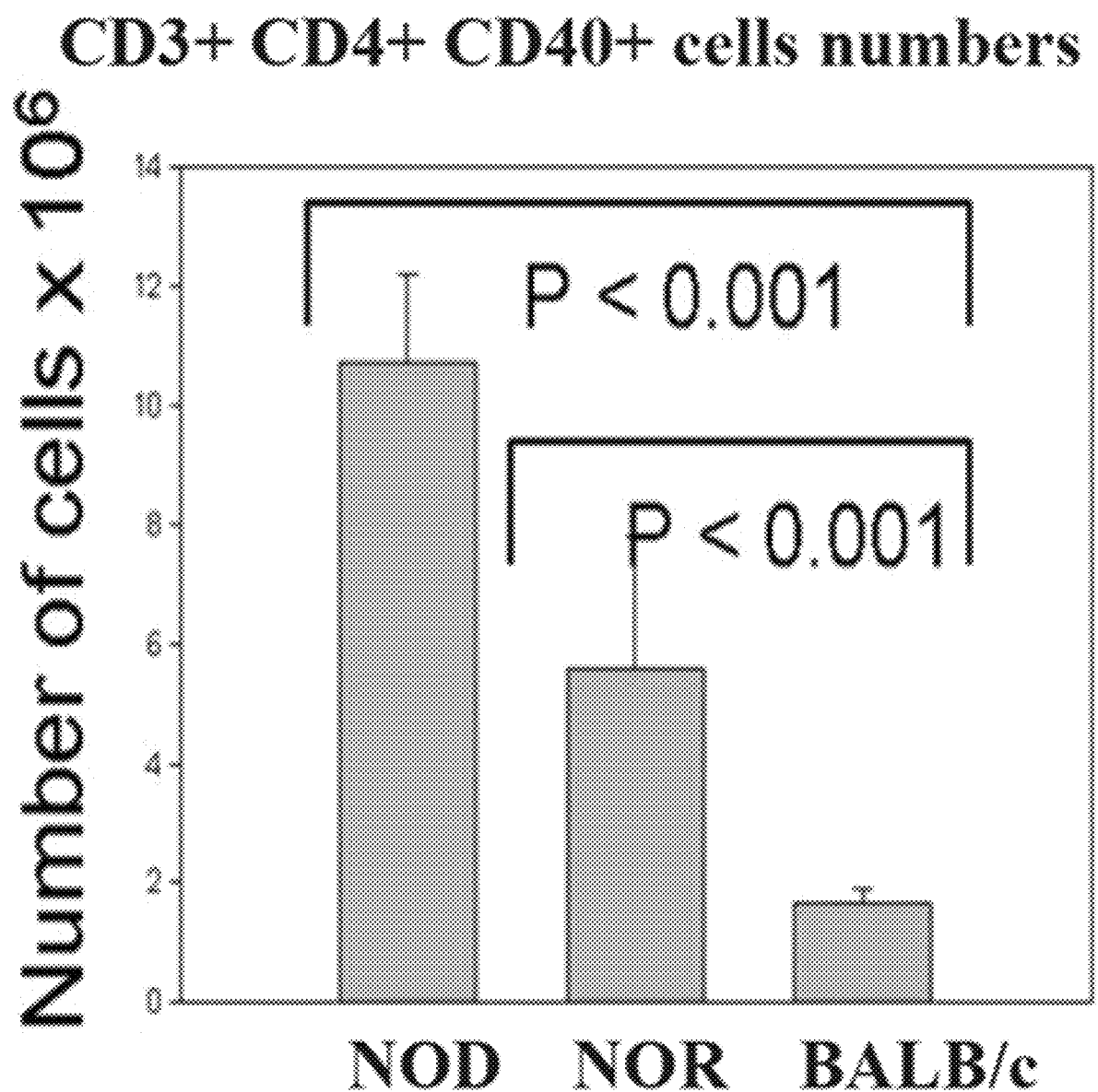
FIG. 9 is a chart showing the number of cells ($\times 10^6$) of CD3+CD4+CD40+ in different mice models.
Figure 10:
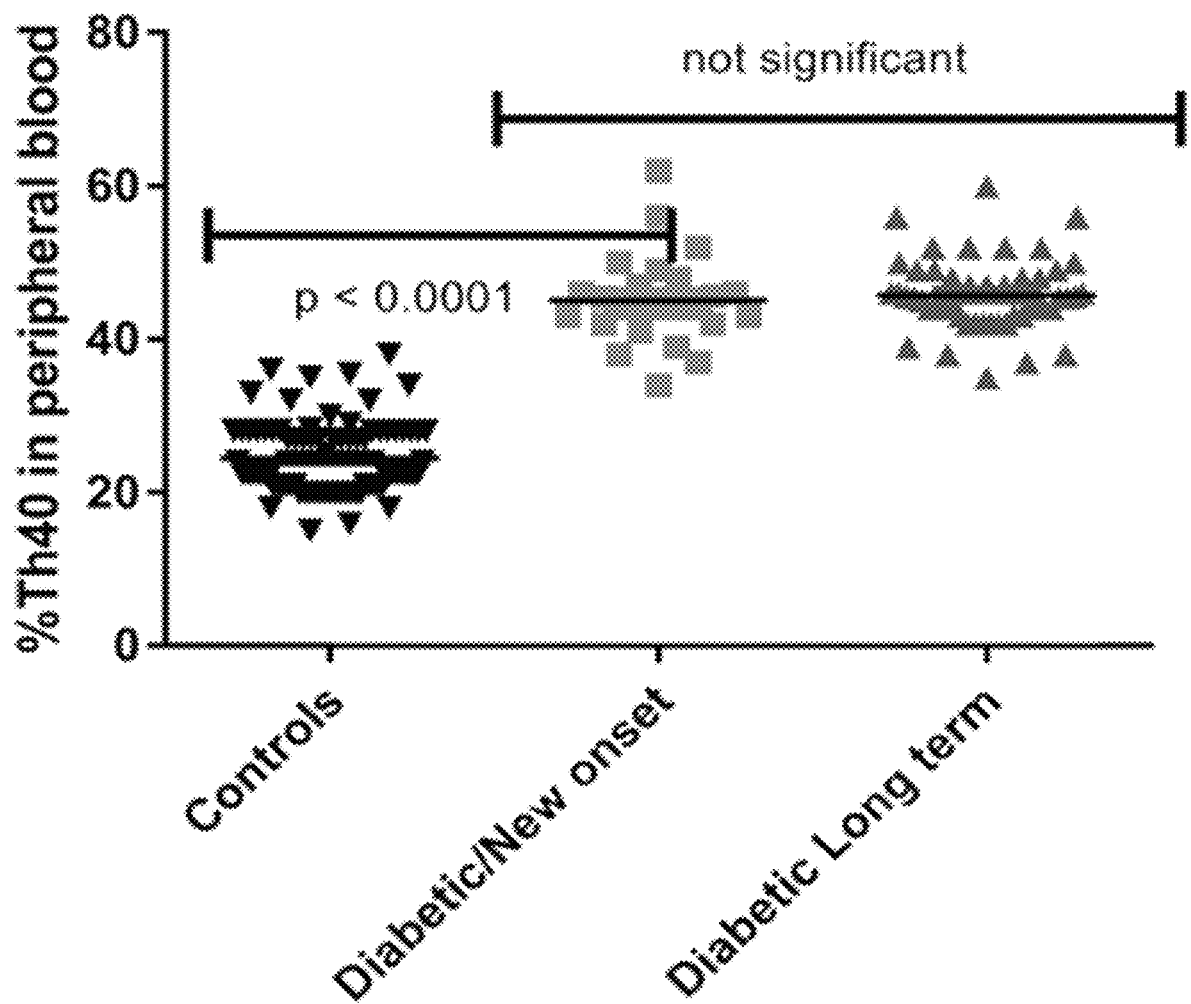
FIG. 10 is a chart showing the percentage of TH40 cells in the peripheral blood in human subjects in control and diabetic subjects.

The peripheral blood was measured was measured for total count of CD3+CD4+CD40+ cell numbers in NOD, NOR (non-obese diabetic resistant), and BALB/c (control) mice as in FIG. 9. This was compared to the percentage of Th40 cells in peripheral blood in human subjects for control, diabetic/new onset, and long-term diabetic populations as in FIG. 10.

Example 8

Figure 11:
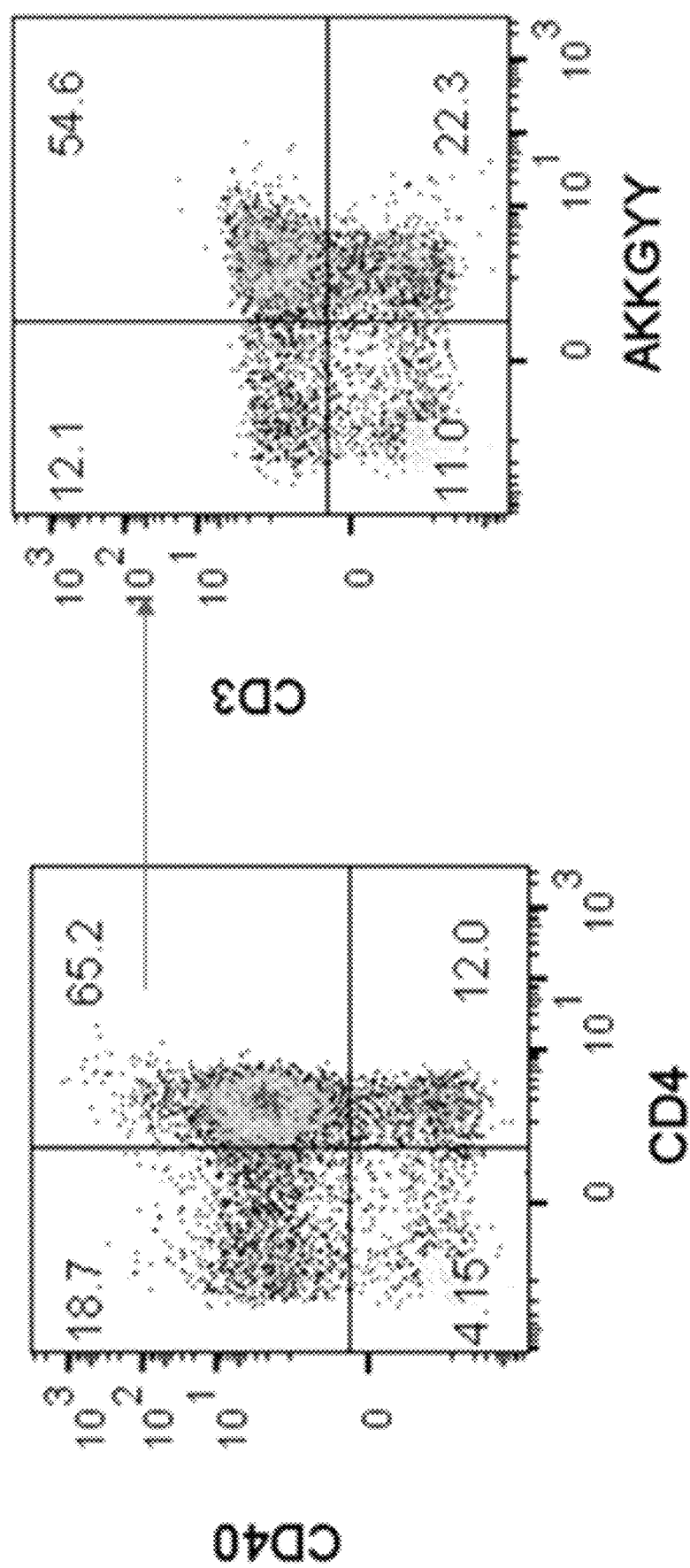
FIG. 11 is a dot-plot of detection of Th40 cells in canine blood (of canine known to have diabetes) using a 6-mer peptide (SEQ ID NO: 46) from CD154.

Dog blood was obtained from a known diabetic dog. Peripheral blood mononuclear cells were isolated. Cells were stained with CD3, CD4 and CD40 and with the peptide of SEQ ID NO: 46. These results are shown in FIG. 11.

Example 9

Five diabetic dogs including 4 new onset and 1 long-term, (diagnosis greater than 3 years) were recruited into a test case study. The dogs were enrolled at Colorado State University Veterinary Hospital (CSU-VH), Fort Collins, Colo. for the study. Each dog was assessed by a Board-Certified Veterinarian. Blood samples were collected from each dog and analyzed by chemistry panels to determine general health, as well as assessed by complete physical examination. The dogs were each confirmed diabetic, blood glucose ranging from 300-600 mg/dl but were generally in good health otherwise. One dog was diagnosed with hypertension, and two dogs had eye problems, partial blindness and the long-term dog was completely blind from diabetes.

Breeds were varied and sizes ranged from 8 to 27 kilos. Four of the dogs had been diagnosed for 3 months or less, 1 dog was diagnosed for 3.5 years. All dogs were receiving daily insulin treatments. The route of administration was IV infusion of SEQ ID NO. 13 over 30 minutes at 2 mg/kg on Days 0, 4, 8 and then weekly thereafter for a total of 8 weeks. The dogs were treated with the dog-sequence (SEQ ID NO: 13—VLRWAPKGYYTISSN); acetate salt form; brought up in sterile PBS for injection; injection was done as a slow infusion over 30 minutes. All five dogs experienced positive outcomes while on treatment: reduction of blood and urine glucose, elimination of ketonuria in all dogs and in 2 of the dog's urine glucose was eliminated. The dog diagnosed for 3.5 years experienced an improvement of time-in-range (percentage of a 24-hour period that blood glucose ranged between 80 and 160) from 10% to 80% for 5 consecutive days in the 5th week and achieved this for the last 3 test weeks. Typical responses in all five dogs was that 3-5 days post treatment improvements in blood glucose occurred. For example, blood glucose would move from 400 to 120, remain stable for 2 days but return to elevated levels. In all the treated dogs, glucose spikes were at lower levels, 300 mg/dl as a high, compared to >500 mg/dl prior to treatment. In fact, prior to treatment, none of the dogs recorded blood glucose levels less than 350. During treatment dogs were at 200 mg/dl or lower the majority of the time and in many cases were at 150 mg/dl or less. There were no negative impacts on dogs WBC and RBC and all chemistry panel numbers were normal, as before.

Figure 15:
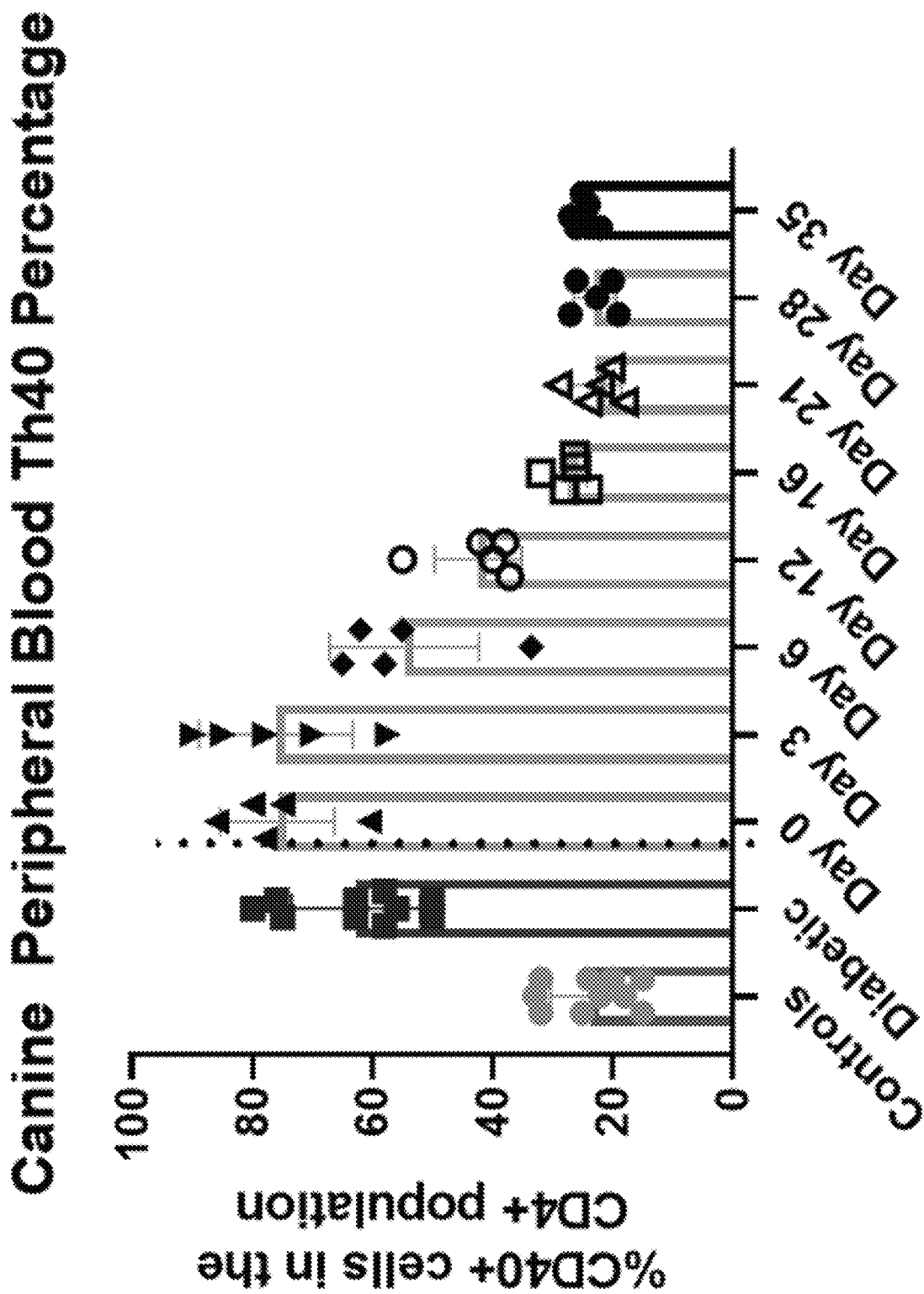
FIG. 15 provides a chart of Th40 percentage in canine peripheral blood.
Figure 16:
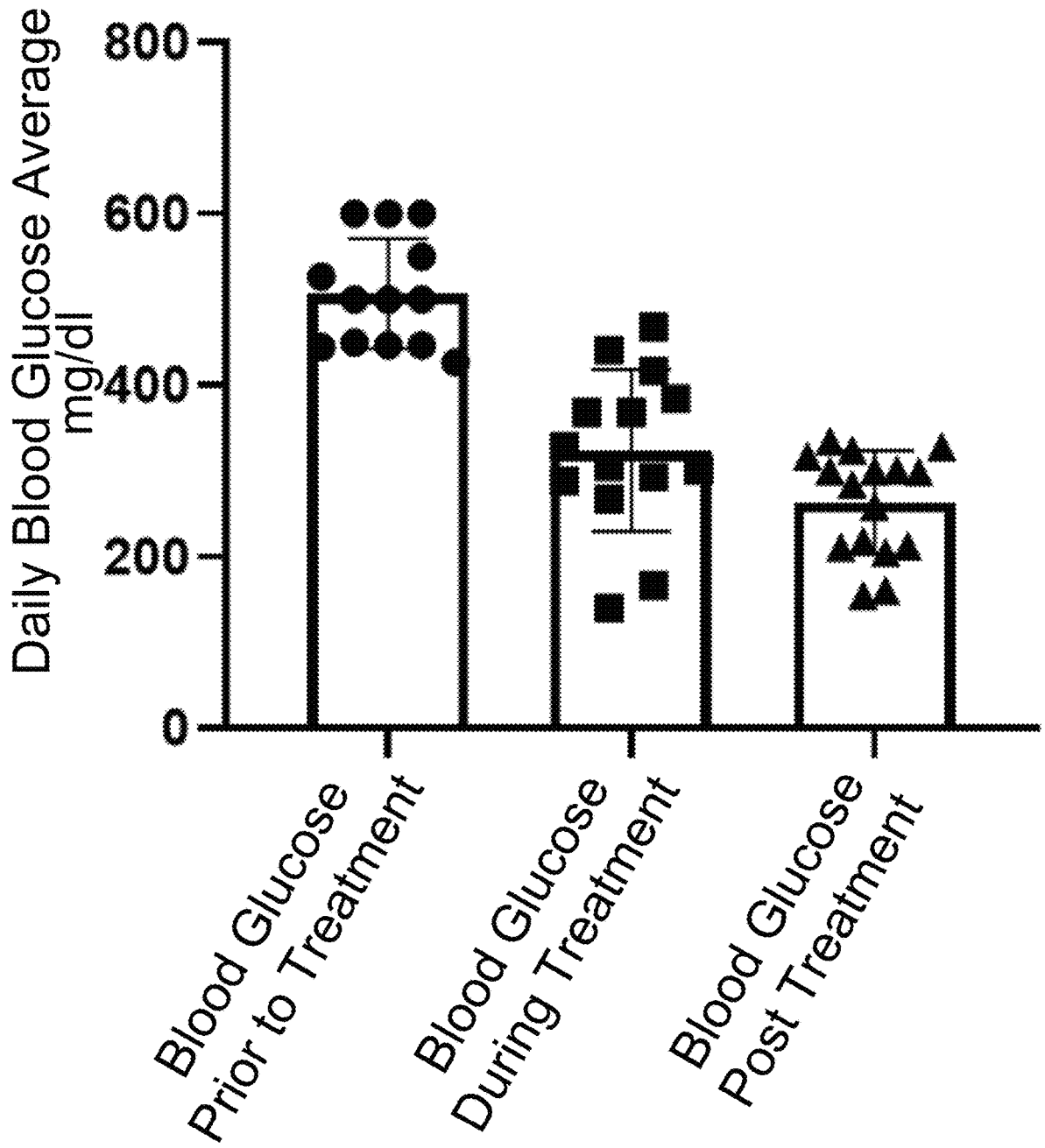
FIG. 16 provides a graph showing the daily blood glucose average for a male diabetic dog subject prior to treatment, during treatment, and post-treatment.
Figure 17:
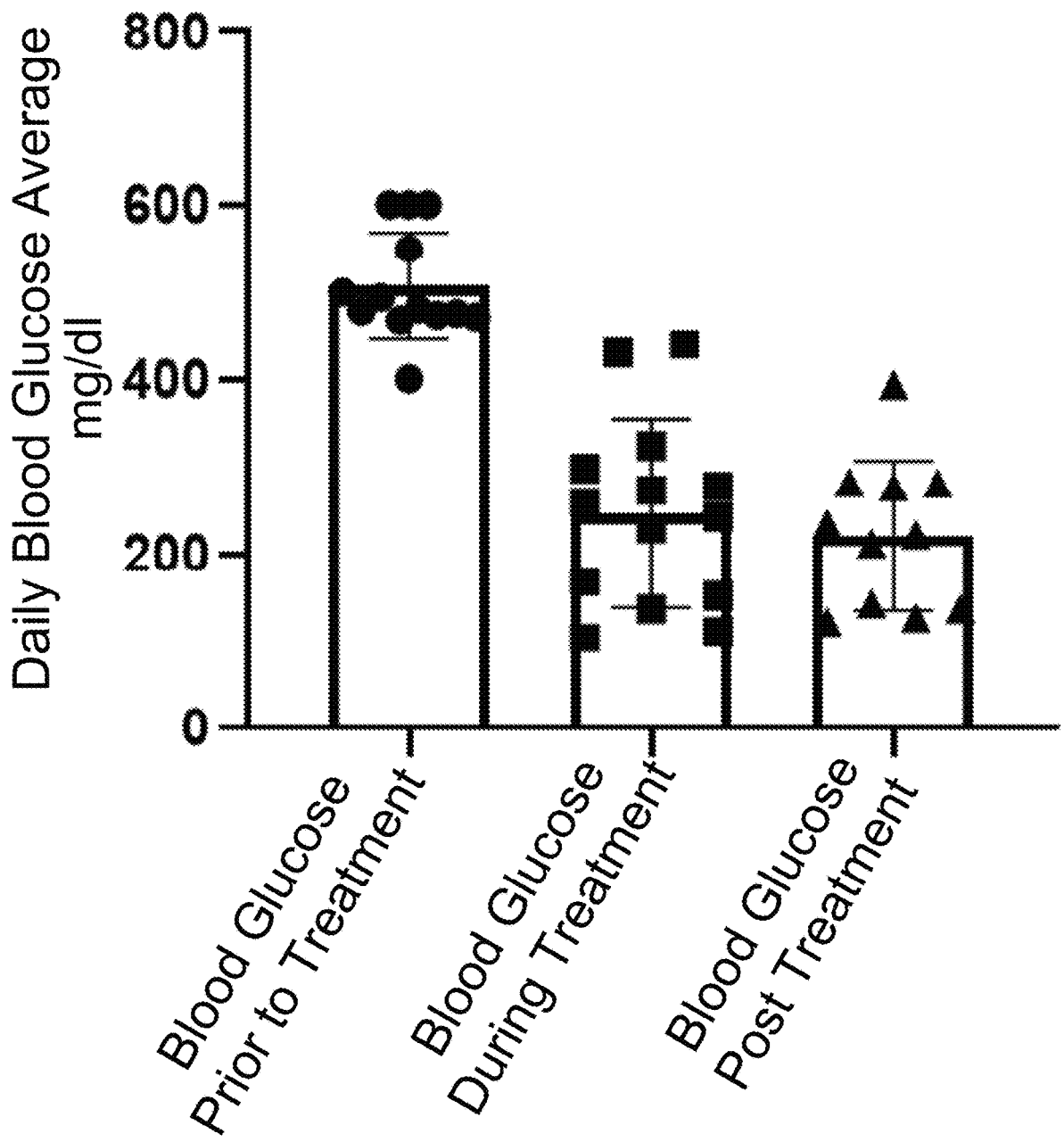
FIG. 17 provides a graph showing the daily blood glucose average for a female diabetic dog subject prior to treatment, during treatment, and post-treatment.

Prior to treatment blood samples were analyzed for blood glucose levels and Th40 cell percentages in peripheral blood. These pre-treatment Th40 cell levels and blood glucose levels can be seen in FIGS. 15, 16, and 17. In FIG. 15, controls are blood samples from test beagles used by CSU-VH and were all confirmed non-diabetic (i.e. not diabetic). Control samples demonstrate that Th40 cells in "normal" dogs are at modestly low levels (<25%), as has been reported for mice and humans. On day 0, prior to the first treatment, blood was collected from leg vein and analyzed for Th40 cell percentages. Prior to treatment, all diabetic dogs demonstrated Th40 cells in peripheral blood at 50% or higher as in FIG. 15. Samples were analyzed for Th40 cells by flow cytometry. Furthermore, isolated blood was processed to obtain lymphocytes. Lymphocytes were stained with antibodies to recognize CD4 and CD40, which are definitionally Th40 cells. The percentage of CD4+ CD40+ as a subset of total CD4+ cells was determined and graphed. By day 6, following the third treatment, all dogs showed reduction in Th40 cell levels, by day 16 ($5^{th}$ treatment) all dogs had Th40 cell percentages in the normal range. Dogs were treated through day 28. On day 35, one week after the last treatment, Th40 cell levels remained at or within a normal range. Treatment did not result in ablation, but only reduction in Th40 cell numbers. Three of the five dog subjects were re-examined two months later, Th40 cell levels remained reduced, but were beginning to return to higher numbers. None of the dogs experienced any adverse effects. Blood chemistry panels showed normal levels on most parameters, each improved from blood samples prior to treatment. Two examples of blood panels and results are provided in FIG. 19 and FIG. 20.

Blood glucose measurements were taken on diabetic dogs prior to, during, and post-peptide treatment. Data collected by a blood analysis and by continuous glucose monitoring were obtained. The continuous glucose monitoring readings were obtained periodically and the readings displayed are daily averages taken over a 2-week period. Male dog—subject 5 and female dog—subject 3 both demonstrated consistent high glucose readings prior to treatment, see FIG. 16 for results of male dog—subject 5; see FIG. 17 for results of female dog—subject 3. During the treatment period of 28 days, blood samples were taken and glucose monitoring data was recorded. The results are plotted and shown in FIG. 15. For this graph, daily averages were taken after day 6 and through day 28, which was the final treatment. Post-treatment blood glucose levels were monitored for up to 2 months.

Figure 12:
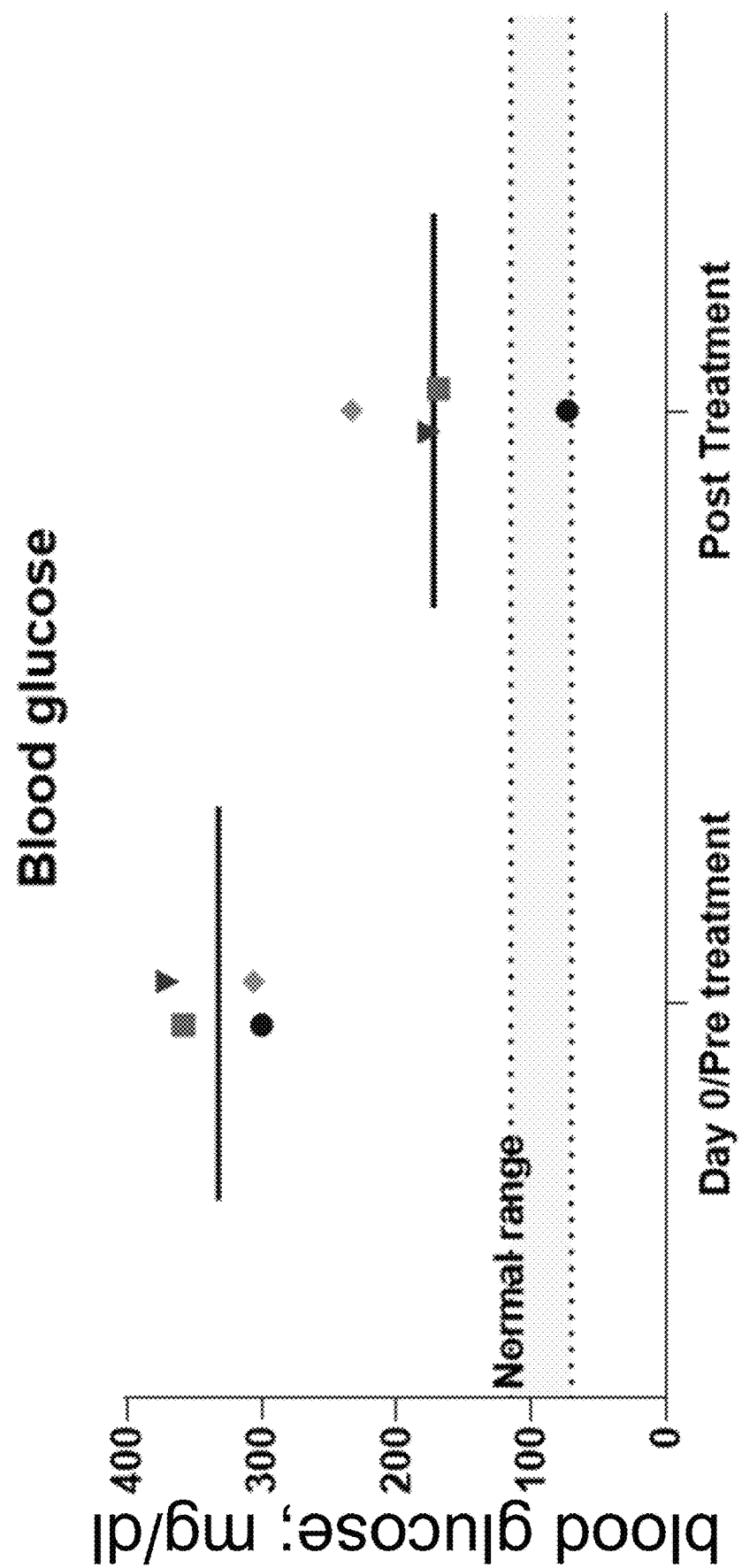
FIG. 12 is a graph of the blood glucose levels of diabetic dog subjects pre- and post-treatment.

FIG. 12 provides a graph of the blood glucose levels on four of the five dogs pre-treatment and post-treatment. Longer treatment may result in further glucose control. Using a multi column t-test, each dog experienced a significant p=0.0042 blood glucose drop. Overall, all treatment reduced blood glucose significantly, p=0.0040.

Figure 13:
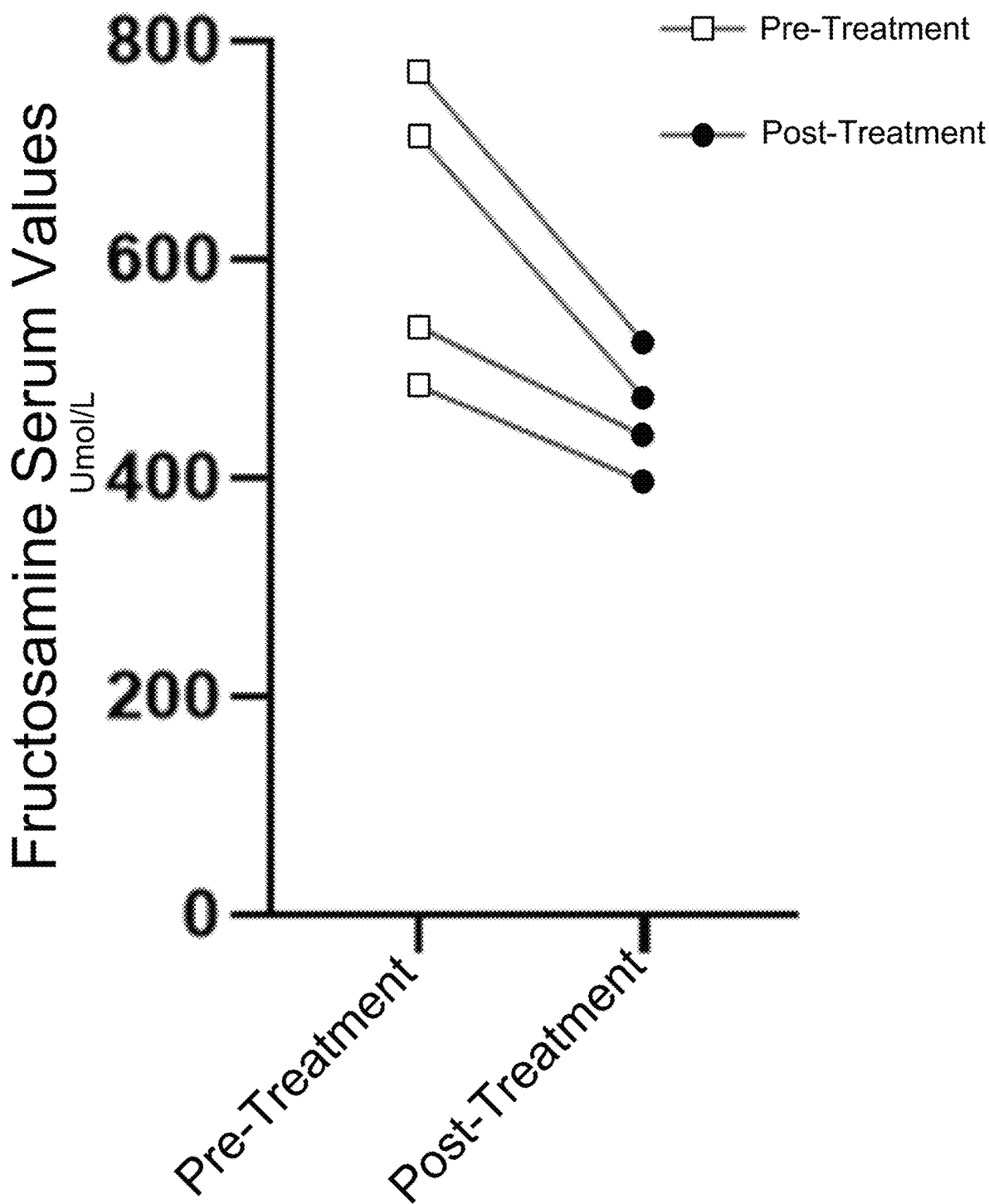
FIG. 13 is a graph of fructosamine serum values in diabetic dog subjects pre- and post-treatment.
Figure 14A:
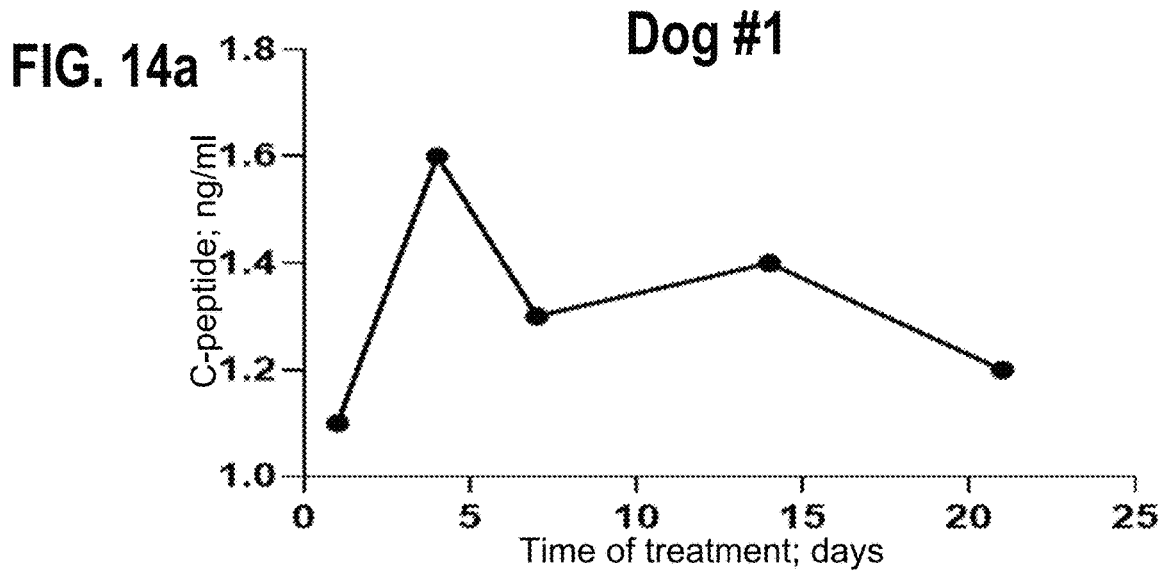
Figure 14B:
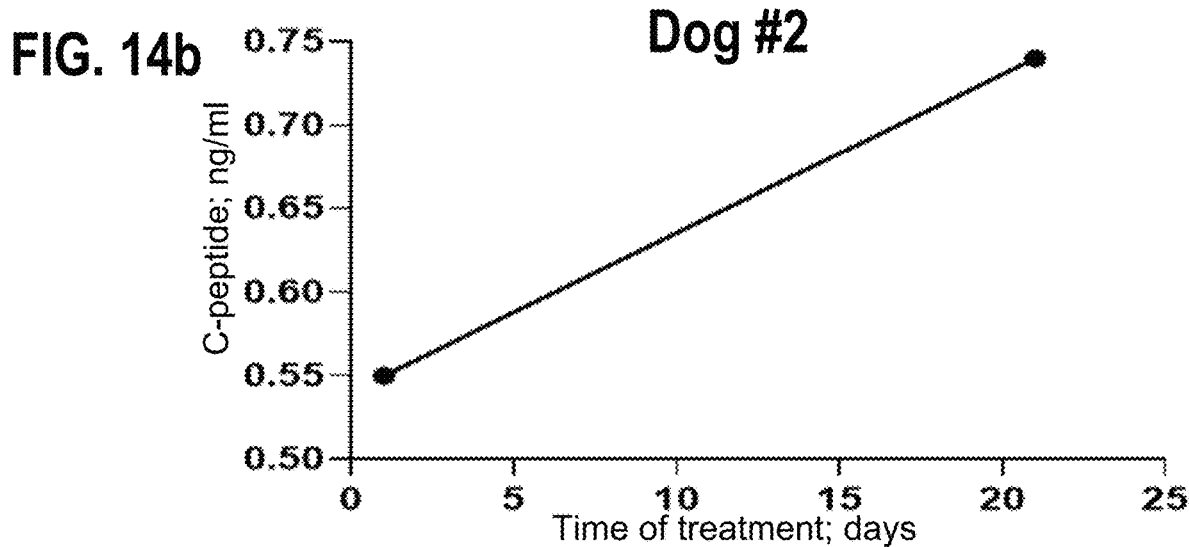
Figure 14C:
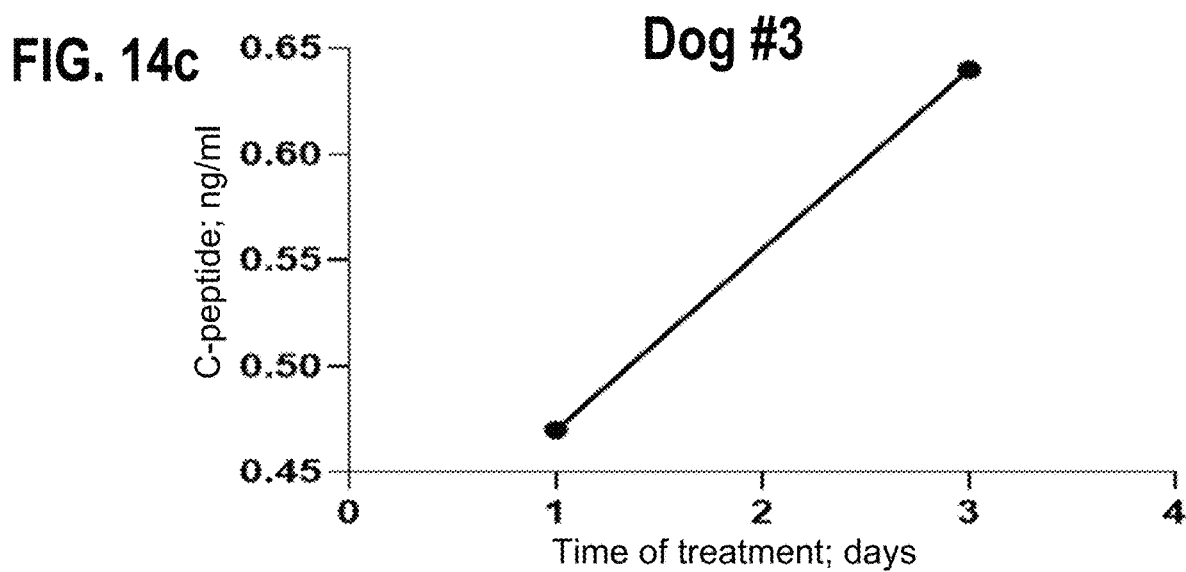

FIG. 13 provides a graph of glycosylated fructosamine serum level values of dog subjects, pre-treatment and post-treatment. Glycosylated fructosamine is a measure of systemice inflammation. In human T1D, A1C is measured. Dog subject data for FIG. 13 were treated as described above. Prior to dosing with peptide, peripheral blood chemistry panels were performed and collected. Fructosamine levels were included. When systemic inflammation occurs, fructosamine levels are higher. After 8 weeks of treatment, fructosamine levels were measured again and compared to original numbers. The white square is pre-treatment value and black circle is the corresponding value post-treatment. Levels of fructosamine were reduced in each dog.

FIG. 14a, FIG. 14b, FIG. 14c, FIG. 14d, and FIG. 14e provide graphs of c-peptide measurements during treatment for dog subjects 1-5. C-peptide is a measure of potential beta cell recovery. When beta cell islets produce insulin, c-peptide levels increase. Here, plasma was sampled pre- and post-treatment. Plasma was analyzed for c-peptide using commercially available test kits. This ELISA, enzyme-linked immune-sorbent assay, showed that in all cases c-peptide levels increased after treatment. This indicates that treatment affected and restored normal beta cell activity, proper production of insulin. FIG. 14a, FIG. 14b, FIG. 14c, FIG. 14d, and FIG. 14e provide the results of these c-peptide measurement studies.

Example 10

Figure 18:
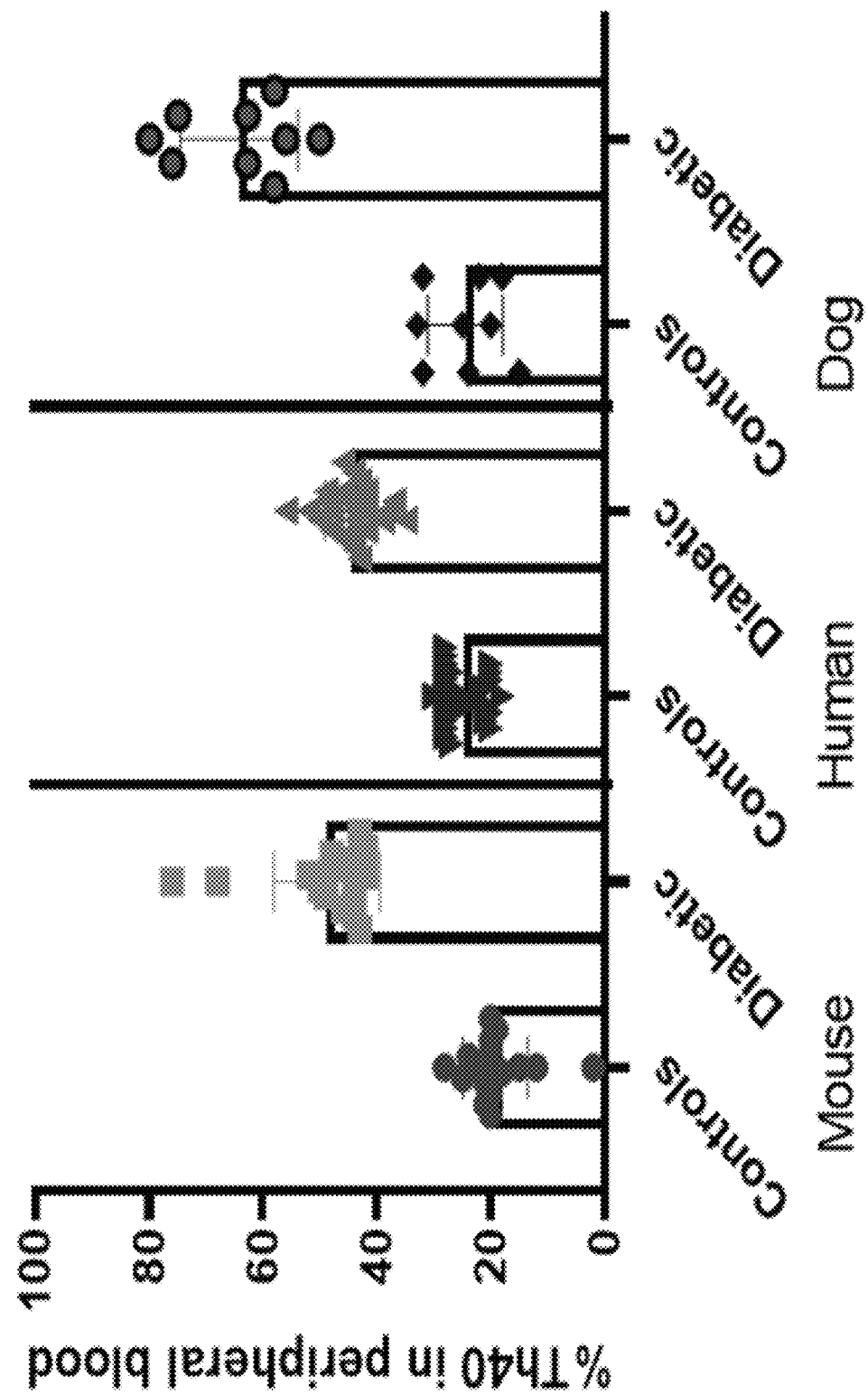
FIG. 18 provides a graph comparing the peripheral Th40 cell percentages in mouse, human, and dog subjects.

The percentage of Th40 cells in peripheral blood was studied in mouse, human and dog subjects. The results are shown in FIG. 18. Thus, FIG. 18 provides a graph of control and diabetic mouse, human and dog subjects. In this study, peripheral blood from non-diabetic dogs (n=12) was compared to diabetic dogs (n=9). All dogs were from the Colorado State University Veterinary Teaching Hospital, where they were all examined and seen in clinic. The determination of Th40 is the same in dog, as for mouse and human: CD4+CD3+CD40+ with confirmed TCR expression.

Example 11

Figure 21:
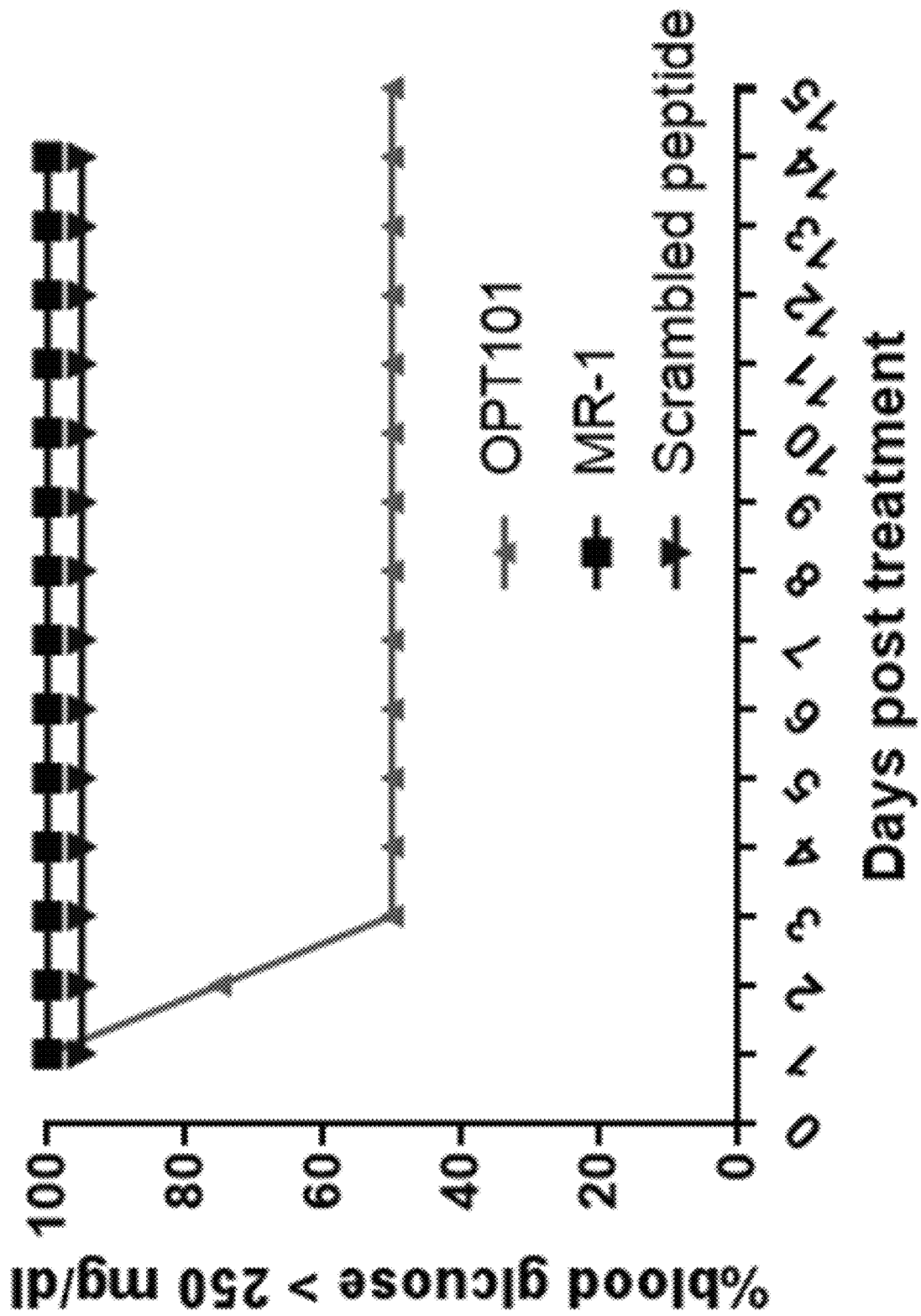
FIG. 21 is a graph demonstrating the effect of a peptide treatment on hyperglycemia in diabetic NOD mice.

This example was performed in mice; however, it demonstrates that KGYY-15 (SEQ ID NO: 11) may be utilized to significantly reduce and/or reverse hyperglycemia in diabetic NOD mice. In this study, NOD mice, blood glucose between 250-400 mg/dl were treated with KGYY-15. Control mice were treated with MR1 an anti-CD154 antibody or scrambled 15-mer peptide (SEQ ID NO: 17). KGYY-15 (SEQ ID NO: 11) reduced blood glucose in 57% of mice treated, the controls MR1 and scrambled 15-mer peptide had no effect. These results are provided in graph format shown in FIG. 21.

Example 12

Figure 22:
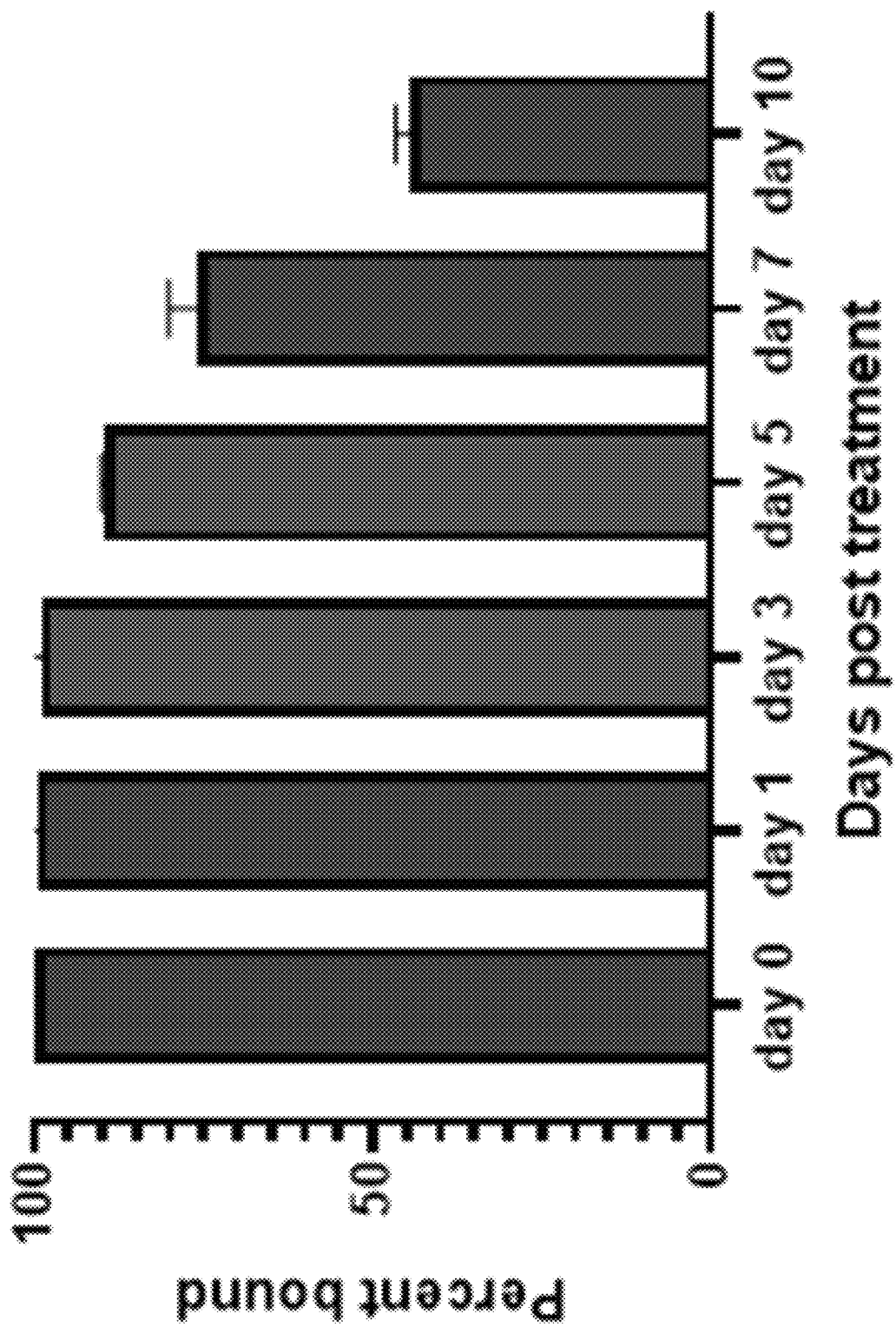
FIG. 22 is a graph of binding of a peptide to live cells in culture over time.

FIG. 22 provides a graph showing the binding stability of KGYY-15 (SEQ ID NO:11). KGYY-15 bound to human or mouse CD4+CD40+ cells maintained in culture for 10 days. KGYY15 was highly stable through 5 days, dropping off at 7 days, and again dropping off at 10 days. Cell death was the leading cause for binding loss.

Example 13

Figure 23:
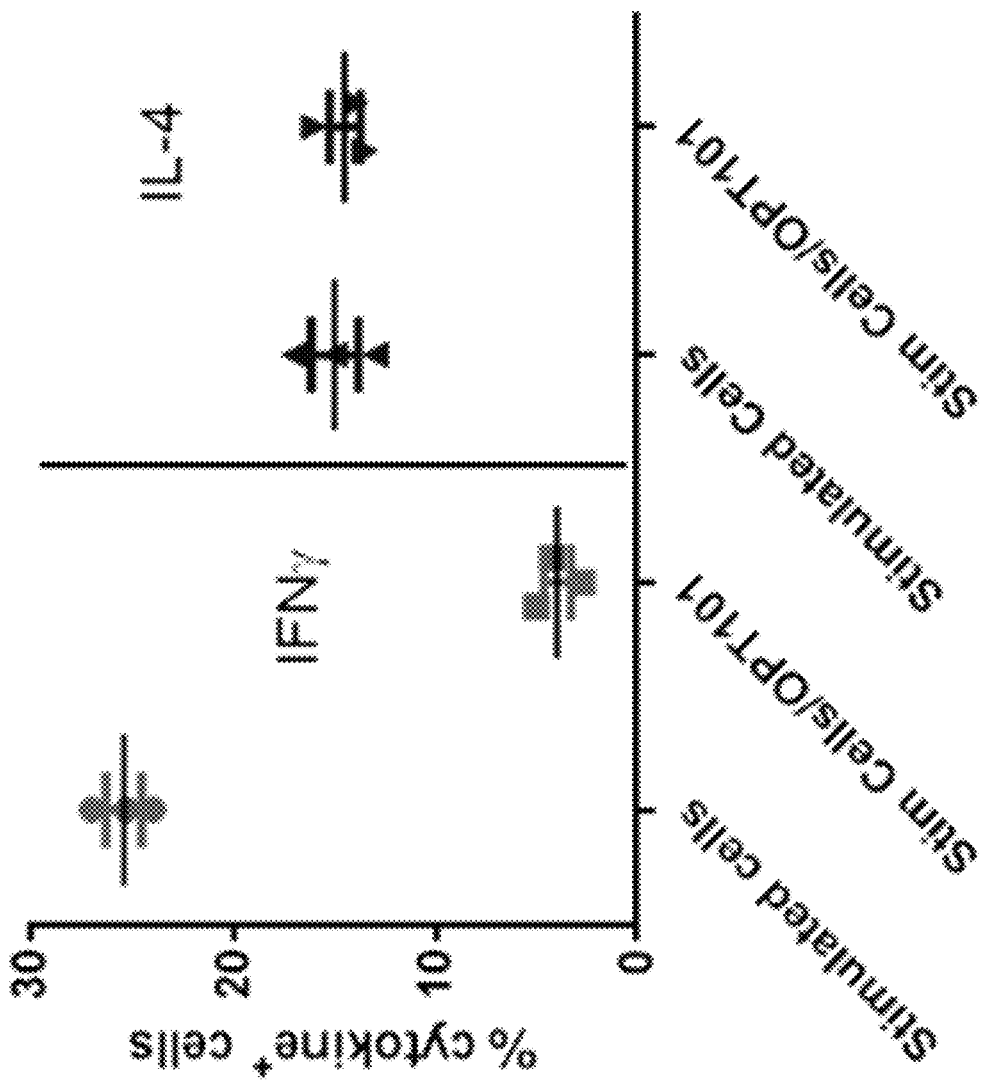
FIG. 23 provides a graph demonstrating that SEQ ID NO:11 regulates the inflammatory cytokine IFNγ without impacting production of non-inflammatory cytokine IL-4.

FIG. 23 provides a graph demonstrating that SEQ ID NO:11 regulates the inflammatory cytokine IFNγ without impacting production of non-inflammatory cytokine IL-4. In this study, human T cells, isolated from peripheral blood of T1D subjects, were stimulated with autologous antigen presenting cells loaded with human islets in the absence/presence of KGYY15 (SEQ ID NO:11) then intracellular IFNγ and IL-4 were measured by flow cytometry. P<0.001 for IFNγ.

Example 14

Figure 24:
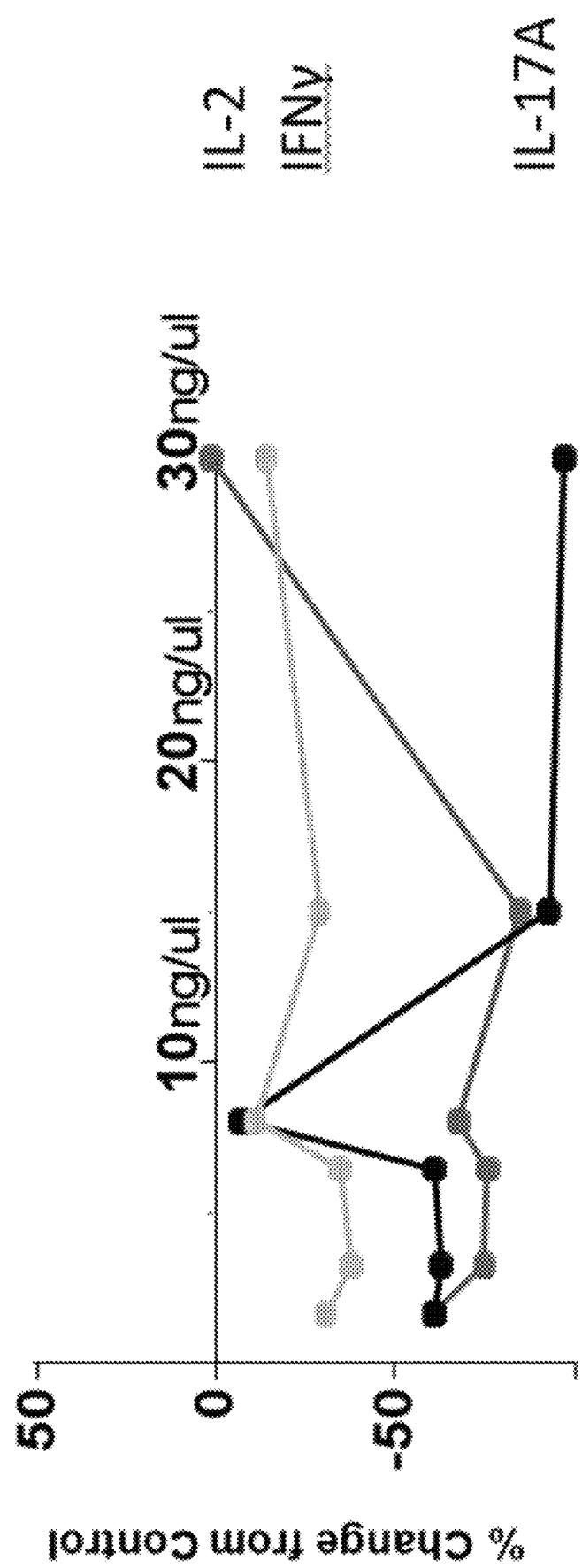
FIG. 24 provides a graph showing that different concentrations of peptide of SEQ ID NO:46 affects or influences levels of IL-2, IFNγ, and IL-17A.

FIG. 24 provides a graph showing that different concentrations of peptide of SEQ ID NO:46 affects or influences levels of IL-2, IFNγ, and IL-17A. In this study, CD3+CD4+ CD40+ (Th40) splenic cells were purified from ApoE$^{-/-}$ with cardiovascular disease. The cells were cultured overnight in the absence/presence of varying concentrations of KGYY6 peptide. Treated cells demonstrated varying degrees of reduction in the inflammatory cytokines IL-2, IFNγ and IL-17A compared to the untreated cells.

Example 15

FIG. 25 provides a graph showing the effect that treatment with SEQ ID NO: 13 had on the keytones as measured in the urine obtained from the dog test subjects described in Example 9. Keytones were measured in urine at the start of the study and approximately every 2 weeks thereafter. The dog subjects treated with SEQ ID NO: 13 demonstrated that treatment with SEQ ID NO:13 resulted in all dog subjects reaching 0 keytone measurement by the end of the study.

From the foregoing, it is readily apparent that new and useful implementations of the methods have been herein described and illustrated which fulfill numerous desiderata in remarkably unexpected fashions. It is, of course, understood that such modifications, alterations and adaptations as may readily occur to the artisan confronted with this disclosure are intended within the spirit of this disclosure, which is limited only by the scope of the claims appended hereto.

What is claimed:

1. A peptide of six amino acids in length consisting of the amino acid sequence of SEQ ID NO: 45, or 46.

2. The peptide of claim 1, wherein the peptide is formulated to be administered via intramuscular (IM) delivery, intravenous (IV) delivery, subcutaneous (SC) delivery, oral delivery, gavage delivery, emollient/skin delivery, transdermal patch, and/or intranasally.

3. The peptide of claim 1, wherein the peptide is produced synthetically.

4. The peptide of claim 1, wherein the N-terminal amino acid is acetylated.

5. A pharmaceutical composition comprising the peptide of claim 1 and a pharmaceutically acceptable carrier.

6. A pharmaceutical composition comprising a peptide of claim 1, a sterile solubilizing agent, and a buffering agent.

7. The pharmaceutical composition according to claim 6 further comprising a sugar.

8. The pharmaceutical composition according to claim 6, wherein the solubilizing agent is water.

9. The pharmaceutical composition of claim 6, wherein the peptide is pegylated, glycosylated, or comprises a chemical medication, or is acetylated at the N-terminus.

10. A method for modulating and/or reducing diabetes mellitus in a subject, the method comprising administering a peptide of claim 1 to the subject.

11. The method of claim 10, wherein the subject is a dog, cat, or horse.

12. The method of claim 10, wherein administering the peptide alters the cytokine expression profile of a cell population treated with said peptide.

13. The method of claim 10, wherein said peptide binds to an antigen presenting cell.

14. The method of claim 10, wherein administering said peptide modulates and/or reduces IFN-γ in the subject.

15. The method of claim 10, wherein administering said peptide modulates and/or reduces interleukin-2 signaling in the subject.

16. The method of claim 10, wherein administering said peptide modulates and/or reduces expression of interleukin 17 (IL-17) by a cell in the subject.

17. The method of claim 10, wherein administering said peptide modulates and/or reduces blood glucose levels of the subject.

18. The method of claim 10, wherein administering said peptide modulates and/or reduces fructosamine serum values in the subject.

19. The method of claim 10, wherein administering said peptide modifies, changes, or affects the c-peptide levels of the subject.

20. The method of claim 13, wherein the antigen presenting cell is a bone marrow derived cell type that expresses CD40 of approximately 45 kDa.

21. The method of claim 20, wherein the bone marrow derived cell type is a splenic CD4hi cell or CD8 cell.

* * * * *

SEQUENCE LISTING

<160> NUMBER OF SEQ ID NOS: 52

<210> SEQ ID NO 1
<211> LENGTH: 260
<212> TYPE: PRT
<213> ORGANISM: Mus musculus

<400> SEQUENCE: 1

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 2
<211> LENGTH: 261
<212> TYPE: PRT
<213> ORGANISM: Homo sapiens

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val

```
            50                  55                  60
Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
                195                 200                 205

Ala Asn Thr His Ser Ser Ala Lys Pro Cys Gly Gln Gln Ser Ile His
                210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

<210> SEQ ID NO 3
<211> LENGTH: 260
<212> TYPE: PRT
<213> ORGANISM: Canis lupus familiaris

<400> SEQUENCE: 3

Met Ile Glu Thr Tyr Ser Gln Thr Ala Pro Arg Ser Val Ala Thr Gly
 1               5                  10                  15

Pro Pro Val Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu Tyr Glu Asp Phe Val
 50                  55                  60

Phe Met Lys Thr Leu Gln Lys Cys Asn Lys Gly Glu Gly Ser Leu Ser
 65                  70                  75                  80

Leu Leu Asn Cys Glu Glu Ile Lys Ser Gln Phe Glu Ala Phe Leu Lys
                 85                  90                  95

Glu Ile Met Leu Asn Asn Glu Met Lys Lys Glu Asn Ile Ala Met
            100                 105                 110

Gln Lys Gly Asp Gln Asp Pro Arg Ile Ala Ala His Val Ile Ser Glu
            115                 120                 125

Ala Ser Ser Asn Pro Ala Ser Val Leu Arg Trp Ala Pro Lys Gly Tyr
            130                 135                 140

Tyr Thr Ile Ser Ser Asn Leu Val Ser Leu Glu Asn Gly Lys Gln Leu
145                 150                 155                 160
```

```
Ala Val Lys Arg Gln Gly Leu Tyr Tyr Val Tyr Ala Gln Val Thr Phe
                165                 170                 175

Cys Ser Asn Arg Ala Ala Ser Ser Gln Ala Pro Phe Val Ala Ser Leu
            180                 185                 190

Cys Leu His Ser Pro Ser Gly Thr Glu Arg Val Leu Leu Arg Ala Ala
            195                 200                 205

Ser Ser Arg Gly Ser Ser Lys Pro Cys Gly Gln Gln Ser Ile His Leu
        210                 215                 220

Gly Gly Val Phe Glu Leu His Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260

<210> SEQ ID NO 4
<211> LENGTH: 260
<212> TYPE: PRT
<213> ORGANISM: Felis catus

<400> SEQUENCE: 4

Met Ile Glu Thr Tyr Ser Gln Thr Ala Pro Arg Ser Val Ala Pro Gly
1               5                   10                  15

Pro Pro Val Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu Tyr Glu Asp Phe Val
50                  55                  60

Phe Met Lys Thr Leu Gln Lys Cys Asn Lys Gly Glu Gly Ala Leu Ser
65                  70                  75                  80

Leu Leu Asn Cys Glu Glu Ile Lys Ser Arg Phe Glu Ala Phe Leu Lys
                85                  90                  95

Glu Ile Met Leu Asn Lys Glu Thr Lys Lys Glu Lys Asn Val Ala Met
            100                 105                 110

Gln Lys Gly Asp Gln Asp Pro Arg Val Ala Ala His Val Ile Ser Glu
            115                 120                 125

Ala Ser Ser Ser Thr Ala Ser Val Leu Gln Trp Ala Pro Lys Gly Tyr
            130                 135                 140

Tyr Thr Ile Ser Ser Asn Leu Val Thr Leu Glu Asn Gly Lys Gln Leu
145                 150                 155                 160

Ala Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Ala Ser Leu
            180                 185                 190

Cys Leu His Ser Pro Ser Gly Ser Glu Arg Val Leu Leu Arg Ala Ala
            195                 200                 205

Asn Ala Arg Ser Ser Ser Lys Pro Cys Gly Gln Gln Ser Ile His Leu
        210                 215                 220

Gly Gly Val Phe Glu Leu His Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260
```

<210> SEQ ID NO 5
<211> LENGTH: 261
<212> TYPE: PRT
<213> ORGANISM: Equus caballus

<400> SEQUENCE: 5

Met Ile Glu Thr Tyr Ser Gln Pro Ser Pro Arg Ser Val Ala Thr Gly
1               5                   10                  15

Pro Pro Val Ser Met Lys Ile Phe Met Tyr Leu Leu Thr Val Phe Leu
            20                  25                  30

Ile Thr Gln Met Ile Val Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Lys Gly Glu Gly Pro Leu Ser
65                  70                  75                  80

Leu Leu Asn Cys Glu Gly Ile Arg Ser Gln Phe Glu Gly Phe Val Lys
                85                  90                  95

Asp Ile Met Leu Asn Glu Glu Val Lys Lys Lys Gly Glu Asn Phe Glu
            100                 105                 110

Met Gln Lys Gly Asp Gln Glu Pro Gln Ile Ala Ala His Val Ile Ser
        115                 120                 125

Glu Ala Ser Ser Lys Thr Ala Ser Val Leu Gln Trp Ala Gln Lys Gly
    130                 135                 140

Tyr Tyr Thr Ile Ser Asn Asn Leu Val Thr Leu Glu Asn Gly Lys Gln
145                 150                 155                 160

Leu Ala Val Lys Arg Gln Gly Leu Tyr Tyr Ile Tyr Ala Gln Val Thr
                165                 170                 175

Phe Cys Ser Asn Arg Glu Ala Ser Gly Gln Ala Pro Phe Ile Ala Ser
            180                 185                 190

Leu Cys Leu Arg Ser Val Ser Gly Ser Glu Arg Ile Leu Leu Arg Ala
        195                 200                 205

Ala Asn Thr His Ser Ser Ser Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (4)..(4)
<223> OTHER INFORMATION: amidation

<400> SEQUENCE: 6

Lys Gly Tyr Tyr

-continued

```
<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 7

Lys Lys Gly Tyr Tyr Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 8

Glu Lys Gly Tyr Tyr Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 9

Pro Lys Gly Tyr Tyr Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
```

```
<223> OTHER INFORMATION: amidation

<400> SEQUENCE: 10

Gln Lys Gly Tyr Tyr Thr
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 11

Val Leu Gln Trp Ala Lys Lys Gly Tyr Tyr Thr Met Lys Ser Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 12

Val Leu Gln Trp Ala Glu Lys Gly Tyr Tyr Thr Met Ser Asn Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 13

Val Leu Arg Trp Ala Pro Lys Gly Tyr Tyr Thr Ile Ser Ser Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 14

Val Leu Gln Trp Ala Pro Lys Gly Tyr Tyr Thr Ile Ser Ser Asn
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 15

Val Leu Gln Trp Ala Gln Lys Gly Tyr Tyr Thr Ile Ser Asn Asn
1               5                   10                  15

<210> SEQ ID NO 16
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (24)..(24)

<400> SEQUENCE: 16

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Tyr Lys Asn Val Lys Gln Met Ala Tyr Trp Leu Thr Gly Lys Ser
1               5                   10                  15

<210> SEQ ID NO 18
<211> LENGTH: 260
<212> TYPE: PRT
<213> ORGANISM: Mus musculus

<400> SEQUENCE: 18

Met Ile Glu Thr Tyr Ser Gln Pro Ser Pro Arg Ser Val Ala Thr Gly
1               5                   10                  15
```

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 19
<211> LENGTH: 261
<212> TYPE: PRT
<213> ORGANISM: Homo sapien

<400> SEQUENCE: 19

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser

```
                115                 120                 125
Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (4)..(4)
<223> OTHER INFORMATION: amidation

<400> SEQUENCE: 20

Lys Gly Tyr Tyr
1

<210> SEQ ID NO 21
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 21

Lys Lys Gly Tyr Tyr Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (8)..(8)
<223> OTHER INFORMATION: amidation

<400> SEQUENCE: 22

Ala Lys Lys Gly Tyr Tyr Thr Met
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (8)..(8)
<223> OTHER INFORMATION: amidation

<400> SEQUENCE: 23

Ala Glu Lys Gly Tyr Tyr Thr Met
1               5

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 24

Val Leu Gln Trp Ala Lys Lys Gly Tyr Tyr Thr Met Lys Ser Asn
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 25

Val Leu Gln Trp Ala Glu Lys Gly Tyr Tyr Thr Met Ser Asn Asn
1               5                   10                  15

<210> SEQ ID NO 26
<211> LENGTH: 24
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (24)..(24)
<223> OTHER INFORMATION: amidation

<400> SEQUENCE: 26

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 27
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 27

Ile Ser Gln Ala Val His Ala Ala His Ala Glu Ile Asn Glu Ala Gly
1               5                   10                  15

Arg

<210> SEQ ID NO 28
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 28

Gly Leu Gln Trp Ala Lys Lys Gly Tyr Tyr Thr Met Lys Ser Asn
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 29

Val Gly Gln Trp Ala Lys Lys Gly Tyr Tyr Thr Met Lys Ser Asn
1               5                   10                  15
```

```
<210> SEQ ID NO 30
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 30

Val Leu Gly Trp Ala Lys Lys Gly Tyr Tyr Thr Met Lys Ser Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 31

Val Leu Gln Gly Ala Lys Lys Gly Tyr Tyr Thr Met Lys Ser Asn
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 32

Val Leu Gln Trp Gly Lys Lys Gly Tyr Tyr Thr Met Lys Ser Asn
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 33
```

```
Val Leu Gln Trp Ala Gly Lys Gly Tyr Tyr Thr Met Lys Ser Asn
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 34

Val Leu Gln Trp Ala Lys Gly Gly Tyr Tyr Thr Met Lys Ser Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 35

Val Leu Gln Trp Ala Lys Lys Gly Gly Tyr Thr Met Lys Ser Asn
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 36

Val Leu Gln Trp Ala Lys Lys Gly Tyr Gly Thr Met Lys Ser Asn
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
```

```
<221> NAME/KEY: MISC_FEATURE
<222> LOCATION: (15)..(15)
<223> OTHER INFORMATION: amidation

<400> SEQUENCE: 37

Val Leu Gln Trp Ala Lys Lys Gly Tyr Tyr Gly Met Lys Ser Asn
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (15)..(15)
<223> OTHER INFORMATION: amidation

<400> SEQUENCE: 38

Val Leu Gln Trp Ala Lys Lys Gly Tyr Tyr Thr Gly Lys Ser Asn
1               5                   10                  15

<210> SEQ ID NO 39
<211> LENGTH: 17
<212> TYPE: PRT
<213> ORGANISM: Artificial sequence
<220> FEATURE:
<223> OTHER INFORMATION: Synthetic peptide

<400> SEQUENCE: 39

Ile Ser Gln Ala Val His Ala Ala His Ala Glu Ile Asn Glu Ala Gly
1               5                   10                  15

Arg

<210> SEQ ID NO 40
<211> LENGTH: 15
<212> TYPE: PRT
<213> ORGANISM: Artificial sequence
<220> FEATURE:
<223> OTHER INFORMATION: Synthetic peptide

<400> SEQUENCE: 40

Tyr Val Gln Gly Lys Ala Asn Leu Lys Ser Lys Leu Met Tyr Thr
1               5                   10                  15

<210> SEQ ID NO 41
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (10)..(10)
<223> OTHER INFORMATION: amidation

<400> SEQUENCE: 41

Trp Ala Lys Lys Gly Tyr Tyr Thr Met Lys
1               5                   10
```

```
<210> SEQ ID NO 42
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (13)..(13)
<223> OTHER INFORMATION: amidation

<400> SEQUENCE: 42

Val Leu Gln Trp Ala Lys Lys Gly Tyr Tyr Thr Met Lys
1               5                   10

<210> SEQ ID NO 43
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (24)..(24)
<223> OTHER INFORMATION: amidation

<400> SEQUENCE: 43

Ala Ala Ser Val Leu Gln Trp Ala Lys Lys Gly Tyr Tyr Thr Met Lys
1               5                   10                  15

Ser Asn Leu Val Met Leu Glu Asn
            20

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 44

Lys Gly Tyr Tyr Thr Met
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
```

```
<222> LOCATION: (6)..(6)
<223> OTHER INFORMATION: amidation

<400> SEQUENCE: 45

Ala Glu Lys Gly Tyr Tyr
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 46

Ala Lys Lys Gly Tyr Tyr
1               5

<210> SEQ ID NO 47
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 47

Ala Lys Gly Tyr Tyr Thr
1               5

<210> SEQ ID NO 48
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (24)..(24)
<223> OTHER INFORMATION: amidation

<400> SEQUENCE: 48

Ala Ala Ser Val Leu Gln Trp Ala Lys Lys Gly Tyr Tyr Thr Met Lys
1               5                   10                  15

Ser Asn Leu Val Met Leu Glu Asn
            20

<210> SEQ ID NO 49
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 49

Tyr Lys Asn Val Lys Gln Met Ala Tyr Trp Leu Thr Gly Lys Ser
1               5                   10                  15

<210> SEQ ID NO 50
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 50

Ala Pro Lys Gly Tyr Tyr
1               5

<210> SEQ ID NO 51
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 51

Ala Gln Lys Gly Tyr Tyr
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: glycation, alkylation, acetylation, acylation
<220> FEATURE:
<221> NAME/KEY: MISC_FEATURE
<222> LOCATION: (6)..(6)
<223> OTHER INFORMATION: amidation

<400> SEQUENCE: 52

Lys Gly Tyr Tyr Thr Ile
1               5
```